United States Patent
Jaye et al.

(10) Patent No.: US 7,008,776 B1
(45) Date of Patent: *Mar. 7, 2006

(54) COMPOSITIONS AND METHODS FOR EFFECTING THE LEVELS OF HIGH DENSITY LIPOPROTEIN (HDL) CHOLESTEROL AND APOLIPOPROTEIN AI VERY LOW DENSITY LIPOPROTEIN (VLDL) CHOLESTEROL AND LOW DENSITY LIPOPROTEIN (LDL) CHOLESTEROL

(75) Inventors: Michael Jaye, Glenside, PA (US); Kim-Anh Thi Doan, Spring City, PA (US); John A. Krawiec, Gulph Mills, PA (US); Kevin J. Lynch, Gurnee, IL (US); Dilip V. Amin, Lansdale, PA (US); Victoria J. South, Collegeville, PA (US); Dawn Marchadier, Sickelerville, NJ (US); Cyrille Maugeais, Philadelphia, PA (US); Daniel J. Rader, Collegeville, PA (US)

(73) Assignees: Aventis Pharmaceuticals Inc., Bridgewater, NJ (US); The Trustees of the University of Pennsylvania, Philadelphia, PA (US)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/277,401

(22) Filed: Mar. 26, 1999

Related U.S. Application Data

(63) Continuation-in-part of application No. 08/985,492, filed on Dec. 5, 1997, now Pat. No. 6,395,530.

(60) Provisional application No. 60/032,254, filed on Dec. 6, 1996, provisional application No. 60/032,783, filed on Dec. 6, 1996.

(51) Int. Cl.
*G01N 33/573* (2006.01)
*C12N 9/20* (2006.01)

(52) U.S. Cl. .................... 435/7.4; 435/198
(58) Field of Classification Search ............... 435/198, 435/7.1
See application file for complete search history.

(56) References Cited

U.S. PATENT DOCUMENTS

| | | | |
|---|---|---|---|
| 4,797,368 A | 1/1989 | Carter et al. | 435/320 |
| 4,861,719 A | 8/1989 | Miller | 435/236 |
| 4,987,071 A | 1/1991 | Cech et al. | 435/91 |
| 5,139,941 A | 8/1992 | Muzyczka et al. | 435/172.3 |
| 5,168,062 A | 12/1992 | Stinski | 435/240.2 |
| 5,385,839 A | 1/1995 | Stinski | 435/240.2 |
| 5,459,127 A | 10/1995 | Felgner et al. | 514/7 |
| 5,580,859 A | 12/1996 | Felgner et al. | 514/44 |
| 5,589,466 A | 12/1996 | Felgner et al. | 514/44 |
| 5,616,483 A * | 4/1997 | Bjursell et al. | 435/198 |
| 5,691,181 A * | 11/1997 | Lowe | 435/325 |
| 5,693,622 A | 12/1997 | Wolff et al. | 514/44 |
| 5,846,947 A | 12/1998 | Behr et al. | 514/44 |
| 5,856,435 A | 1/1999 | Bazile et al. | 530/300 |
| 5,858,755 A * | 1/1999 | Lowe | 435/198 |
| 5,866,551 A | 2/1999 | Benoit et al. | 514/44 |
| 5,945,400 A | 8/1999 | Scherman et al. | 514/13 |
| 6,040,174 A | 3/2000 | Imler et al. | 435/325 |
| 6,043,339 A | 3/2000 | Lin et al. | 530/300 |
| 6,337,187 B1 * | 1/2002 | Kapeller-Libermann | 435/6 |
| 6,395,530 B1 * | 5/2002 | Jaye et al. | 435/198 |
| 6,558,936 B1 * | 5/2003 | Khodadoust et al. | 435/198 |
| 6,797,502 B1 * | 9/2004 | Kapeller-Libermann | 435/198 |
| 6,864,064 B1 * | 3/2005 | Kapeller-Libermann | 435/15 |
| 2003/0108538 A1 * | 6/2003 | Jaye et al. | 424/94.6 |

FOREIGN PATENT DOCUMENTS

| | | |
|---|---|---|
| AU | 713662 | 6/1996 |
| CA | 2012311 | 9/1990 |
| EP | 0178220 B1 | 1/1992 |
| EP | 0185573 B1 | 5/1992 |

| | | | |
|---|---|---|---|
| EP | 0140308 B1 | 1/1993 | |
| EP | 0488528 B1 | 11/1995 | |
| EP | 0453242 B1 | 8/1996 | |
| WO | WO 89/07150 | 8/1989 | |
| WO | WO 90/02806 | 3/1990 | |
| WO | WO 91/18088 | 11/1991 | |
| WO | WO 92/15680 | 9/1992 | |
| WO | WO 93/09239 | 5/1993 | |
| WO | WO 93/23569 | 11/1993 | |
| WO | WO 94/02595 | 2/1994 | |
| WO | WO 94/02610 | 2/1994 | |
| WO | WO 94/12649 | 6/1994 | |
| WO | WO 94/20619 | 9/1994 | |
| WO | WO 94/28938 | 12/1994 | |
| WO | WO 94/29446 | 12/1994 | |
| WO | WO 95/02697 | 1/1995 | |
| WO | WO 96/01313 | 1/1996 | |
| WO | WO 98/24888 | 6/1998 | |
| WO | WO 99/32611 | 7/1999 | |

OTHER PUBLICATIONS

Cooper, D. et al., GenBank Database, Accession No. P11602, 1989.*

Cooper et al. Avian adipose lipoprotein lipase: cDNA sequence and reciprocal regulation of mRNA levels in adipose and heart. Biochim. Biosphy. Acta (1989) 1008:92-101.*

Gershenwald et al. Monoclonal antibodies to avian lipoprotein lipase. Purification of the enzyme by immunoaffinity chromatography. Biochim. Biosphy. Acta (1985) 836: 286-295 (Abstract only).*

Morabia et al. Human Molecular Genetics (2003) 12(21): 2733-2743.*

Jaye et al. A novel endothelial-derived lipase that modulates HDL metabolism. Nature Genetics (1999) 21: 424-428.*

Hirata et al. Cloning of a Unique Lipase from Endothelial Cells Extends the Lipase Gene Family (1999) 274(20): 14170-14175.*

Ikeda et al. Journal of Lipid Research (1990) 31:1911-1924.*

Eisenberg, S. et al., Lipoprotein Lipase Enhances Binding of Lipoproteins to Heparan Sulfate on Cell Surfaces and Extracellular Matrix, *J. Clin. Invest.* (Nov. 1992), 90: 2013-2021.

Goldberg, I.J. et al., Lipoprotein Metabolism During Acute Inhibition of Lipoprotein Lipase in the Cynomolgus Monkey, *J. Clin. Invest.* (Feb. 1988), 81:561-568.

Goldberg, I.J. et al., Lipoprotein Metabolism During Acute Inhibition of Hepatic Triglyceride Lipase in the Cynomolgus Monkey, *J. Clin. Invest.* (Dec. 1982), 70: 1184-1192.

Hide, W.A. et al., Structure and Evolution of the Lipase Superfamily, *J. Lipid Res.* (1992), 33: 167-178.

Giller, T. et al., Two Novel Human Pancreatic Lipase Related Proteins, hPLRP1 and hPLRP2, *J. Biol. Chem.* (Aug. 15, 1992), 267: 16509-16516.

Winkler, F.K. et al., Structure of Human Pancreatic Lipase, *Nature* (Feb. 22, 1990), 343: 771-774.

Wong, H. et al., Domain Exchange: Characterization of a Chimeric Lipase of Hepatic Lipase and Lipoprotein Lipase, *Proc. Natl. Acad. Sci. USA* (Dec. 1991), 88:11290-11294.

van Tilbeurgh, H. et al., Lipoprotein Lipase, *J. of Biol. Chem.* (Feb. 11, 1994), 269: 4626-4633.

Wong, H. et al., Lipoprotein Lipase Domain Function, *J. of Biol. Chem.* (Apr. 8, 1994), 269: 10319-10323.

Chappell, D.A. et al., Cellular Catabolism of Normal Very Low Density Lipoproteins via the Low Density Lipoprotein Receptor-related Protein/ $a_2$-Macroglobulin Receptor is Induced by the C-terminal Domain of Lipoprotein Lipase, *J. Biol. Chem.* (Jul. 8, 1994), 269: 18001-18006.

Semenkovich, C.F. et al., In Vitro Expression and Site-specific Mutagenesis of the Cloned Human Lipoprotein Lipase Gene, *J. Biol. Chem.* (Apr. 5, 1990), 265: 5429-5433.

Lo, J. et al., Lipoprotein Lipase: Role of Intramolecular Disulfide Bonds in Enzyme Catalysis, *Biochemical and Biophysical Res. Commun.* (Jan. 5, 1995), 206: 266-271.

Brady, L. et al., A Serine Protease Triad Forms the Catalytic Centre of a Triacylglycerol Lipase, *Nature* (Feb. 22, 1990), 343: 767-769.

Faustinella, F. et al., Functional Topology of a Surface Loop Shielding the Catalytic Center in Lipoprotein Lipase, *Biochemistry* (1992), 31: 7219-7223.

Dugi, K. et al., Human Hepatic and Lipoprotein Lipase: The Loop Covering the Catalytic Site Mediates Lipase Substrate Specificity, *J. of Biol. Chem.* (Oct. 27, 1995), 270: 25396-25401.

Ma, Y. et al., Mutagenesis in Four Candidate Heparin Binding Regions (Residues 279-282, 291-304, 390-393, and 439-448) and Identification of Residues Affecting Heparin Binding of Human Lipoprotein Lipase, *J. Lipid Res.* (1994), 35: 2049-2059.

Cheng, C. et al., Binding of Lipoprotein Lipase to Endothelial Cells in Culture, *J. Biol. Chem.* (Dec. 25, 1981), 256: 12893-12898.

Shimada, K. et al., Involvement of Cell Surface Heparin Sulfate in the Binding of Lipoprotein Lipase to Cultured Bovine Endothelial Cells, *J. Clin. Invest.* (Oct. 1981), 68: 995-1002.

Saxena, U. et al., Identification and Characterization of the Endothelial Cell Surface Lipoprotein Lipase Receptor, *J. Biol. Chem.* (Sep. 15, 1991), 266: 17516-17521.

Mulder, M. et al., Heparan Sulfate Proteoglycans are Involved in the Lipoprotein Lipase-Mediated Enhancement of the Cellular Binding of Very Low Density and Low Density Lipoproteins, *Biochem. Biophys. Res. Commun.* (Jun. 15, 1992), 185: 582-587.

Rutledge, J.C. and I.J. Goldberg, Lipoprotein Lipase (LpL) Affects Low Density Lipoprotein (LDL) Flux Through Vascular Tissue: Evidence that LpL Increase LDL Accumulation in Vascular Tissue, *J. Lipid Res.* (1994), 35: 1152-60.

Tsuchiya, S. et al., Establishment and Characterization of a Human Acute Monocytic Leukemia Cell Line (THP-1), *Int. J. Cancer* (1980), 26: 171-176.

Ranganathan, G. et al., Tissue Specific Expression of Human Lipoprotein Lipase, *J. Biol. Chem.* (Mar. 31, 1995), 270: 7149-7155.

Ghosh, S. et al., Molecular Cloning and Expression of Rat Hepatic Neutral Cholesteryl Ester Hydrolase, *Biochem. Biophys. Acta* (1995), 1259: 305-312.

Warren, R. et al., Rabbit Hepatic Lipase cDNA Sequence: Low Activity is Associated with Low Messenger RNA Levels, *J. of Lipid Res.* (1991), 32: 1333-1339.

Martin, G. et al., Isolation and cDNA Sequence of Human Postheparin Plasma Hepatic Triglyceride Lipase, *J. of Biol. Chem.* (1996), 263: 10907-10914.

Goldberg, I.J., Lipoprotein Lipase and Lipolysis: Central Roles in Lipoprotein Metabolism and Atherogenesis, *J. Lipid Res.* (1996), 37: 693-707.

Gordon, D.J. and B.M. Rifkind, High Density Lipoprotein —The Clinical Implications of Recent Studies, *N. Engl. J. Med.* (Nov. 9, 1989), 321: 1311-1316.

Breslow, J.L., The Metabolic Basis of Inherited Disease, New York: McGraw Hill, 1995: 2031-2052.

Heller, D.A. et al., Genetic and Environmental Influences on Serum Lipid Levels in Twins, *N. Engl. J. Med.* (Apr. 22, 1993), 328: 1150-1156.

Murthy, V. et al., Molecular Pathobiology of the Human Lipoprotein Lipase Gene, *Pharmacol. Ther.* (1996), 70: 101-135.

Bensadoun, A. and D.E. Berryman, Genetics and Molecular Biology of Hepatic Lipase, *Curr. Opin. Lipidol.* (1996), 7: 77-81.

Cohen, J.C. et al., Variation at the Hepatic Lipase and Apolipoprotein AI/CIII/AIV Loci is a Major Cause of Genetically Determined Variation in Plasma HDL Cholesterol Levels, *J. Clin. Invest.* (Dec. 1994), 94: 2377-2384.

Guerra, R. et al., A Hepatic Lipase (LIPC) Allele Associated with High Plasma Concentrations of High Density Lipoprotein Cholesterol, *Proc. Natl. Acad. Sci. USA* (Apr. 1997), 94:4532-4537.

LIPID Study Group, Prevention of Cardiovascular Events and Death with Pravastatin in Patients with Coronary Heart Disease and a Broad Range of Initial Cholesterol Levels, *N. Engl. J. Med.* (Nov. 5, 1998), 339: 1349-1357.

Kannel, W.B., Range of Serum Cholesterol Values in the Population Developing Coronary Artery Disease, *Am. J. Cardiol.* (Sep. 28, 1995), 76; 69C-77C.

4S Group, Randomised Trial of Cholesterol Lowering in 4444 Patients with Coronary Heart Disease, *Lancet* (Nov. 19, 1994), 344: 1383-1389.

Sacks, F.M. et al., The Effects of Pravastatin on Coronary Events After Myocardial Infarction in Patients with Average Cholesterol Levels, *N. Engl. J. Med.* (Oct. 3, 1996), 335: 1001-1009.

Shepherd, J. et al., Prevention of Coronary Heart Disease with Pravastatin in Man with Hypercholesterolemia, *N. Engl. J. Med.* (Nov. 16, 1995), 333: 1301-1307.

Downs, J.R. et al., Primary Prevention of Acute Coronary Events with Lovastatin in Men and Women with Average Cholesterol Levels, *JAMA* (May 27, 1998), 279: 1615-1622.

Grundy, S.M., Statin Trials and Goals of Cholesterol-Lowering Therapy, *Circulation* (1998), 97: 1436-1439.

Olivecrona, G. and T. Olivecrona, Triglyceride Lipases and Atherosclerosis, *Curr. Opin. Lipidol.* (1995), 6: 291-305.

Shimada, M. et al., Overexpression of Human Lipoprotein Lipase in Transgenic Mice, *J. Biol. Chem.* (Aug. 25, 1993), 268: 17924-17929.

Liu, M. et al., Alteration of Lipid Profiles in Plasma of Transgenic Mice Expressing Human Lipoprotein Lipase, *J. Biol. Chem.* (Apr. 15, 1994), 269: 11417-11424.

Zilversmit, D.B., A Proposal Linking Atherogenesis to the Interaction of Endothelial Lipoprotein Lipase with Triglyceride-Rich Lipoproteins, *Circ. Res.* (Dec. 1973), 33: 633-638.

Hegele, R.A. et al., Hepatic Lipase Deficiency: Clinical, Biochemical, and Molecular Genetics Characteristics, *Arterioscler. Thromb.* (May 1993), 13: 720-728.

Homanics, G.E. et al., Mild Dyslipidemia in Mice Following Targeted Inactivation of the Hepatic Lipase Gene, *J. Biol. Chem.* (1995), 270: 2974-2980.

Mezdour, H. et al., Hepatic Lipase Deficiency Increases Plasma Cholesterol but Reduces Susceptibility to Atherosclerosis in Apolipoprotein E-deficient Mice, *J. Biol. Chem.* (May 23, 1997), 272: 13570-13575.

Busch, S.J. et al., Human Hepatic Triglyceride Lipase Expression Reduces High Density Lipoprotein and Aortic Cholesterol in Cholesterol-fed Transgenic Mice, *J. Biol. Chem.* (Jun. 10, 1994), 269: 16376-16382.

Fan, J. et al., Overexpression of Hepatic Lipase in Transgenic Rabbits Leads to a Marked Reduction of Plasma High Density Lipoproteins and Intermediate Density Lipoproteins, *Proc. Natl. Acad. Sci. USA* (Aug. 1994), 91: 8724-28.

Mahaney, M.C. et al., A Major Locus Influencing Plasma High-Density Lipoprotein Cholesterol Levels in the San Antonio Family Heart Study, *Arterioscler. Thromb.* (Oct. 1995), 15: 1730-1739.

Zilversmit, D.B., Atherogenic Nature of Triglycerides, Postprandial Lipidemia, and Triglyceride-Rich Remnant Lipoproteins, *Clin. Chem.* (1995), 41: 153-158.

Zambon, A. et al., Prevention of Raised Low-Density Lipoprotein Cholesterol in a Patient with Familial Hypercholesterolaemia and Lipoprotein Lipase Deficiency, *Lancet* (May 1, 1993), 341: 1119-1121.

Tabas, I et al., Lipoprotein Lipase and Sphingomyelinase Synergistically Enhance the Association of Atherogenic Lipoproteins with Smooth Muscle Cells and Extracellular Matrix, *J. Biol. Chem.* (Sep. 25, 1993), 268: 20419-32.

Nordestgaard, B.G. et al., Atherosclerosis and Arterial Influx of Lipoproteins, *Curr. Opin. Lipidol.* (1994), 5: 252-257.

Williams, K.J., The Response-to-Retention Hypothesis of Early Atherogenesis, *Art Thromb. and Vasc. Biol.* (1995), 15: 551-561.

Kozarsky, K.F. et al., Overexpression of the HDL Receptor SR-BI Alters Plasma HDL and Bile Cholesterol Levels, *Nature* (May 22, 1997), 387: 414-417.

Mahley, R.W. and Z. Ji, Remnant Lipoprotein Metabolism: Key Pathways Involving Cell-Surface Heparan Sulfate Proteoglycans and Apolipoprotein E, *J. Lipid Res.* (1999), 40: 1-16.

Farese, R.V. and J. Herz, Cholesterol Metabolism and Embryogenesis, *Trends Genet.* (Mar. 1998), 14: 115-120.

Ornitz, D.M. et al., Elastase I Promoter Directs Expression of Human Growth Hormone and SV40 T Antigen Genes to Pancreatic Acinar Cells in Transgenic Mice, *Cold Spring Harbor Symp. Quant. Biol.* (1986), 50: 399-409.

Macdonald, R.J., Expression of the Pancreatic Elastase I Gene in Transgenic Mice, *Hepatology* (1987), 7: 42S-51S.

Hanahan, D., Heritable Formation of Pancreatic β-Cell Tumours in Transgenic Mice Expressing Recombinant Insulin/Simian Virus 40 Oncogenes, *Nature,* (May 1985), 315: 115-122.

Grosschedl, R. et al., Introduction of a µ Immunoglobulin Gene into the Mouse Germ Line: Specific Expression in Lymphoid Cells and Synthesis of Functional Antibody, *Cell* (Oct. 1984), 38: 647-658.

Adams, J.M. et al., The c-myc Oncogene Driven by Immunoglobulin Enhancers Induces Lymphoid Malignancy in Transgenic Mice, *Nature* (Dec. 12, 1985), 318: 533-538.

Alexander, W.S. et al., Expression of the c-myc Oncogene Under Control of an Immunoglobulin Enhancer in Eµ-myc Transgenic Mice, *Mol. and Cell. Biol.* (Apr. 1987), 7: 1436-1444.

Leder, A. et al., Consequences of Widespread Deregulation of the c-myc Gene in Transgenic Mice: Multiple Neoplasms and Normal Development, *Cell* (May 23, 1986), 45: 485-495.

Pinkert, C.A. et al., An Albumin Enchancer Located 10 kb Upstream Functions Along with its Promoter to Direct Efficient, Liver-specific Expression in Transgenic Mice, *Genes and Devel.* (1987), 1:268-276.

Krumlauf, R. et al., Developmental Regulation of α-Fetoprotein Genes in Transgenic Mice, *Mol. and Cell. Biol.* (Jul. 1985), 5: 1639-1648.

Hammer, R.E. et al., Diversity of Alpha-Fetoprotein Gene Expression in Mice is Generated by a Combination of Separate Enhancer Elements, *Science* (Jan. 2, 1987), 235: 53-58.

Kelsey, G.D. et al, Species- and Tissue-specific Expression of Human $\alpha_1$-antitrypsin in Transgenic Mice, *Genes and Devel.* (1987), 1: 161-171.

Magram, J. et al., Developmental Regulation of a Cloned Adult β-globin Gene in Transgenic Mice, *Nature* (May 23, 1985), 315: 338-340.

Kollias, G. et al., Regulated Expression of Human $^a$γ-, β-, and Hybrid γβ- Globin Genes in Transgenic Mice: Manipulation of the Developmental Expression Patterns, *Cell* (Jul. 4, 1986), 46: 89-94.

Readhead, C. et al., Expression of a Myelin Basic Protein Gene in Transgenic Shiverer Mice: Correction of the Dysmyelinating Phenotype, *Cell* (Feb. 27, 1987), 48: 703-712.

Shani, M., Tissue-specific Expression of Rat Myosin Light-chain 2 Gene in Transgenic Mice, *Nature* (Mar. 21, 1985), 314: 283-286.

Mason, A.J. et al., The Hypogonadal Mouse: Reproductive Functions Restored by Gene Therapy, *Science* (Dec. 12, 1986), 234: 1372-1378.

Swift, G.H. et al., Tissue Specific Expression of the Rat Pancreatic Elastate I Gene in Transgenic Mice, *Cell* (1984), 38: 639-646.

Chowers, Y. et al., GenBank Database, Accession No. L32416.

Auffray, C. et al., GenBank Database, Accession No. Z44958.

Marra, M. et al., GenBank Database, Accession No. AA137809.

Bernstein et al., Gene Transfer with Retrovirus Vectors, *Genet. Eng.* (1985), 7: 235-261.

McCormick, D., Human Gene Therapy: The First Round, *Biotechnology* (Aug. 1985), 3: 689-693.

Narayan, O. and J.E. Clements, *Lentiviruses,* in Fields, B.N., *Virology,* ed. 2, New York: Raven Press, Ltd., 1990: 1571-1589.

Bender, M.A. et al., Evidence that the Packaging Signal of Moloney Murine Leukemia Virus Extends into the gag Region, *J. Virol.* (May 1987), 61: 1639-1646.

Beard, C.W. et al., Transcription Mapping of Mouse Adenovirus Type 1 Early Region 3, *Virology* (1990), 175: 81-90.

Graham, F.L. Covalently Closed Circles of Human Adenovirus DNA are Infectious, *EMBO J.* (1984), 3:2917-2922.

Graham, F.L. et al., Characteristics of a Human Cell Line Transformed by DNA from Human Adenovirus Type 5, *J. Gen. Virol.* (1977), 36: 59-72.

Levrero, M. et al., Defective and Nondefective Adenovirus Vectors for Expressing Foreign Genes In Vitro and In Vivo, *Gene* (1991), 101: 195-202.

Berkner, K., Development of Adenovirus Vectors for the Expression of Heterologous Genes, *Biotechniques* (1988), 6: 616-629.

Perrotta, A.T. and M.D. Been. Cleavage of Oligoribonucleotides by a Ribozyme Derived from the Hepatitis & Virus RNA Sequence, *Biochemistry* (1992), 31: 16-21.

Lieber, A. et al., Stable High-Level Gene Expression in Mammalian Cells by T7 Phage RNA Polymerase, *Methods Enzymol.* (1993), 217: 47-67.

Kashani-Sabet, M. et al., Reversal of the Malignant Phenotype by an Anti-ras Ribozyme, *Antisense Res. Dev.* (1992), 2: 3-15.

L'Huillier, P.J. et al., Cytoplasmic Delivery of Ribozymes Leads to Efficient Reduction in α-Lactalbumin mRNA Levels in C1271 Mouse Cells, *EMBO J.* (1992), 11: 4411-4418.

Lisziewics, J. et al., Inhibition of human immunodeficiency Virus Type 1 Replication by Regulated Expression of a Polymeric Tat Activation Response RNA Decoy as a Strategy for Gene Therapy in AIDS, *Proc. Natl. Acad. Sci. USA* (Sep. 1993), 90: 800-8004.

Yu, M. et al., A Hairpin Ribozyme Inhibits Expression of Diverse Strains of Human Immunodeficiency Virus Type 1, *Proc. Natl. Acad. Sci. USA* (Jul. 1993), 90: 6340-6344.

Zhou, Y. et al., Synthesis of Functional mRNA in Mammalian Cells by Bacteriophage T3 RNA Polymerase, *Mol. Cell. Biol.* (Sep. 1990), 10: 4529-4537.

Gao, X. and L. Huang, Cytoplasmic Expression of a Reporter Gene by Co-delivery of T7 RNA Polymerase and T& Promoter Sequence with Cationic Liposomes, *Nucleic Acids Research* (1993), 21: 2867-2872.

Elroy-Stein, O. and B. Moss, Cytoplasmic Expression System Based on Constitutive Synthesis of Bacteriophage T7 RNA Polymerase in Mammalian Cells, *Proc. Natl. Acad. Sci. USA* (Sep. 1990), 87: 6743-6747.

Ventura, M. et al., Activation of HIV-specific Ribozyme Activity by Self-cleavage, *Nuc. Acids. Res.* (1993), 21: 3249-3255.

Taira, K. et al., Construction of a Novel RNA-transcript-trimming Plasmid which Can be Used Both In Vitro In Place of Run-off and (G)-free Transcriptions and In Vivo as Multi-sequences Transcription Vectors, *Nuc. Acids Res.* (1991), 5125-5130.

Ohkawa, J. et al., Activities of HIV-RNA Targeted Ribozymes Transcribed from a "Shot-gun" Type Ribozyme-trimming Plasmid, *Nuc. Acids Symp. Ser.* (1992), 17: 15-16.

Sarver, N. et al., Ribozymes as Potential Anti-HIV-1 Therapeutic Agents, *Science* (March 9, 1990), 247: 1222-1225.

Chen, C. et al., Multitarget-ribozyme Directed to Cleave at up to Nine Highly Conserved HIV-1 env RNA Regions Inhibits HIV-1 Replication—Potential Effectiveness Against Most Presently Sequenced HIV-1 Isolates, *Nuc. Acids Res.* (1992), 20: 4581-4589.

Ojwang, J.O. et al., Inhibition of Human Immunodeficiency Virus Type 1 Expression in Hairpin Ribozyme, *Proc. Natl. Acad. Sci. USA* (Nov., 1992), 89: 10802-10806.

Weerasinghe, M. et al., Resistance to Human Immunodeficiency Virus Type 1 (HIV-1) Infection in Human $CD4^+$ Lymphocyte-Derived Cell Lines Conferred by Using Retroviral Vectors Expressing an HIV-1 RNA-Specific Ribozyme, *J. Virol.* (Oct. 1991), 65: 5531-5534.

Dropulić, B. et al., Functional Characterization of a U5 Ribozyme: Intracellular Suppression of Human Immunodeficiency Virus Type 1 Expression, *J. Virol.* (Mar. 1992), 66: 1432-1441.

Scanlon, K.J. et al., Ribozyme-mediated Cleavage of c-fos mRNA Reduces Gene Expression of DNA Synthesis Enzymes and metallothionein, *Proc. Natl. Acad. Sci. USA* (Dec. 1991), 88: 10591-10595.

Saville, B.J. and R.A. Collins, RNA-mediated Ligation of Self-cleavage Products of a *Neurospora* Mitochondrial Plasmid Transcrip, *Proc. Natl. Acad. Sci. USA* (Oct. 1991), 88: 8826-8830.

Saville, B.J. and R.A. Collins, A Site-Specific Self-Cleavage Reaction Performed by a Novel RNA in Neurospora Mitochondria, *Cell* (May 18, 1990), 61:685-696.

Guerrier-Takada, C. et al., The RNA Moiety of Ribonuclease P is the Catalytic Subunit of the Enzyme, *Cell* (Dec. 1983), 35:849-857.

Hampel, A. et al., "Hairpin" Catalytic RNA Model: Evidence for Helices and Sequence Requirement for Substrate RNA, *Nuc. Acids Res.* (1990), 18: 299-304.

Hampel, A. and R. Tritz, RNA Catalytic Properties of the Minimum (-)sTRSV Sequence, *Biochemistry* (1989), 28: 4929-4933.

Rossi, J.J. et al., Ribozymes as a Anti-HIV-1 Therapeutic Agents: Principles, Applications, and Problems, *AIDS Research and Human Retroviruses* (1992), 8: 183-189.

Collins, R.A. and J.E. Olive, Reaction Conditions and Kinetics of Self-Cleavage of a Ribozyme Derived from *Neurospora* VS RNA, *Biochemistry* (1993), 32: 2795-2799.

Felgner, P.L. et al., Lipofection: A Highly Efficient, Lipid-Mediated DNA-Transfection Procedure, *Proc. Natl. Acad. Sci. USA* (Nov. 1987), 84: 7413-7417.

Machy, P. et al., Gene Transfer from Targeted Liposomes to Specific Lymphoid Cells by Electroporation, *Proc. Natl. Acad. Sci. USA* (Nov. 1988), 85: 8027-31.

Ulmer, J.B. et al., Heterologous Protection Against Influenza by Injection of DNA Encoding a Viral Protein, *Science* (Mar. 19, 1993), 259: 1745-1749.

Wu, G.Y. and C.H. Wu Receptor-mediated Gene Delivery and Expression in Vivo, *J. of Biol. Chem.* (Oct. 15, 1988), 263: 14621-14624.

Williams, R.S. et al., Introduction of Foreign Genes into Tissues of Living Mice by DNA-Coated Microprojectiles, *Proc. Natl. Acad. Sci. USA* (Apr. 1991), 88: 2726-2730.

Wu., G.Y. and C.H. Wu, Receptor-Mediated in Vitro Gene Transformation by a Soluble DNA Carrier System, *J. of Biol. Chem.* (Apr. 5, 1987), 262: 4429-4432.

Curiel, D.T., High-Efficiency Gene Transfer Mediated by Adenovirus Coupled to DNA-Polylysine Complexes, *Human Gene Therapy* (1992), 3: 147-154.

Amann, E. et al., Tightly Regulated tac Promoter Vectors Useful for the Expression on Unfused and Fused proteins in *Escherichia Coli, Gene* (1988), 69: 301-315.

Wilson, J.M. et al., Hepatocyte-directed Gene Transfer in Vivo Leads to Transient Improvement of Hypercholesterolemia in Low Density Lipoprotein Receptor-deficient Rabbits, *J. Biol. Chem.* (1992) 267: 963-967.

Felgner, P.L. and G.M. Ringold, Cationic Liposome-Mediated Transfection, *Nature* (1989), 337: 387-388.

Mark, G.E. and E.A. Padlan, Humanization of Monoclonal Antibodies, in *The Handbook of Experimental Pharmacology*, vol. 113, New York: Springer-Verlag, 1994: 105-134.

Chowers, Y. et al., The Vδ1 T Cell Receptor Repertoire in Human Small Intestine and Colon, *Gene* (1994), 180: 183-190.

Wittenauer, L.A., Hydrolysis of a Fluorescent Phospholipid Substrate by Phospholipase $A_2$ and Lipoprotein Lipase, *Biochem. Biophys. Res. Comm.* (1984), 118: 894-901.

Reynolds, L.J., Assay Strategies and Methods for Phospholipases, *Methods in Enzymol.* (1991), 197: 3-23.

Yu, L. and E.A. Dennis, Thio-Based Phospholipase Assay, *Methods in Enzymol.* (1991), 197: 65-75.

Ishizaki, K. et al., The Biochemical Studies on Phalloidin-Induced Cholestatsis in Rats, *Toxicol. Lett.* (1997), 90: 29-34.

Carlton, V.E.H. et al., Mapping of a Locus for Progressive Familial Intrahepatic Cholestasis (Byler Disease) to 18q21-q22, the Benign Recurrent Intrahepatic Cholestasis Region, *Hum. Mol. Genet.* (1995), 4: 1049-1053.

Houwen, R.H.J. et al., Genome Screening by Searching for Shared Segments: Mapping a Gene for Benign Recurrent Intrahepatic Cholestasis, *Nature Genet.* (Dec. 1994), 8: 380-386.

Strautnieks, S.S. et al., Locus Heterogeneity in Progessive Familial Intrahepatic Cholestasis, *J. Med. Genet.* (1996), 33: 833-836.

Smith, P.K. et al., Measurement of Protein Using Bicinchoninic Acid, *Anal.n Biochem.* (1985), 150: 76-85.

Schuh, J. et al., Oxygen-Mediated Heterogeneity of apo-Low-Density Lipoprotein, *Proc. Natl. Acad. Sci. USA* (1978), 75: 3173-3177.

Liang, P. and A.B. Pardee, Differential Display of Eukaryotic Messenger RNA by Means of the Polymerase Chain Reaction, *Science* (Aug. 14, 1992), 257: 967-971.

Frohman, M.A. et al., Rapid Production of Full-length cDNAs from Rare Transcripts: Amplification using a Single Gene-Specific Oligonucleotide Primer, *Proc. Natl. Acad. Sci. USA* (Dec. 1988), 85: 8998-9002.

Loh, E.Y. et al., Polymerase Chain Reaction with Single-Sided Specificity: Analysis of T Cell Receptor δ Chain, *Science* (Jan. 13, 1989), 243: 217-220.

Mead, D.A. et al., A Universal Method for the Direct Cloning of PCR Amplified Nucleic Acid, *Biotechnology* (Jul. 1991), 9: 657-663.

Chomczynski, P., A Reagent for the Single-Step Simultaneous Isolation of RNA, DNA and Protein from Cell and Tissue Samples, *BioTechniques* (1993), 15: 532-536.

Simms, D. et al., A Novel Spin Cartridge for the Rapid Purification of Small Amounts of DNA, *Focus,* 13: 99-100.

Walter, P. et al., Protein Translocation Across the Endoplasmic Reticulum, *Cell* (Aug. 1984), 38: 5-8.

Sternberg, N. et al., Generation of a 50,000-Member Human DNA Library with an Average DNA Insert Size of 75-100 kbp in a Bacteriophage P1 Cloning Vector, *The New Biologist* (Feb. 1990), 2: 151-162.

Camps, L. et al., Lipoprotein Lipase: Cellular Origin and Functional Distribution, *Am J. Physiol.* (1990), 258: C673-C681.

Higgins, D.G. and P.M. Sharp, CLUSTAL: A Package for Performing Multiple Sequence Alignment on a Microcomputer, *Gene* (1988), 73: 237-244.

Semenkovich, C.F. et al., Lipoprotein Lipase and Hepatic Lipase mRNA Tissue Specific Expression, Developmental Regulation, and Evolution, *J. Lipid Res.* (1989), 30: 423-431.

Adams, M.D. et al., 3,400 New Expressed Sequence Tags Identify Diversity of Transcripts in Human Brain, *Nature Genet.* (Jul. 1993), 4: 256-267.

Chen, L. and R. Morin, Purification of a Human Placental Cholesteryl Ester Hydrolase, *Biochim. Biophys. Acta* (1971), 231: 194-197.

Verhoeven, A.J.M. et al., Hepatic Lipase Gene is Transcribed in Rat Adrenals into a Truncated mRNA, *J. Lipid Res.* (1994), 35: 966-975.

Verhoeven, A.J.M. and H. Jansen, Hepatic Lipase mRNA is Expressed in Rat and Human Steroidogenic Organs, *Biochim. Biophys. Acta* (1994), 1211: 121-124.

Burton, B.K. and H.W. Mueller, Purification and Properties of Human Placental Acid Lipase, *Biochim. Biophys. Acta* (1980), 618: 449-460.

Maciag, T. et al., An Endothelial Cell Growth Factor From Bovine Hypothalamus: Identification and Partial Characterization, *Proc. Natl. Acad. Sci. USA* (Nov. 1979), 76: 5674-5678.

Rothwell, J.E. and M.C. Elphick, Lipoprotein Lipase Activity in Human and Guinea-pig Placenta, *J. Dev. Physiol.* (1982), 4: 153-159.

Wang, C. and J.A. Hartsuck, Bile Salt-Activated Lipase. A Multiple Function Lipolytic Enxyme, *Biochim. Biophys. Acta* (1993), 1166:1-19.

Jameson, B.A. and H. Wolf, The Antigenic Index: A Novel Algorithm for Predicting Antigenic Determinants, *Comput. Applic. in the Biosciences* (Mar. 1988), 4: 181-186.

Tremp, G.L. et al., A 700-bp Fragment of the Human Antithrombin III Promoter is Sufficient to Confer High, Tissue-Specific Expression on Human Apolipoprotein A-11 in Transgenic Mice, *Gene* (1995), 156: 199-205.

Tsukamoto, K. et al., Liver-directed Gene Transfer and Prolonged Expression of Three Major Human ApoE Isoforms in ApoE-deficient Mice, *J. Clin. Invest.* (Jul. 1997), 100:107-114.

Tsukamoto, K et al., Comparison of Human apoA-1 Expression in Mouse Models of Atherosclerosis After Gene Transfer Using a Second Generation Adenovirus, *J. Lipid Res.* (1997), 38: 1869-1876.

US 5,891,715, 04/1999, Haddada et al. (withdrawn)

* cited by examiner

*Primary Examiner*—Nashaat T. Nashed
*Assistant Examiner*—William W. Moore
(74) *Attorney, Agent, or Firm*—Synnestvedt & Lechner LLP

(57) ABSTRACT

The present invention relates to compositions for use in raising or lowering the level of LIPG polypeptide in a patient. Embodiments of the composition include compositions comprising: an anti-sense nucleic acid; a neutralizing antibody; an intracellular binding protein; an inhibitor which inhibits the enzymatic activity of LIPG polypeptide; an inhibitor which inhibits the expression of LIPG gene; a ribozyme; an LIPG polypeptide; an enhancer which increases the enzymatic activity of LIPG polypeptide; or an enhancer which increases the expression of LIPG gene. The invention relates also to methods for using the above compositions.

In addition, the invention relates to a method for diagnosing a predisposition to lower cholesterol, a method for determining whether a test compound can inhibit the enzymatic reaction between LIPG polypeptide and HDL cholesterol, and methods for determining whether a test compound can enhance the enzymatic reaction between LIPG polypeptide and LDL or VLDL cholesterol.

2 Claims, 18 Drawing Sheets

MSNSVPLLCFWSLCYCFAAGSPVPFGPEGRLEDKLHKPKATQTEVKPSVRFNLRTSKDPEHEGCYL
SVGHSQPLEDCSFNMTAKTFFIIHGWTMSGIFENWLHKLVSALHTREKDANVVVVDWLPLAHQLY
TDAVNNTRVVGHSIARMLDWLQEKDDFSLGNVHLIGYSLGAHVAGYAGNFVKGTVGRITGLDPA
GPMFEGADIHKRLSPDDADFVDVLHTYTRSFGLSIGIQMPVGHIDIYPNGGDFQPGCGLNDVLGSIA
YGTTEVVKCEHERAVHLFVDSLVNQDKPSFAFQCTDSNRFKKGICLSCRKNRCNSIGYNAKKMR
NKRNSKMYLKTRAGMPFRVYHYQMKIHVFSYKNMGEIEPTFYVTLYGTNADSQTLPLEIVERIEQ
NATNTFLVYTEEDLGDLLKIQLTWEGASQSWYNLWKEFRSYLSQPRNPGRELNIRRIRVKSGETQR
KLTFCTEDPENTSISPGRELWFRKCRDGWRMKNETSPTVELP

GPEGRLEDKLHKPKATC

COMPOSITIONS AND METHODS FOR EFFECTING THE LEVELS OF HIGH DENSITY LIPOPROTEIN (HDL) CHOLESTEROL AND APOLIPOPROTEIN AI VERY LOW DENSITY LIPOPROTEIN (VLDL) CHOLESTEROL AND LOW DENSITY LIPOPROTEIN (LDL) CHOLESTEROL

This application is a continuation-in-part of U.S. application Ser. No. 08/985,492, filed Dec. 5, 1997, now U.S. Pat. No. 6,395,530, which claims the benefit of provisional applications under 35 U.S.C. § 119(e), 60/032,254 and 60/032,783, both of which were filed Dec. 6, 1996, the disclosures of which are incorporated herein by reference in their entirety.

FIELD OF THE INVENTION

This invention relates to methods and compositions for increasing the level of high density lipoprotein (HDL) cholesterol and apolipoprotein AI in a patient and to methods and compositions for lowering the levels of very low density lipoprotein (VLDL) cholesterol, and low density lipoprotein (LDL) cholesterol in a patient. The invention includes within its scope methods and compositions which lower the expression of, or inhibit the activity of, a gene, LIPG, which encodes a lipase enzyme that lowers the levels of HDL cholesterol and apolipoprotein AI. The invention additionally includes within its scope methods and compositions to increase the expression of, or enhance the activity of, the lipase enzyme, resulting in lower levels of VLDL and LDL cholesterol.

Lipids

Lipids are water-insoluble organic biomolecules, which are essential components of diverse biological functions, including the storage, transport, and metabolism of energy, and membrane structure and fluidity. Lipids are derived from two sources in man and other animals: some lipids are ingested as dietary fats and oils and other lipids are biosynthesized by the human or animal. In mammals, at least 10% of the body weight is lipid, the bulk of which is in the form of triacylglycerols.

Triacylglycerols, also known as triglycerides and triacylglycerides, are made up of three fatty acids esterified to glycerol. Dietary triacylglycerols are stored in adipose tissues as a source of energy, or hydrolyzed in the digestive tract by triacylglycerol lipases, the most important of which is pancreatic lipase. Triacylglycerols are transported between tissues in the form of lipoproteins.

Lipoproteins are micelle-like assemblies found in plasma which contain varying proportions of different types of lipids and proteins (called apoproteins). There are five main classes of plasma lipoproteins, the major function of which is lipid transport. These classes are, in order of increasing density: chylomicrons; very low density lipoproteins (VLDL); intermediate-density lipoproteins (IDL); low density lipoproteins (LDL); and high density lipoproteins (HDL). Although many types of lipid are found associated with each lipoprotein class, each class transports predominantly one type of lipid: triacylglycerols described above are transported in chylomicrons, VLDL, and IDL; whereas phospholipids and cholesterol esters are transported in HDL and LDL respectively.

Phospholipids are di-fatty acid esters of glycerol phosphate which contain a polar group coupled to the phosphate. Phospholipids are important structural components of cellular membranes. Phospholipids are hydrolyzed by enzymes called phospholipases. Phosphatidylcholine, an exemplary phospholipid, is a major component of most eukaryotic cell membranes.

Cholesterol is the metabolic precursor of steroid hormones and bile acids as well as an essential constituent of cell membranes. In man and other animals, cholesterol is ingested in the diet and is synthesized also by the liver and other tissues. Dietary cholesterol is transported from the intestine to the liver by large lipoprotein molecules in the blood. The liver secretes Very Low Density Lipoprotein (VLDL) which transports cholesterol and cholesterol ester and various other compounds into the bloodstream. VLDL is partially converted in adipose tissue to Low Density Lipoprotein (LDL). LDL transports both free and esterified cholesterol to body tissues. High Density Lipoprotein (HDL) transports cholesterol to the liver to be broken down and excreted.

Membranes surround every living cell and serve as a barrier between the intracellular and extracellular compartments. Membranes also enclose the eukaryotic nucleus, make up the endoplasmic reticulum, and serve specialized functions such as in the myelin sheath that surrounds axons. A typical membrane contains about 40% lipid and 60% protein, but there is considerable variation. The major lipid components are phospholipids, specifically phosphatidylcholine and phosphatidylethanolamine, and cholesterol. The physicochemical properties of membranes, such as fluidity, can be changed by modification of either the fatty acid profiles of the phospholipids or the cholesterol content. Modulating the composition and organization of membrane lipids also modulates membrane-dependent cellular functions, such as receptor activity, endocytosis, and cholesterol flux.

Enzymes

The triacylglycerol lipases are a family of enzymes which play several pivotal roles in the metabolism of lipids in the body. Three members of the human triacylglycerol lipase family have been described: pancreatic lipase, lipoprotein lipase, and hepatic lipase (Goldberg, I. J., Le, N.-A., Ginsberg, H. N., Krauss, R. M., and Lindgren, F. T. (1988) *J. Clin. Invest.* 81, 561–568; Goldberg, I. J., Le, N., Paterniti J. R., Ginsberg, H. N., Lindgren, F. T., and Brown, W. V. (1982) *J. Clin. Invest.* 70, 1184–1192; Hide, W. A., Chan, L., and Li, W.-H. (1992) *J. Lipid. Res.* 33, 167–178). Pancreatic lipase is primarily responsible for the hydrolysis of dietary lipids. Variants of pancreatic lipase have been described, but their physiological role has not been determined (Giller, T., Buchwald, P., Blum-Kaelin, D., and Hunziker, W. (1992) *J. Biol. Chem.* 267, 16509–16516). Lipoprotein lipase is the major enzyme responsible for the distribution and utilization of triglycerides in the body. Lipoprotein lipase hydrolyzes triglycerides in both chylomicrons and VLDL. Hepatic lipase hydrolyzes triglycerides in IDL and HDL and is responsible for lipoprotein remodeling. Hepatic lipase also functions as a phospholipase and hydrolyzes phospholipids in HDL.

Phospholipases play important roles in the catabolism and remodeling of the phospholipid component of lipoproteins and the phospholipids of membranes. Phospholipases also play a role in the release of arachidonic acid and the subsequent formation of prostaglandins, leukotrienes, and other lipids which are involved in a variety of inflammatory processes.

The aforementioned lipases are approximately 450 amino acids in length and have leader signal peptides to facilitate secretion. The lipases are comprised of two principal domains (Winkler, K., D'Arcy, A., and Hunziker, W. (1990) *Nature* 343, 771–774). The amino terminal domain contains the catalytic site while the carboxyl domain is believed to be responsible for substrate binding, cofactor association, and interaction with cell receptors (Wong, H., Davis, R. C., Nikazy, J., Seebart, K. E., and Schotz, M. C. (1991) *Proc. Natl. Acad. Sci. USA* 88, 11290–11294; van Tilbeurgh, H., Roussel, A., Lalouel, J.-M., and Cambillau, C. (1994) *J. Biol. Chem.* 269, 4626–4633; Wong, H., Davis, R. C., Thuren, T., Goers, J. W., Nikazy, J., Waite, M., and Schotz, M. C. (1994) *J. Biol. Chem.* 269, 10319–10323; Chappell, D. A., Inoue, I., Fry, G. L., Pladet, M. W., Bowen, S. L., Iverius, P.-H., Lalouel, J.-M., and Strickland, D. K. (1994) *J. Biol. Chem.* 269, 18001–18006). The overall level of amino acid homology between members of the family is 22–65%, with local regions of high homology corresponding to structural homologies which are linked to enzymatic function.

The naturally occurring lipoprotein lipase is glycosylated. Glycosylation is necessary for LPL enzymatic activity (Semenkovich, C. F., Luo, C.-C., Nakanishi, M. K., Chen, S.-H., Smith, L C., and Chan L. (1990) *J. Biol. Chem.* 265, 5429–5433). There are two sites for N-linked glycosylation in hepatic and lipoprotein lipase and one in pancreatic lipase. Additionally, four sets of cysteines form disulfide bridges which are essential in maintaining structural integrity for enzymatic activity (Lo, J.-Y., Smith, L. C., and Chan, L. (1995) *Biochem. Biophys. Res. Commun.* 206, 266–271; Brady, L., Brzozowski, A. M., Derewenda, Z. S., Dodson, E., Dodson G., Tolley, S., Turkenburg, J. P., Christiansen, L., Huge-Jensen B., Norskov, L., Thim, L., and Menge, U. (1990) *Nature* 343, 767–770).

Members of the triacylglycerol lipase family share a number of conserved structural features. One such feature is the "GXSXG" motif, in which the central serine residue is one of the three residues comprising the "catalytic triad" (Winkler, K., D'Arcy, A., and Hunziker, W. (1990) *Nature* 343, 771–774; Faustinella, F., Smith, L. C., and Chan, L. (1992) *Biochemistry* 31, 7219–7223). Conserved aspartate and histidine residues make up the balance of the catalytic triad. A short span of 19–23 amino acids (the "lid region") forms an amphipathic helix structure and covers the catalytic pocket of the enzyme (Winkler, K., D'Arcy, A., and Hunziker, W. (1990) *Nature* 343, 771–774). This region diverges significantly between members of the family. It has been determined recently that the span confers substrate specificity to the enzymes (Dugi, K. A., Dichek H. L., and Santamarina-Fojo, S. (1995) *J. Biol. Chem.* 270, 25396–25401). Comparisons between hepatic and lipoprotein lipase have demonstrated that differences in triacylglycerol lipase and phospholipase activities of the enzymes are in part mediated by this lid region (Dugi, K. A., Dichek H. L., and Santamarina-Fojo, S. (1995) *J. Biol. Chem.* 270, 25396–25401).

The triacylglycerol lipases possess varying degrees of heparin binding activity. Lipoprotein lipase has the highest affinity for heparin. This binding activity has been mapped to stretches of positively charged residues in the amino terminal domain (Ma, Y., Henderson, H. E., Liu, M.-S., Zhang, H., Forsythe, I. J., Clarke-Lewis, I., Hayden, M. R., and Brunzell, J. D. *J. Lipid Res.* 35, 2049–2059). The localization of lipoprotein lipase to the endothelial surface (Cheng, C. F., Oosta, G. M., Bensadoun, A., and Rosenberg, R. D. (1981) *J. Biol. Chem.* 256, 12893–12896) is mediated primarily through binding to surface proteoglycans (Shimada K., Gill, P. J., Silbert, J. E., Douglas, W. H. J., and Fanburg, B. L. (1981) *J. Clin. Invest.* 68, 995–1002; Saxena, U., Klein, M. G., and Goldberg, I. J. (1991) *J. Biol. Chem.* 266, 17516–17521; Eisenberg, S., Sehayek, E., Olivecrona, T., and Vlodavsky, I. (1992) *J. Clin Invest.* 90, 2013–2021). It is this binding activity which allows the enzyme to accelerate LDL uptake by acting as a bridge between LDL and the cell surface (Mulder, M., Lombardi, P., Jansen, H., vanBerkel T. J., Frants R. R., and Havekes, L. M. (1992) *Biochem. Biophys. Res. Comm.* 185, 582–587; Rutledge, J. C., and Goldberg, I. J., (1994) *J. Lipid Res.* 35. 1152–1160; Tsuchiya, S., Yamabe, M., Yamaguchi, T., Kobayashi, Y., Konno, T., and Tada, K. (1980) *Int. J. Cancer* 26, 171–176).

Lipoprotein lipase and pancreatic lipase are both known to function in conjunction with co-activator proteins: apolipoprotein CII for lipoprotein lipase; and colipase for pancreatic lipase.

The genetic sequences encoding human pancreatic lipase, hepatic lipase and lipoprotein lipase have been reported (Genbank accession #M93285, #J03540, and #M15856 respectively). The messenger RNAs of human hepatic lipase and pancreatic lipase are approximately 1.7 and 1.8 kilobases in length respectively. Two mRNA transcripts of 3.6 and 3.2 kilobases are produced from the human lipoprotein lipase gene. These two transcripts utilize alternate polyadenylation signals and differ in their translational efficiency (Ranganathan, G., Ong, J. M., Yukht, A., Saghizadeh, M., Simsolo, R. B., Pauer, A., and Kern, P. A. (1995) *J. Biol. Chem.* 270, 7149–7155).

Physiological Processes

The metabolism of lipids involves the interaction of lipids, apoproteins, lipoproteins, and enzymes.

Hepatic lipase and lipoprotein lipase are multifunctional proteins which mediate the binding, uptake, catabolism, and remodeling of lipoproteins and phospholipids. Lipoprotein lipase and hepatic lipase function while bound to the luminal surface of endothelial cells in peripheral tissues and the liver respectively. Both enzymes participate in reverse cholesterol transport, which is the movement of cholesterol from peripheral tissues to the liver either for excretion from the body or for recycling. Genetic defects in both hepatic lipase and lipoprotein lipase are known to be the cause of familial disorders of lipoprotein metabolism. Defects in the metabolism of lipoproteins result in serious metabolic disorders, including hypercholesterolemia, hyperlipidemia, and atherosclerosis.

REPORTED DEVELOPMENTS

Atherosclerosis is a complex, polygenic disease which is defined in histological terms by deposits (lipid or fibrolipid plaques) of lipids and of other blood derivatives in blood vessel walls, especially the large arteries (aorta, coronary arteries, carotid). These plaques, which are more or less calcified according to the degree of progression of the atherosclerotic process, may be coupled with lesions and are associated with the accumulation in the vessels of fatty deposits consisting essentially of cholesterol esters. These plaques are accompanied by a thickening of the vessel wall, hypertrophy of the smooth muscle, appearance of foam cells (lipid-laden cells resulting from uncontrolled uptake of cholesterol by recruited macrophages) and accumulation of fibrous tissue. The atheromatous plaque protrudes markedly from the wall, endowing it with a stenosing character responsible for vascular occlusions by atheroma, thrombosis or embolism, which occur in those patients who are most affected. These lesions can lead to serious cardiovascular pathologies such as infarction, sudden death, cardiac insufficiency, and stroke.

High Density Lipoprotein (HDL) Cholesterol Levels and Atherosclerotic Diseases

High density lipoprotein (HDL) cholesterol levels are inversely associated with risk of atherosclerotic cardiovascular disease (Gordon et al., *N. Engl. J. Med.*, 321, 1311–1316 (1989)). At least 50% of the variation in HDL cholesterol levels is genetically determined (Breslow, J. L., *The Metabolic Basis of Inhereited Disease*, 2031–2052, McGraw-Hill, New York (1995); Heller et al., *N. Engl. J. Med.*, 328, 1150–1156 (1993)), but the genes responsible for variation in HDL levels have not been fully elucidated. Lipoprotein lipase (LPL) and hepatic lipase (HL), two members of the triacylglycerol (TG) lipase family, both influence HDL metabolism (Breslow, supra; Murthy et al., *Pharmacol. Ther.*, 70, 101–135 (1996); Goldberg, J. I., *J. Lipid Res.*, 37, 693–707 (1996); Bensadoun et al., *Curr. Opin. Lipidol.*, 7, 77–81 (1996) and the HL (LIPC) locus has been associated with variation in HDL cholesterol levels in humans (Cohen et al., *J. Clin. Invest.*, 94, 2377–2384 (1994); Guerra et al., *Proc. Natl. Acad. Sci. USA*, 94, 4532–4537 (1997)). The normal range for HDL cholesterol is about 35 to 65 mg/dL, and the HDL level should account for more than 25% of the total cholesterol.

Very Low Density Lipoprotein (VLDL) and Low Density Lipoprotein (LDL) Cholesterol Levels and Atherosclerotic Diseases High levels of circulating LDL and VLDL cholesterol are associated with increased risk of atherosclerosis.

VLDL are the precursors of LDL. Therapeutic agents that lower plasma VLDL and LDL cholesterol levels are highly desirable because of the known strong association between these lipid parameters and coronary heart disease.

Epidemiologic studies have demonstrated a strong relationship between elevated LDL cholesterol and coronary heart disease (CHD) and other atherosclerotic vascular diseases (Kannell, W. B., *Am. J. Cardiol.*, 76, 69C–77C (1995)). Three major secondary prevention trials performed with statins have demonstrated that reduction of LDL cholesterol levels result in significant reduction in CHD events and total mortality (Scandinavian Simvastatin Survival Study Group, Lancet, 344, 1383–1389 (1994); Sacks et al., *N. Engl. J. Med.*, 335, 1001–1009 (1996); Tonkin et al., *N. Engl. J. Med.*, 339, 1349–1357 (1998); Grundy, S. M., Editorial, 1436–1439 (1998)). Two large primary prevention trials with statins have also demonstrated significant benefit of LDL cholesterol reduction with statins in reducing cardiovascular events (Grundy, supra; Shepherd et al., *N. Engl. J. Med.*, 333, 1301–1307 (1995); Downs et al., *JAMA*, 279, 1615–1622 (1998)). However, current therapies do not adequately reduce LDL cholesterol levels in all persons. VLDL cholesterol levels have also been recognized to be associated with increased risk of CHD (Kannel, supra). Current therapies do not have as much effect in reducing VLDL cholesterol as LDL cholesterol. Therefore, new approaches to reducing both LDL cholesterol and VLDL cholesterol are still needed.

Ideally, the range for VLDL cholesterol is about 1 to 30 mg/dL and the range for LDL cholesterol is about 60 to 160 mg/dL. The LDL to HDL ratio is ideally less than 3.5.

The Role of Triacylglycerol Lipases in Atherosclerotic Diseases

The role of triacylglycerol lipases in vascular pathologies such as atherosclerosis has been an area of intense study (reviewed in Olivecrona, G., and Olivecrona, T. (1.995) *Curr. Opin. Lipid.* 6, 291–305). Generally, the action of the lipoprotein lipase is believed to be antiatherogenic because this enzyme lowers serum triacylglycerol levels and promote HDL formation. Transgenic animals expressing human lipoprotein lipase have decreased levels of plasma triglycerides and an increased level of high density lipoprotein (HDL) (Shimada, M., Shimano, H., Gotoda, T., Yamamoto, K., Kawamura, M., Inaba, T., Yazaki, t., and Yamada, N. (1993) *J. Biol. Chem.* 268, 17924–17929; Liu, M.-S., Jirik, F. R., LeBoeuf, R. C., Henderson, H., Castellani, L. W., Lusis, A. J., ma, Y., Forsythe, I. J., Zhang, H., Kirk, E., Brunzell, J. D., and Hayden, M. R. (1994) *J. Biol. Chem.* 269, 11417–11424). Humans with genetic defects resulting in decreased levels of lipoprotein lipase activity have been found to have hypertriglyceridemia, but no increased risk of coronary heart disease. This is reported to be due to the lack of production of intermediate-sized, atherogenic lipoproteins which could accumulate within the subendothelial space (Zilversmit, D. B. (1973) *Circ. Res.* 33, 633–638).

In contrast to lipoprotein lipase (LPL), the physiologic function of HL appears to be related to the metabolism of lipoprotein remnants and HDL (Bensadoun et al., *Curr. Opin. Lipidol.*, 7, 77–81 (1996)). Genetic deficiency of HL is associated with modestly increased levels of remnants and HDL cholesterol in humans (Hegele et al., *Arterioscler. Thromb.*, 13, 720–728 (1993)) and mutant mice (Homanics et al., *J. Biol. Chem.*, 270, 2974–2980 (1995)). Despite increased plasma cholesterol levels, HL deficiency is associated with reduced atherosclerosis in apoE mutant mice (Mezdour et al., *J. Biol. Chem.*, 272, 13570–13575 (1997)). Transgenic animals overexpressing HL have decreased HDL (Busch et al., *J. Biol. Chem.*, 269, 16376–16382 (1994); Fan et al., *Proc. Natl. Acad. Sci. USA*, 91, 8724–8728 (1994)). Increased HL activity in humans is associated with low HDL cholesterol. The HL locus on chromosome 15q21 has been associated with variation in plasma HDL cholesterol levels in humans (Cohen et al., *J. Clin. Invest.*, 94, 2377–2384 (1994); Guerra et al., *Proc. Natl. Acad. Sci. USA*, 94 4532–4537 (1997)), but accounts for only a portion of the genetic contribution to variation in HDL cholesterol levels. There is at least one major locus influencing HDL cholesterol levels in humans that is distinct from the HL locus (Mahaney et al., *Arterioscler. Thromb. Vasc. Biol.*, 15, 1730–1739 (1995)).

In the localized area of an atherosclerotic lesion, the increased level of lipase activity is hypothesized to accelerate the atherogenic process (Zilversmit, D. B. (1995) *Clin. Chem.* 41, 153–158; Zambon, A., Torres, A., Bijvoet, S., Gagne, C., Moojani, S., Lupien, P. J., Hayden M. R., and Brunzell, J. D. (1993) *Lancet* 341, 1119–1121). This may be due to an increase in the binding and uptake of lipoproteins by vascular tissue mediated by lipases (Eisenberg, S., Sehayek, E., Olivecrona, T. Vlodavsky, I. (1992) *J. Clin. Invest.* 90, 2013–2021; Tabas, I., Li, I., Brocia R. W., Xu, S. W., Swenson T. L. Williams, K. J. (1993) *J. Biol. Chem.* 268, 20419–20432; Nordestgaard, B. G., and Nielsen, A. G. (1994) *Curr. Opin. Lipid.* 5, 252–257; Williams, K. J., and Tabas, I. (1995) *Art. Thromb. and Vasc. Biol.* 15, 551–561). Additionally, a high local level of lipase activity may result in cytotoxic levels of fatty acids and lysophosphatidylcholine being produced in precursors of atherosclerotic lesions.

Despite the understanding that has evolved regarding the role of lipase enzyme activity in regulating the levels of lipids and the various plasma lipoproteins, there is a need to identify and develop therapies which can increase the levels of HDL cholesterol, as well as lower the levels of VLDL and LDL cholesterol to reduce the risk of developing atherosclerotic cardiovascular diseases.

SUMMARY OF THE INVENTION

In accordance with the present invention, there is provided a composition for lowering the expression of the LIPG gene in a patient comprising an antisense nucleic acid, including for example, an expression vector which includes said antisense nucleic acid. Examples of preferred expression vectors are retroviral vectors, adenoviral vectors, adeno-associated viral vectors, herpesviral vectors, and naked DNA vectors. The antisense nucleic acid can be, for example, an oligonucleotide which contains chemically modified bases.

Another aspect of the present invention is the provision of a composition for lowering the enzymatic activity of the LIPG polypeptide in a patient comprising a neutralizing antibody capable of binding to the LIPG polypeptide and lowering its enzymatic activity, including, for example, an expression vector which includes a DNA sequence encoding said antibody. Examples of preferred expression vectors are retroviral vectors, adenoviral vectors, adeno-associated viral vectors, herpesviral vectors, and naked DNA vectors.

Still another aspect of the present invention is the provision of a composition for lowering the enzymatic activity of the LIPG polypeptide in a patient comprising an intracellular binding protein, including, for example, an expression vector which includes a DNA sequence encoding said intracellular binding protein. Examples of preferred expression vectors are retroviral vectors, adenoviral vectors, adeno-associated viral vectors, herpesviral vectors, and naked DNA vectors.

Yet other aspects of the present invention are the provision of: (A) a composition which comprises an inhibitor that is capable of inhibiting the enzymatic activity of the LIPG polypeptide in a patient; (B) a composition which comprises an inhibitor that is capable of lowering the expression of the LIPG gene in a patient; and (C) a composition which is capable of lowering the expression of LIPG in a patient and which comprises a ribozyme, including, for example, an expression vector which includes a DNA sequence encoding said ribozyme. Examples of preferred expression vectors are retroviral vectors, adenoviral vectors, adeno-associated viral vectors, herpesviral vectors, and naked DNA vectors. A preferred ribozyme is a hammerhead ribozyme.

The present invention provides also: (D) a composition which increases the level of LIPG polypeptide in a patient and which comprises an expression vector that includes a DNA sequence encoding the LIPG polypeptide or an enhancer that is capable of increasing the expression of the LIPG gene; and (E) a composition which increases the enzymatic activity of LIPG polypeptide in a patient which comprises an enhancer that binds to and enhances the enzymatic activity of the LIPG polypeptide.

In addition, the present invention provides a method for raising the level of high density lipoprotein (HDL) cholesterol and apolipoprotein AI in a patient by administering to the patient a composition which lowers the enzymatic activity of LIPG in said patient, for example, by lowering the level of LIPG polypeptide in the patient. In preferred form, the method involves the use of a composition which comprises an antisense nucleic acid, particularly one that is modified to increase the chemical stability of the nucleic acid. The aforementioned method can be practiced also by use of a composition which comprises a neutralizing antibody capable of binding to the LIPG polypeptide and lowering its enzymatic activity or a composition which comprises an inhibitor which inhibits the enzymatic activity of LIPG polypeptide, for example, a compound which lowers the expression of the LIPG gene or a composition which comprises a ribozyme that cleaves mRNA encoding LIPG, or a composition which comprises a DNA molecule and a liposome, for example, a cationic liposome.

In preferred form, the aforementioned method comprises also the administration of a composition which is capable of expressing apolipoprotein AI in said patient.

Another aspect of the present invention is the provision of a method for lowering the level of very low density lipoprotein (VLDL) cholesterol in a patient by administering to the patient a composition which is capable of increasing the enzymatic activity of LIPG in said patient, for example, by use of a composition which comprises an LIPG polypeptide and a pharmaceutically acceptable carrier and which includes preferably an expression vector that is capable of expressing an LIPG polypeptide, preferably a retroviral vector, an adenoviral vector, or an adeno-associated viral vector. The aforementioned method can be practiced by use of a composition which comprises an enhancer that enhances the enzymatic activity of LIPG polypeptide or an enhancer that increases expression of the LIPG gene.

Still another aspect of the present invention is the provision of a method for lowering the level of low density lipoprotein (LDL) cholesterol in a patient by administering to the patient a composition which is capable of increasing the enzymatic activity of LIPG in the patient, preferably by use of an LIPG polypeptide, for example, by use of an expression vector that is capable of expressing the LIPG polypeptide, preferably by use of a retroviral vector, an adenoviral vector, or an adeno-associated viral vector. The aforementioned method includes preferably the use of a composition which comprises an enhancer that enhances the enzymatic activity of LIPG polypeptide or an enhancer which increases the expression of the LIPG gene.

The present invention provides also a method for lowering the level of LDL cholesterol in a patient by administering to the patient an enhancer which preferentially enhances the enzymatic reactions between LIPG polypeptide and LDL cholesterol relative to the enzymatic reactions between LIPG polypeptide and HDL cholesterol and apolipoprotein AI.

In addition, the present invention provides a method for lowering the level of VLDL cholesterol in a patient by administering to the patient an enhancer which preferentially enhances the enzymatic reactions between LIPG polypeptide and VLDL cholesterol relative to the enzymatic reactions between LIPG polypeptide and HDL cholesterol and apolipoprotein AI.

Still another aspect of the present invention is the provision of a method for diagnosing a predisposition to low HDL cholesterol and apolipoprotein AI levels by obtaining a tissue sample from a patient and measuring the level of LIPG polypeptide in the sample, for example, by use of blood tissue and the use of an immunoassay for measurement. In another aspect of the present invention, the levels of LIPG polypeptide are measured by measuring the levels of LIPG mRNA.

An additional aspect of the present invention is the provision of a method for determining whether a test compound can inhibit the enzymatic reaction between the LIPG polypeptide and HDL cholesterol and apolipoprotein AI comprising: (A) comparing the level of HDL cholesterol and apolipoprotein AI in a first sample comprising: (1) HDL cholesterol and apolipoprotein AI, (2) LIPG polypeptide, and (3) the test compound with the level of HDL cholesterol and apolipoprotein AI in another sample comprising: (4) HDL cholesterol and apolipoprotein AI, and (5) LIPG polypeptide; and (B) identifying whether or not the test compound is effective in inhibiting the enzymatic reaction between the LIPG polypeptide and HDL cholesterol and apolipoprotein AI by observing whether or not the first sample has a higher level of HDL cholesterol and apolipoprotein AI than that of said other sample.

The present invention provides also a method for determining whether a test compound can enhance the enzymatic reaction between the LIPG polypeptide and VLDL cholesterol comprising: (A) comparing the level of VLDL cholesterol in a first sample comprising: (1) VLDL cholesterol, (2) LIPG polypeptide, and (3) the test compound with the level of VLDL cholesterol in another sample comprising: (4) VLDL cholesterol, and (5) LIPG polypeptide; and (B) identifying whether or not the test compound is effective in enhancing the enzymatic reaction between the LIPG polypeptide and VLDL cholesterol by observing whether or not the first sample has a lower level of VLDL cholesterol than that of said other sample.

Still another aspect of the present invention is the provision of a method for determining whether a test compound can enhance the enzymatic reaction between the LIPG polypeptide and LDL cholesterol comprising: (A) comparing the level of LDL cholesterol in a first sample comprising: (1) LDL cholesterol, (2) LIPG polypeptide, and (3) the test compound with the level of LDL cholesterol in another sample comprising: (4) LDL cholesterol, and (5) LIPG polypeptide; and (B) identifying whether or not the test compound is effective in enhancing the enzymatic reaction between the LIPG polypeptide and LDL cholesterol by observing whether or not the first sample has a lower level of LDL cholesterol than that of said other sample.

Figure 1A:
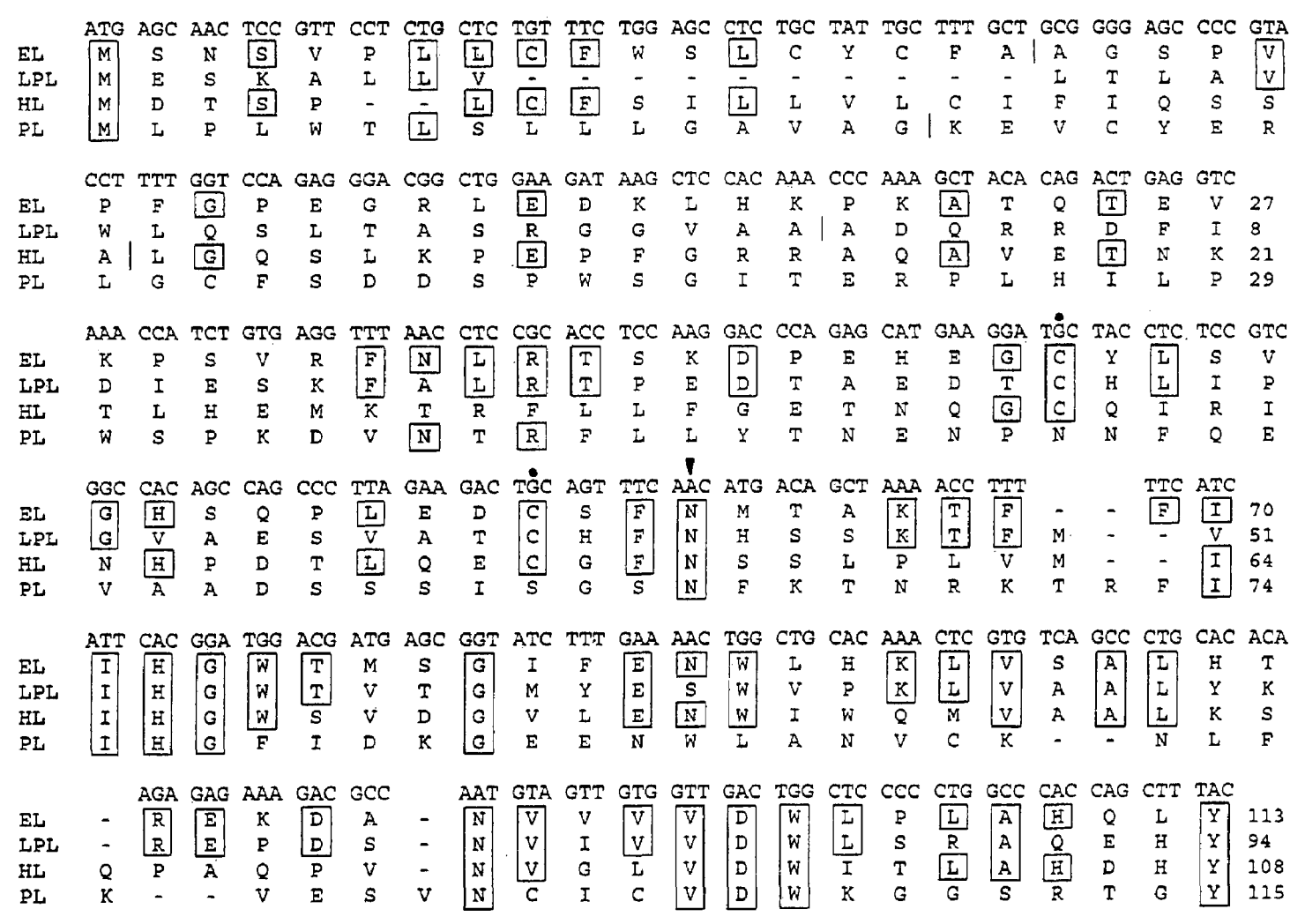
Figure 1B:
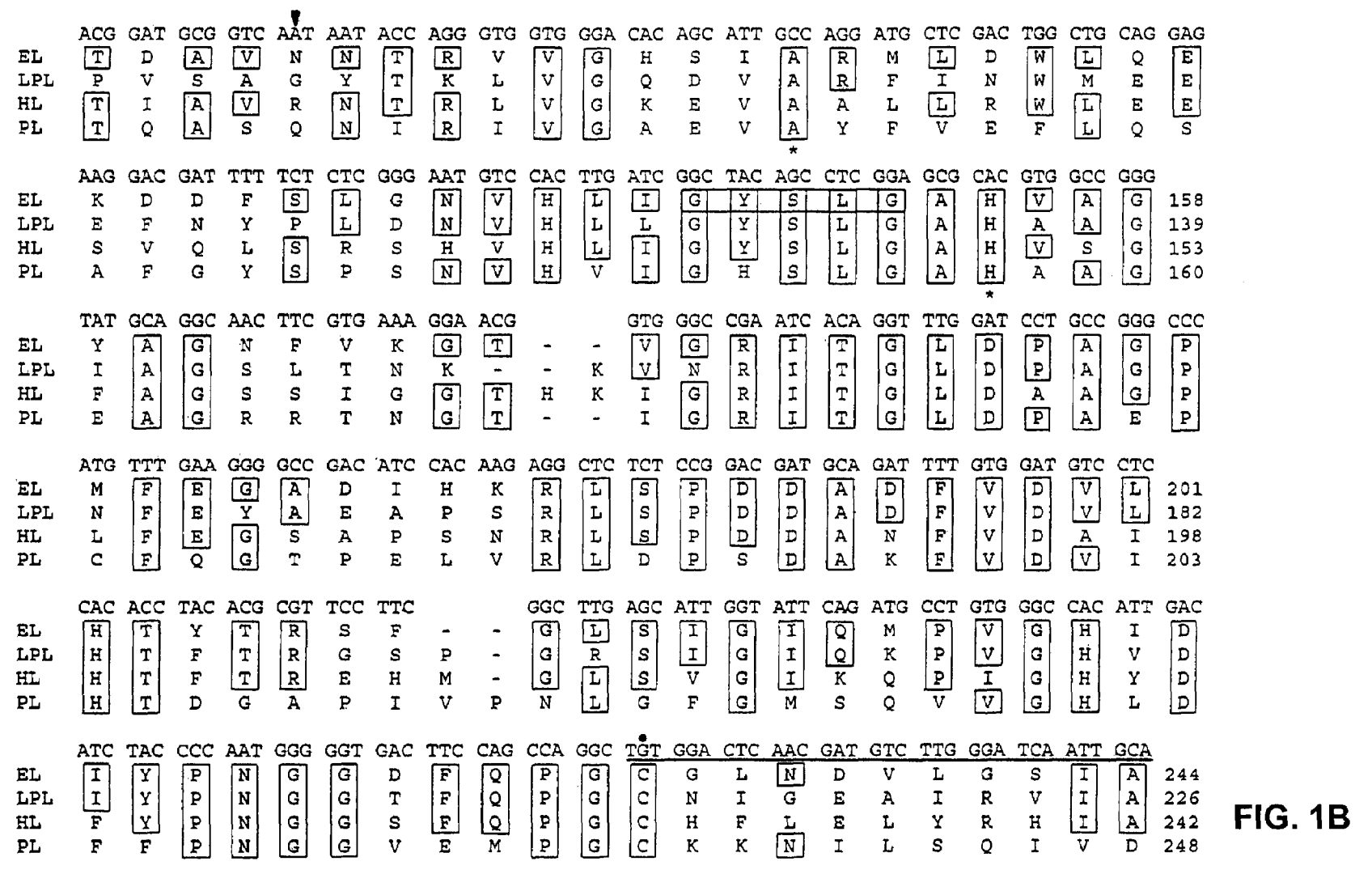
Figure 1C:
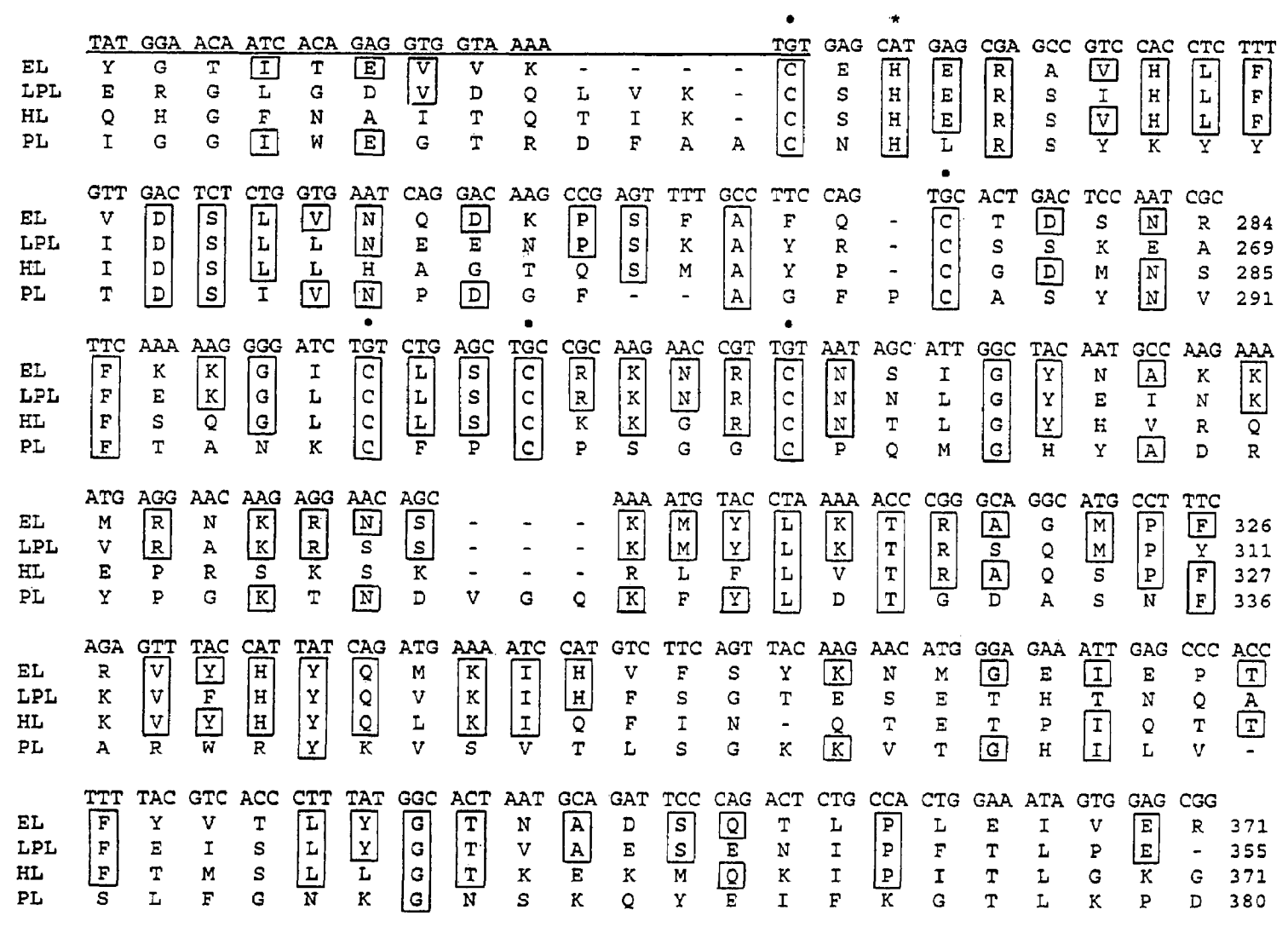
Figure 1D:
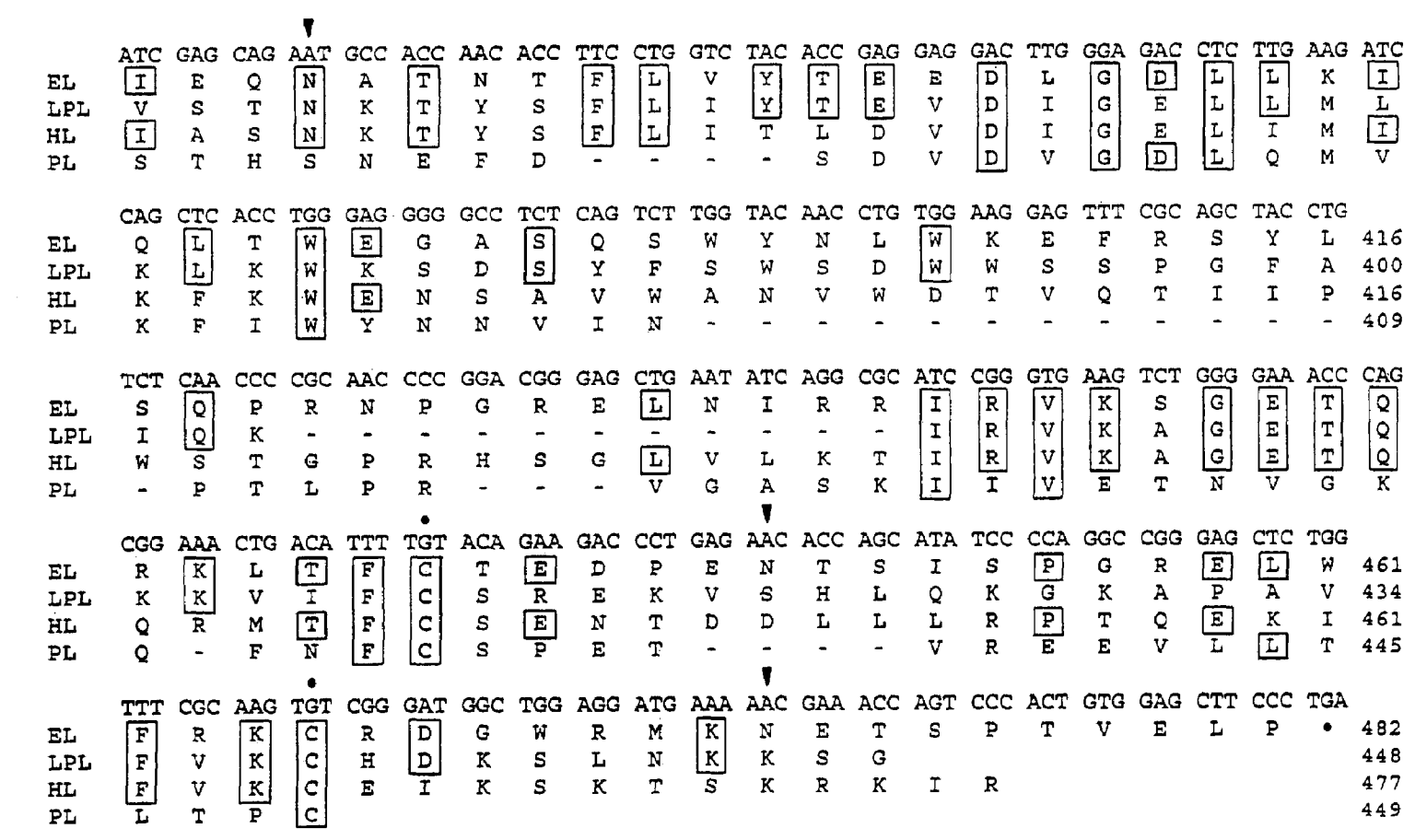

FIG. 1 shows a protein sequence alignment of the members of the triacylglycerol lipase gene family (SEQ ID Nos: 9–11). Shaded residues are identical to the LLGXL protein (SEQ ID NO: 6). The polynucleotide sequence at the top is the coding portion of the nucleic acid encoding LLGXL protein (nucleotides 0 to 1751 of SEQ ID NO: 5). The deduced amino acid sequence of human LIPG(EL; endothelial lipase) (SEQ ID NO: 6) is provided on the top line and is compared with the other major members of the TG lipase family, LPL (lipoprotein lipase) (SEQ ID NO: 9), HL (hepatic lipase) (SEQ ID NO: 10) and PL (pancreatic lipase) (SEQ ID NO: 11). EL residues identical to those in at least one other member of the family are shaded as well as the corresponding residue in the other family member. Amino acids are numbered according to convention beginning with the initial residue of the secreted protein. The predicted sites of signal peptide cleavage are marked with a solid line between amino acid residues. The GXSXG lipase motif containing the active serine is boxed. The amino acids of the catalytic triad are marked with an asterisk. The conserved cysteines are marked with filled circles. Potential N-linked glycosylation sites are marked with arrowheads. The lid region is indicated by a bold line. Gaps were introduced into the sequences to maximize the alignment values using the CLUSTAL program.

FIG. 2 shows a northern analysis of LIPG mRNA in THP-1 cells. Cells were stimulated with either PMA or PMA and oxidized LDL (PMA+oxLDL). Numbers at the left indicate the positions of RNA standards (in kilobases).

FIG. 3 shows a northern-blot analysis of expression of LIPG mRNA compared with LPL in human tissues. A blot containing mRNA from the indicated human tissues was incubated with radiolabelled LPL and β-actin (ACTB) probes as described.

FIG. 4 shows a Northern-blot analysis of cultured cell lines. The panel on the left (lanes 1–6) was hybridized with the LIPG(EL) probe and that on the right (lanes 7–12) with the LPL probe. Lanes 1, 7, unstimulated HUVEC; lanes 2, 8, HUVEC stimulated with PMA; lanes 3, 9, HUVEC stimulated with thrombin; lanes 4, 10, unstimulated HCAEC; lanes 5, 11, HCAEC stimulated with PMA; lanes 6, 12, THP-1 stimulated with PMA.

FIG. 5 shows the sequence of the immunizing peptide (SEQ ID NO: 12) and its relation to the LLGXL protein sequence (SEQ ID NO: 6). The peptide is shown in the shaded box. The terminal cysteine was introduced to aid coupling of the peptide to the carrier protein.

FIG. 6 shows the results obtained when conditioned media from HUVEC and HCAEC were subjected to immunoblot analysis with rabbit anti-EL peptide antiserum. Lane 1, unconditioned media; lane 2, unstimulated HUVEC; lane 3, HUVEC stimulated with PMA; lane 4, unstimulated HCAEC; lane 5, HCAEC stimulated with PMA.

FIG. 7 shows a western analysis of heparin-Sepharose bound proteins in conditioned medium from COS-7 cells transiently transfected with an expression vector containing a cDNA for LLGN or LLGXL or no DNA (Mock). Proteins from PMA-stimulated endothelial cells (HCAEC+PMA) were included for size reference. Numbers to the left indicate the apparent molecular weight of the major immunoreactive proteins as determined by a comparison to protein standards.

FIG. 8 shows the sequence of the rabbit LIPG PCR product (RLLG. SEQ, SEQ ID NO: 7) and the sequence alignment between the rabbit LIPG PCR product and the corresponding sequence in the human cDNA (LLG7742A) (nucleotides 1023 to 1247 of SEQ ID NO: 5). Identical nucleotides are shaded.

FIG. 9 shows the phospholipase A activity of human EL-AS, EL and LPL using a phosphatidylcholine substrate. To perform the assay 700 µl of conditioned medium harvested from COS-7 cells transiently transfected with either pcDNA3.0/LIPG-AS, LIPG, or LPL expression constructs were assayed in triplicate for phospholipase activities as described below. Following a two hour incubation at 37° C., reactions were terminated, and 14C labeled free fatty-acid was extracted, and counted to determine the amount of free fatty-acid produced.

FIG. 10 shows the triacylglyceride lipase activity of human EL-AS, EL and LPL using a triolein substrate. To perform the assay 700 µl of conditioned medium harvested from COS-7 cells transiently transfected with either pcDNA3.0/LIPG-AS, LIPG, or LPL expression constructs was assayed in triplicate for triglyceride activities described below. Following a two hour incubation at 37° C., reactions were terminated, and 14C labeled free fatty-acid was extracted, and counted to determine the amount of free fatty-acid produced.

DESCRIPTION OF THE SEQUENCES

Figure 2:
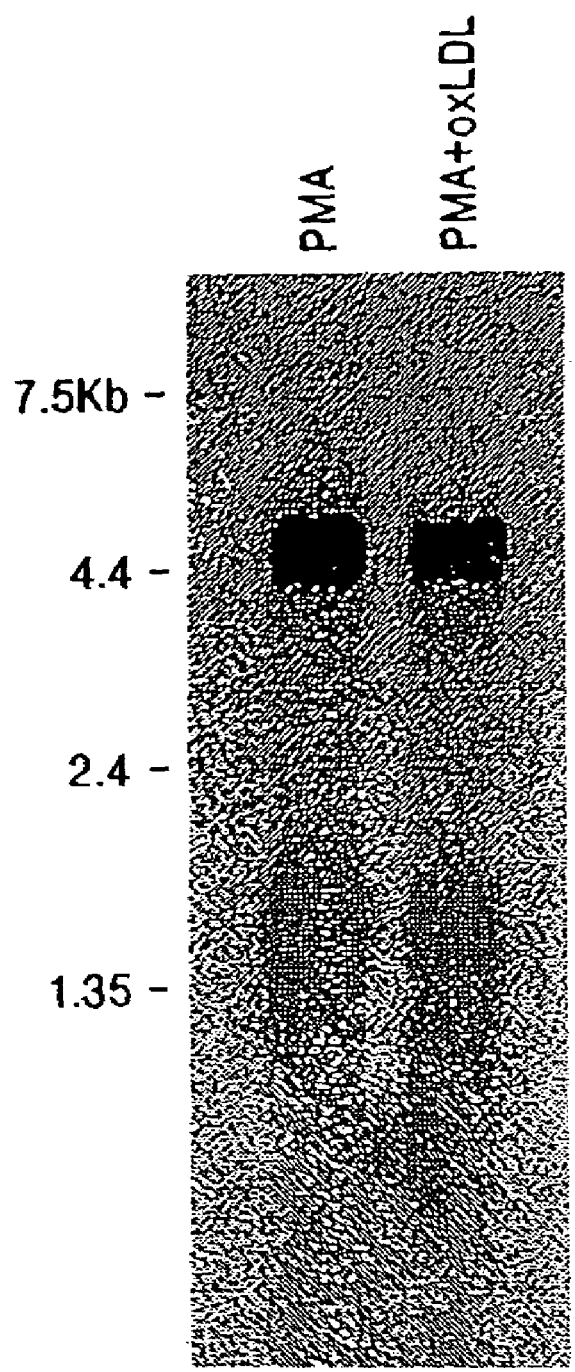

SEQ ID NO. 1 is the nucleic acid sequence of the differential display RT-PCR product containing a portion of the cDNA encoding human LIPG polypeptide.
SEQ ID NO. 2 is the deduced amino acid sequence encoded by SEQ ID NO. 1.
SEQ ID NO. 3 is the nucleic acid sequence of the 5' RACE extension of the cDNA fragment of SEQ ID NO. 1.
SEQ ID NO. 4 is the deduced amino acid sequence encoded by SEQ ID NO. 3.
SEQ ID NO. 5 is the nucleic acid sequence of the cDNA encoding human LLGXL polypeptide. This cDNA corresponds to an mRNA product formed from transcription of the human LIPG gene.
SEQ ID NO. 6 is the deduced amino acid sequence encoded by SEQ ID NO. 5 (the sequence for human LLGXL polypeptide).
SEQ ID NO. 7 is the nucleic acid encoding the rabbit LIPG PCR product.
SEQ ID NO. 8 is the deduced amino acid sequence encoded by SEQ ID NO. 7.
SEQ ID NO. 9 is the amino acid sequence for human lipoprotein lipase (LPL).
SEQ ID NO. 10 is the amino acid sequence for human hepatic lipase (HL).
SEQ ID NO. 11 is the amino acid sequence for human pancreatic lipase (PL).
SEQ ID NO. 12 is the amino acid sequence of an immunizing peptide corresponding to residues 8 to 23 of LLGXL polypeptide.
SEQ ID NO. 13 is the nucleic acid sequence for differential display downstream primer 7.
SEQ ID NO. 14 is the nucleic acid sequence for differential display upstream primer 15.
SEQ ID NO. 15 is the nucleic acid sequence for 5' RACE Primer 2a.
SEQ ID NO. 16 is the nucleic acid sequence for 5' RACE Primer 3a.
SEQ ID NO. 17 is the nucleic acid sequence for 5'RACE Primer 4a.
SEQ ID NO. 18 is the nucleic acid sequence for 5' RACE anchor primer.
SEQ ID NO. 19 is the nucleic acid sequence for the 5' RACE universal amplification primer.
SEQ ID NO. 20 is the nucleic acid sequence for 5' LPL primer.
SEQ ID NO. 21 is the nucleic acid sequence for 3' LPL primer.
SEQ ID NO. 22 is the nucleic acid sequence for primer DLIP774.
SEQ ID NO. 23 is the nucleic acid sequence for primer LLGgen2a.
SEQ ID NO. 24 is the nucleic acid sequence for Hllg-gsp1 primer.
SEQ ID NO. 25 is the nucleic acid sequence for Hllg-gsp2a primer.
SEQ ID NO. 26 is the nucleic acid sequence for G3PDH 5' primer.
SEQ ID NO. 27 is the nucleic acid sequence for G3PDH 3' primer.

DETAILED DESCRIPTION OF THE INVENTION

The detailed description which follows sets forth the basis for the present invention, followed by a definitions section. Following the definitions section, the various compositions useful in the practice of the invention are discussed, followed by a discussion of the methods used to lower or raise the levels of LIPG activity.

The Enzymatic Activity of the LIPG Gene Product

The present invention relates to methods for regulating the levels of HDL cholesterol and apolipoprotein AI, VLDL cholesterol and LDL cholesterol utilizing methods and compositions which lower or raise the activity of the LIPG lipase enzyme. In particular, the present invention is based in part on the discovery of the enzymatic activity of the polypeptide products of the LIPG gene on HDL cholesterol and apolipoprotein AI, VLDL cholesterol and LDL cholesterol. The polypeptide products of LIPG are members of the triacylglycerol lipase family and comprise an approximately 39 kD catalytic domain of the triacylglycerol lipase family. Because this newly discovered lipase was found to be synthesized by endothelial cells and this is a unique feature compared with other members of the triacylglycerol lipase family, this lipase has been named "endothelial lipase" (EL). Because the LIPG gene will be discussed extensively in the sections which follow, EL will be hereinafter referred to as LIPG polypeptide, for the purposes of clarity. In general, the LIPG polypeptide is found in two major forms, referred to hereinafter as "the LLGN polypeptide" and "the LLGXL polypeptide." The LLGN polypeptide, has 354 amino acids. The LLGXL polypeptide has 500 amino acids and exhibits 43% similarity to human lipoprotein lipase and 37% similarity to human hepatic lipase. As used herein, the term "LIPG polypeptide" or "LIPG protein" encompasses both LLGN and LLGXL.

The sequence of the LIPG polypeptide contains the characteristic GXSXG lipase motif, a conserved catalytic triad, a 19-residue lid region, conserved heparin and lipoprotein binding sites and 5 potential N-linked glycosylation sites. The region with the greatest sequence divergence in the triacylglycerol lipase family is the lid domain, which forms an amphipathic helix covering the catalytic pocket of the enzyme (Winkler et al., *Nature,* 343, 771–774 (1990); van Tilbeurgh et al., *J. Biol. Chem.,* 269, 4626–4633 (1994)) and confers substrate specificity to the enzymes of this family (Dugi et al., *J. Biol. Chem.,* 270, 25396–25401 (1995)). The 19-residue lid region of LIPG is three residues shorter and less amphipathic than those found in lipoprotein lipase and hepatic lipase, consistent with a different enzymatic profile. The predicted molecule weight of the mature protein is approximately 55 kD; a 68 kD form is likely to be a glycosylated form, whereas a 40 kD form may be the product of a specific proteolytic cleavage.

The Enzymatic Activity of the LIPG Gene Product

The sequence of the LIPG polypeptide contains the characteristic GXSXG lipase motif, a conserved catalytic triad, a 19-residue lid region, conserved heparin and lipoprotein binding sites and 5 potential N-linked glycosylation sites. The region with the greatest sequence divergence in the triacylglycerol lipase family is the lid domain, which forms an amphipathic helix covering the catalytic pocket of the enzyme (Winkler et al., Nature, 343, 771–774 (1990); van Tilbeurgh et al., J. Biol. Chem., 269, 4626–4633 (1994)) and confers substrate specificity to the enzymes of this family (Dugi et al., J. Biol. Chem., 270, 25396–25401 (1995)). The 19-residue lid region of LIPG is three residues shorter and less amphipathic than those found in lipoprotein lipase and hepatic lipase, consistent with a different enzymatic profile. The predicted molecule weight of the mature protein is approximately 55 kD; a 68 kD form is likely to be a glycosylated form, whereas a 40 kD form may be the product of a specific proteolytic cleavage.

The LIPG polypeptide has the ability to lower the levels of HDL cholesterol and apolipoprotein AI as well as the levels of VLDL cholesterol and LDL cholesterol. It is well established that lowered HDL cholesterol levels result in increased susceptibility to atherosclerosis and increased levels of HDL cholesterol can dramatically reduce susceptibility to atherosclerosis.

One physiologic role of LIPG may be to hydrolyse HDL phospholipid in peripheral tissues and in liver to facilitate selective uptake of HDL cholesteryl ester via the HDL receptor SR-BI (Kozarsky et al., Nature, 387, 414–417 (1997)). Another possible role is the facilitation of apoB-containing remnant lipoprotein uptake, similar to the role of hepatic lipase (Mahley et al., J. Lipid Res., 40, 1–16 (1999)). In addition, LIPG is abundantly expressed in the placenta, and a role for this enzyme in development is possible, given the importance of lipid transport in fetal development (Farese et al., Trends Genet., 14, 115–120 (1998)).

Based on HDL cholesterol's beneficial properties, it is desirable to raise HDL cholesterol levels by lowering the enzymatic activity of LIPG. Accordingly, the present invention is directed to methods and compositions which lower the activity of LIPG in the body by lowering the expression of the LIPG gene or lowering the enzymatic activity of the LIPG polypeptide.

Given the ability of the LIPG polypeptide to reduce the levels of VLDL cholesterol and LDL cholesterol and the studies demonstrating the correlation between high levels of these compounds and atherosclerotic diseases, it is desirable to lower the level of these compounds in a patient. Accordingly, the present invention additionally provides methods and compositions for increasing the expression of the LIPG gene and increasing the enzymatic activity of the LIPG polypeptides.

There are set forth hereafter definitions of terms used herein and descriptions of preferred embodiments of the present invention.

Definitions

The following defined terms are used throughout the present specification and should be helpful in understanding the scope and practice of the present invention.

A "polypeptide" is a polymeric compound comprised of covalently linked amino acid residues. Amino acids are classified into seven groups on the basis of the side chain: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide which plays a structural or functional role in a living cell.

The polypeptides and proteins of the invention may be glycosylated or unglycosylated.

"Homology" means similarity of sequence reflecting a common evolutionary origin. Polypeptides or proteins are said to have homology, or similarity, if a substantial number of their amino acids are either (1) identical, or (2) have a chemically similar side chain. Nucleic acids are said to have homology if a substantial number of their nucleotides are identical.

"Isolated polypeptide" or "isolated protein" is a polypeptide or protein which is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

"LLGXL polypeptide" and "LLGXL protein" mean a polypeptide including the sequence SEQ ID NO: 6, said polypeptide being glycosylated or non-glycosylated.

"LIPG polypeptide" and "LIPG protein" describe the lipase enzyme encoded by the LIPG gene and generically describes both the LLGN polypeptide and the LLGXL polypeptide.

"Endothelial lipase," or "EL", refer to the lipase enzyme encoded by the LIPG gene and is equivalent to the term LIPG polypeptide.

The LIPG polypeptide or protein of the invention includes any analogue, fragment, derivative, or mutant which is derived from an LIPG polypeptide and which retains at least one biological property of the LIPG polypeptide. Different variants of the LIPG polypeptide exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the LIPG polypeptide, (c) variants in which one or more of the amino acids includes a substituent group, and (d) variants in which the LIPG polypeptide is fused with another polypeptide such as serum albumin. Other LIPG polypeptides of the invention include variants in which amino acid residues from one species are substituted for the corresponding residue in another species, either at conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the LIPG polypeptide which retain any of the biological properties of the LIPG polypeptide, they are included within the scope of this invention.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence.

An "antisense nucleic acid" is a sequence of nucleotides that is complementary to the sense sequence. Antisense nucleic acids can be used to down regulate or block the expression of the polypeptide encoded by the sense strand.

"Isolated nucleic acid" means a nucleic acid which is substantially free of those compounds that are normally associated therewith in its natural state. "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

The phrase "a nucleic acid which hybridizes at high stringency" means that the hybridized nucleic acids are able to withstand a washing under high stringency conditions. An example of high stringency washing conditions for DNA—DNA hybrids is 0.1×SSC, 0.5% SDS at 68° C. Other conditions of high stringency washing are known to persons having ordinary skill in the art.

"Regulatory region" means a nucleic acid sequence which regulates the expression of a nucleic acid. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "vector" is any means for the transfer of a nucleic acid according to the invention into a host cell. The term "vector" includes both viral and nonviral means for introducing the nucleic acid into a prokaryotic or eukaryotic cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors. In addition to nucleic acid according to the invention, a vector may also contain one or more regulatory regions, and/or selectable markers useful in selecting, measuring, and monitoring nucleic acid transfer results (transfer to which tissues, duration of expression, etc.).

A "recombinant cell" is a cell which contains a nucleic acid which is not naturally present in the cell. "Recombinant cell" includes higher eukaryotic cells such as mammalian cells, lower eukaryotic cells such as yeast cells, prokaryotic cells, and archaebacterial cells.

"Pharmaceutically acceptable carrier" includes diluents and fillers which are pharmaceutically acceptable for methods of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

A "lipase" is a protein which can enzymatically cleave a lipid substrate.

A "phospholipase" is a protein which can enzymatically cleave a phospholipid substrate.

A "triacylglycerol lipase" is a protein which can enzymatically cleave a triacylglyceride substrate.

"Phosphatidylcholine" is a glycerol phospholipid. Phosphatidylcholine is also known as lecithin.

"Lipid profile" means the set of concentrations of cholesterol, triglyceride, lipoprotein cholesterol and other lipids in the body of a human or other animal.

An "undesirable lipid profile" is the condition in which the concentrations of cholesterol, triglyceride, or lipoprotein cholesterol are outside of the age- and gender-adjusted reference ranges. Generally, a concentration of total cholesterol>200 mg/dl, of plasma triglycerides>200 mg/dl, of LDL cholesterol>130 mg/dl, of HDL cholesterol<39 mg/dl, or a ratio of total cholesterol to HDL cholesterol>4.0 is considered to be an undesirable lipid profile. An undesirable lipid profile is associated with a variety of pathological conditions, including hyperlipidaemias, diabetes hypercholesterolaemia, atherosclerosis, and other forms of coronary artery disease.

A "ribozyme" is an RNA molecule which can function as an enzyme.

A "neutralizing antibody" is an antibody which can bind to an LIPG polypeptide and lower or eliminate the enzymatic activity of the LIPG polypeptide. These antibodies may be monoclonal antibodies or polyclonal antibodies. The present invention includes chimeric, single chain, and humanized antibodies, as well as Fab fragments and the products of an Fab expression library, and Fv fragments and the products of an Fv expression library.

An "inhibitory molecule" or "inhibitor" is a molecule which lowers or eliminates the expression of the LIPG polypeptide or which lowers or eliminates the enzymatic activity of the LIPG polypeptide.

An "enhancer molecule" or "enhancer" is a molecule which increases the expression of the LIPG polypeptide or which increases the enzymatic activity of the LIPG polypeptide.

A "liposome" is an artificial or naturally-occurring phospholipid vesicle.

A "cationic liposome" is a liposome having a net positive electrical charge.

The sections which follow discuss the elements used in the claimed methods and compositions and the preferred embodiments of these elements.

Polypeptides

The present invention utilizes polypeptides encoded by LIPG which are members of the triacylglycerol lipase family, and which comprise a 39 kD catalytic domain of the triacylglycerol lipase family. In an embodiment of the present invention, an isolated LIPG polypeptide comprising the sequence SEQ ID NO: 8 and having an apparent molecular weight of about 55 kD or 68 kD on a 10% SDS-PAGE gel is utilized.

The polypeptides and proteins utilized in the present invention may be recombinant polypeptides, natural polypeptides, or synthetic polypeptides, and may be of human, rabbit, or other animal origin. The polypeptides are characterized by a reproducible single molecular weight and/or multiple set of molecular weights, chromatographic response and elution profiles, amino acid composition and sequence, and biological activity.

The polypeptides utilized in the present invention may be isolated from natural sources, such as placental extracts, human plasma, or conditioned media from cultured cells such as macrophages or endothelial cells, by using the purification procedures known to one of skill in the art.

Alternatively, the polypeptides utilized in the present invention may be prepared utilizing recombinant DNA technology, which comprises combining a nucleic acid encoding the polypeptide thereof in a suitable vector, inserting the resulting vector into a suitable host cell, recovering the polypeptide produced by the resulting host cell, and purifying the polypeptide recovered.

Nucleic Acids

The present invention utilizes isolated nucleic acids which encode LIPG polypeptides.

The present invention also utilizes antisense nucleic acids which can be used to down regulate or block the expression of LIPG polypeptides in vitro, ex vivo or in vivo.

The techniques of recombinant DNA technology are known to those of ordinary skill in the art. General methods for the cloning and expression of recombinant molecules are described in Maniatis (*Molecular Cloning*, Cold Spring Harbor Laboratories, 1982), and in Ausubel (*Current Protocols in Molecular Biology*, Wiley and Sons, 1987), which are incorporated by reference.

The nucleic acids of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the present invention include both constituitive promoters and regulated (inducible) promoters. The promoters may be prokaryotic or eukaryotic depending on the host. Among the prokaryotic (including bacteriophage) promoters useful for practice of this invention are lacI, lacZ, T3, T7, lambda $P_r$, $P_l$, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, Cold Spring Harbor Symp. Quant. Biol., 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.*, 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.*, 5:1639–1648; Hammer et al., 1987, *Science* 235:53–58), alpha 1-antitrypsin gene control region which is active in the liver (Kelsey et al., 1987, *Genes and Devel.*, 1:161–171), beta-globin gene control region which is active in myeloid cells (Mogram et al., 1985, *Nature* 315:338–340; Kollias et al., 1986, *Cell* 46:89–94), myelin basic protein gene control region which is active in oligodendrocyte cells in the brain (Readhead et al., 1987, *Cell* 48:703–712), myosin light chain-2 gene control region which is active in skeletal muscle (Sani, 1985, *Nature* 314:283–286), and gonadotropic releasing hormone gene control region which is active in the hypothalamus (Mason et al., 1986, *Science* 234:1372–1378).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the contents of which are incorporated herein by reference.

Viral Vector Systems

Preferably, the viral vectors used in the gene therapy methods of the present invention are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents.

Preferably, the replication defective virus retains the sequences of its genome which are necessary for encapsidating the viral particles.

The retroviruses are integrating viruses which infect dividing cells. The retrovirus genome includes two LTRs, an encapsidation sequence and three coding regions (gag, pol and env). The construction of recombinant retroviral vectors has been described: see, in particular, EP 453242, EP178220, Bernstein et al. Genet. Eng. 7 (1985) 235; McCormick, BioTechnology 3 (1985) 689, etc. In recombinant retroviral vectors, the gag, pol and env genes are generally deleted, in whole or in part, and replaced with a heterologous nucleic acid sequence of interest. These vectors can be constructed from different types of retrovirus, such as, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Lentivirus vector systems may also be used in the practice of the present invention. The lentiviral genome is a positive-strand polyadenylated RNA of 9,000 to 10,000 base pairs containing three structural genes organized 5' to 3' (gag, pol, env), typical of all retroviruses. For an extensive review of lentiviral systems, see *Fields Virology*, Second Edition, Volume 2, Chapter 55, "Lentiviruses," pp. 1571–1589, Raven Press, New York, 1990.

In general, in order to construct recombinant retroviruses containing a sequence encoding LIPG, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987) 1639). Recombinant retroviral vectors are purified by standard techniques known to those having ordinary skill in the art.

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs utilized in the present invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques. The invention also relates, therefore, to an AAV-derived recombinant virus whose genome encompasses a sequence encoding an LIPG polypeptide flanked by the AAV ITRs. The invention also relates to a plasmid encompassing a sequence encoding an LIPG polypeptide flanked by two ITRs from an AAV. Such a plasmid can be used as it is for transferring the LIPG sequence, with the plasmid, where appropriate, being incorporated into a liposomal vector (pseudo-virus).

In a preferred embodiment, the vector utilized in the present invention is an adenovirus vector.

Adenoviruses are eukaryotic DNA viruses that can be modified to efficiently deliver a nucleic acid to a variety of cell types.

Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus. Other regions may also be modified, in particular the E3 region (WO95/02697), the E2 region (WO94/28938), the E4 region (WO94/28152, WO94/12649 and WO95/02697), or in any of the late genes L1–L5. Defective retroviral vectors are disclosed in WO95/02697.

In a preferred embodiment, the adenoviral vector has a deletion in the E1 and E4 regions. In another preferred embodiment, the adenoviral vector has a deletion in the E1 region into which the E4 region and the sequence encoding LLG are inserted (see FR94 13355).

The replication defective recombinant adenoviruses can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Antisense Nucleic Acids

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding LIPG or the corresponding messenger RNA. In addition, antisense nucleic acids may be designed or identified which decrease expression of the LIPG gene by inhibiting splicing of its primary transcript. With knowledge of the structure and partial sequence of the LIPG gene, such antisense nucleic acids can be designed and tested for efficacy.

The antisense nucleic acids are preferably oligonucleotides and may consist entirely of deoxyribonucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target site, the RNA-DNA duplex activates the endogenous enzyme ribonuclease (Rnase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its target site. Modifications may include 2' deoxy, O-pentoxy, O-propoxy, O-methoxy, fluoro, methoxyethoxy phosphoro-thioates, modified bases, as well as other modifications known to those of skill in the art.

The antisense nucleic acids can also be DNA sequences whose expression in the cell produces RNA complementary to all or part of the LIPG mRNA. Antisense nucleic acids can be prepared by expression of all or part of a sequence selected from the group consisting of SEQ ID No. 2, SEQ ID No. 3, SEQ ID No. 5, or SEQ ID No. 7, in the opposite orientation, as described in EP 140308. Any length of antisense sequence is suitable for practice of the invention so long as it is capable of down-regulating or blocking expression of LIPG. Preferably, the antisense sequence is at least 20 nucleotides in length. The preparation and use of antisense nucleic acids, DNA encoding antisense RNAs and the use of oligo and genetic antisense is disclosed in WO92/15680, the contents of which are incorporated herein by reference.

One approach to determining the optimum fragment of LIPG to use in an antisense nucleic acid treatment method involves preparing random fragments of LIPG cDNA by mechanical shearing, enzymatic treatment, and cloning the fragment into any of the vector systems described herein. Individual clones or pools of clones are used to infect LIPG-expressing cells, and effective antisense LIPG cDNA fragments are identified by monitoring LIPG expression at the RNA or protein level.

The retroviral, adeno-associated viral, and adenoviral vector systems discussed hereinabove may all be used to introduce and express antisense nucleic acids in cells. Antisense synthetic oligonucleotides may be introduced in a variety of ways, including the methods discussed hereinbelow.

Ribozymes

Reductions in the levels of LIPG polypeptide may be accomplished using ribozymes. Ribozymes are catalytic RNA molecules (RNA enzymes) that have separate catalytic and substrate binding domains. The substrate binding sequence combines by nucleotide complementarity and, possibly, nonhydrogen bond interactions with its target sequence. The catalytic portion cleaves the target RNA at a specific site. The substrate domain of a ribozyme can be engineered to direct it to a specified mRNA sequence. The ribozyme recognizes and then binds a target mRNA through complementary base-pairing. Once it is bound to the correct target site, the ribozyme acts enzymatically to cut the target mRNA. Cleavage of the LIPG mRNA by a ribozyme destroys its ability to direct synthesis of LIPG polypeptide. Once the ribozyme has cleaved its target sequence, it is released and can repeatedly bind and cleave at other LIPG mRNAs.

In preferred embodiments of this invention, the ribozyme is formed in a hammerhead motif. Other forms include a hairpin motif, a hepatitis delta virus, group I intron or RnaseP RNA (in association with an RNA guide sequence) motif or *Neurospora* VS RNA motif. Hammerhead motifs are described by Rossi et al., 1992, *Aids Research and Human Retroviruses*, 8, 183. Hairpin motifs are described in Hampel and Tritz, 1989, *Biochemistry*, 28, 4929, and Hampel et al., 1990, *Nucleic Acids Res.*, 18, 299. The hepatitis delta virus motif is described by Perrotta and Been, 1992, *Biochemistry*, 31, 16, the RnaseP motif is described by Guerrier-Takada et al., 1983, *Cell*, 35, 849, the *Neurospora* VS RNA ribozyme motif is described by Collins (Saville and Collins, 1990, *Cell*, 61, 685–696; Saville and Collins, 1991, *Proc. Natl. Acad. Sci. USA*, 88, 8826–8830; Collins and Olive, 1993, *Biochemistry*, 32, 2795–2799) the Group I intron motif is described by Cech et al., U.S. Pat. No. 4,987,071.

One approach in preparing a ribozyme is to chemically synthesize an oligodeoxyribonucleotide with a ribozyme catalytic domain (~20 nucleotides) flanked by sequences that hybridize to the target LIPG mRNA after transcription. The oligodeoxyribonucleotide is amplified by using the substrate binding sequences as primers. The amplification product is cloned into a eukaryotic expression vector.

Ribozymes possessing a hammerhead or hairpin structure are readily prepared since these catalytic RNA molecules can be expressed within cells from eukaryotic promoters (e.g., Scanlon et al., 1991, *Proc. Natl. Acad. Sci. USA*, 88, 10591–5; Kashani-Sabet et al., 1992, *Antisense Res. Dev.*, 2, 3–15; Dropulic et al., 1992, *J. Virol.*, 66, 1432–41; Weerasinghe et al., 1991, *J. Virol.*, 65, 5531–4; Ojwang et al., 1992, *Proc. Natl. Acad. Sci. USA*, 89, 10802–6; Chen et al., 1992, *Nucleic Acids Res.*, 20, 4581–9; Sarver et al., 1990, *Science*, 247, 1222–1225)). A ribozyme of the present invention can be expressed in eukaryotic cells from the appropriate DNA vector. If desired, the activity of the ribozyme may be augmented by its release from the primary transcript by a second ribozyme (Ohkawa et al., 1992, *Nucleic Acids Symp. Ser.*, 27, 15–6; Taira et al., 1991, *Nucleic Acids Res.*, 19, 5125–30; Ventura et al., 1993, *Nucleic Acids Res.*, 21, 3249–55).

In one approach to preparing ribozymes, ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743–7; Gao and Huang 1993, Nucleic Acids Res., 21, 2867–72; Lieber et al., 0.1993, Methods Enzymol., 217, 47–66; Zhou et al., 1990, Mol. Cell. Biol., 10, 4529–37). It has been demonstrated that ribozymes expressed from these promoters can function in mammalian cells (Kashani-Sabet et al., 1992, Antisense Res. Dev., 2, 3–15; Ojwang et al., 1992, Proc. Natil. Acad. Sci. USA, 89, 10802–6; Chen et al., 1992 Nucleic Acids Res., 20, 4581–9; Yu et al., 1993, Proc. Natl. Acad. Sci. USA, 90, 6340–4; L'Huillier et al., 1992, EMBO J., 11, 4411–8; Lisziewicz et al., 1993, Proc. Natl. Acad. Sci. USA, 90, 8000–4).

In one embodiment of the present invention, a transcription unit expressing a ribozyme that cleaves LIPG RNA is inserted into a plasmid DNA vector, a retrovirus vector, an adenovirus DNA viral vector or an adeno-associated virus vector. The recombinant vectors are preferably DNA plasmids or adenovirus vectors. However, other mammalian cell vectors that direct the expression of RNA may be used for this purpose. The vectors are delivered as recombinant viral particles. DNA may be delivered alone or complexed with various vehicles. The DNA, DNA/vehicle complexes, or the recombinant virus particles are locally administered to the site of treatment, as discussed below. Preferably, recombinant vectors capable of expressing the ribozymes are locally delivered as described below, and persist in target cells. Once expressed, the ribozymes cleave the target LIPG mRNA.

Ribozymes may be administered to a patient by a variety of methods. They may be added directly to target tissues, complexed with cationic lipids, packaged within liposomes, or delivered to target cells by other methods known in the art. Localized administration to the desired tissues may be done by catheter, infusion pump or stent, with or without incorporation of the ribozyme in biopolymers as discussed hereinbelow. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. More detailed descriptions of ribozyme delivery and administration are provided in Sullivan et al., PCT WO94/02595 and Draper et al., PCT WO93/23569, which are incorporated by reference herein.

Non-Viral Delivery Systems

Certain non-viral systems have been used in the art and can facilitate introduction of DNA encoding the LIPG polypeptides or antisense nucleic acids into a patient.

A DNA vector encoding a desired LIPG polypeptide or antisense sequence can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., Proc. Natl. Acad. Sci. U.S.A. 84:7413–7417 (1987); see Mackey, et al., Proc. Natl. Acad. Sci. U.S.A. 85:8027–8031 (1988); Ulmer et al., Science 259:1745–1748 (1993)]. The use of cationic lipids may promote encapsulation of negatively charged nucleic acids, and also promote fusion with negatively charged cell membranes [Felgner and Ringold, Science 337:387–388 (1989)]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, for example, pancreas, liver, kidney, and the brain. Lipids may be chemically coupled to other molecules for the purpose of targeting [see Mackey, et. al., supra]. Targeted peptides, e.g., hormones or neurotransmitters, and proteins for example, antibodies, or non-peptide molecules could be coupled to liposomes chemically.

Other molecules are also useful for facilitating transfection of a nucleic acid in vivo, for example, a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce A DNA vector encoding a LIPG polypeptide or antisense sequence in vivo as a naked DNA plasmid (see U.S. Pat. Nos. 5,693,622, 5,589,466 and 5,580,859). Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963–967 (1992); Wu and Wu, J. Biol. Chem. 263:14621–14624 (1988); Hartmut et al., Canadian Patent Application No. 2,012,311, filed Mar. 15, 1990; Williams et al., Proc. Natl. Acad. Sci. USA 88:2726–2730 (1991)]. Receptor-mediated DNA delivery approaches can also be used [Curiel et al., Hum. Gene Ther. 3:147–154 (1992); Wu and Wu, J. Biol. Chem. 262:4429–4432 (1987)].

Antibodies

The present invention provides antibodies against the LIPG polypeptide. These antibodies may be monoclonal antibodies or polyclonal antibodies. The present invention includes chimeric, single chain, and humanized antibodies, as well as Fab fragments and the products of an Fab expression library, and Fv fragments and the products of an Fv expression library.

Polyclonal antibodies may be prepared against an antigenic fragment of an LIPG polypeptide, as described in the Examples section hereinbelow. Antibodies may also be generated against the intact LIPG protein or polypeptide, or against a fragment, derivative, or epitope of the protein or polypeptide. Antibodies may be obtained following the administration of the protein, polypeptide, fragment, derivative, or epitope to an animal, using the techniques and procedures known in the art.

Monoclonal antibodies may be prepared using the method of Mishell, B. B., et al., Selected Methods In Cellular Immunology, (W.H. Freeman, ed.) San Francisco (1980). Briefly, a polypeptide of the present invention is used to immunize spleen cells of Balb/C mice. The immunized spleen cells are fused with myeloma cells. Fused cells containing spleen and myeloma cell characteristics are isolated by growth in HAT medium, a medium which kills both parental cells, but allows the fused products to survive and grow.

The monoclonal antibodies of the present invention may be "humanized" to prevent the host from mounting an immune response to the antibodies. A "humanized antibody" is one in which the complementarity determining regions (CDRS) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. G. E. Mark and E. A. Padlan, "Chapter 4. Humanization of Monoclonal Antibodies", The Handbook of Experimental Pharmacology Vol. 113, Springer-Verlag, New York, 1994). Transgenic animals may be used to express humanized antibodies.

Techniques known in the art for the production of single chain antibodies can be adapted to produce single chain antibodies to the immunogenic polypeptides and proteins of the present invention.

In a preferred embodiment, an anti-LIPG antibody is used to bind to and inhibit the enzymatic activity of LIPG in a patient.

The anti-LIPG antibodies are also useful in assays for detecting or quantitating levels of LIPG. In one embodiment, these assays provide a clinical diagnosis and assessment of LIPG in various disease states and a method for monitoring treatment efficacy. These anti-LIPG antibodies may additionally be used to quantitate LIPG in a tissue sample in order to predict further susceptibility to lowered levels of HDL cholesterol and apolipoprotein AI.

Methods of Identifying and Utilizing Inhibitory Molecules and Enhancer Molecules The present invention provides methods of screening small molecule libraries or natural product sources for enhancers (agonists) or co-activators including proteinaceous co-activators or inhibitors (antagonists) of LIPG activity. A potential enhancer or inhibitor is contacted with LIPG protein and a substrate of LIPG, and the ability of the potential enhancer or inhibitor to enhance or inhibit LIPG activity is measured.

These screening methods may also be used to determine if a compound can function as a substrate specific enhancer or inhibitor, that is, whether a compound can enhance the enzymatic activity of LIPG toward one substrate while lowering or maintaining a given level of enzymatic activity for a different substrate, for example, the LIPG polypeptide of the present invention utilizes HDL cholesterol as a substrate and also utilizes LDL cholesterol and VLDL cholesterol as substrates. In certain embodiments, it is desirable to isolate and identify substrate specific enhancers or inhibitors which enhance the enzymatic activity of the LIPG polypeptide towards LDL cholesterol or VLDL cholesterol while lowering or maintaining the normal level of enzymatic activity for HDL cholesterol.

The LIPG protein used in these methods can be produced recombinantly in a variety of host cells, including mammalian cells, baculovirus-infected insect cells, yeast, and bacteria. LIPG expression in stably transfected CHO cells can be optimized by methotrexate amplification of the cells. LIPG protein can also be purified from natural sources such as human plasma, placental extracts, or conditioned media from cultured endothelial cells, THP-1 cells, or macrophages.

The optimization of assay parameters including pH, ion concentrations, temperature, concentration of substrate, and emulsification conditions are determined empirically by one having ordinary skill in the art.

The fatty acid substituents of the substrates may vary in chain length as well as in degree and position of unsaturation. The substrates may be radiolabelled in any of several positions. Phospholipid substrates such as phosphatidylcholine can be radiolabelled, for example, in the Sn-1 or Sn-2 fatty acid position, or in the glycerol, phosphate, or polar head group (choline in the case of phosphatidylcholine).

As an alternative to radiolabeled substrates, other classes of labeled substrates, such as fluorescent substrates or thio-containing substrates, can also be used in the screening methods.

Fluorescent substrates are particularly useful in screening assays because enzymatic catalysis can be measured continuously by measuring fluorescence intensity, without the physical separation (extraction) of the products from the substrates. An example of a fluorescent phosphatidylcholine substrate is $C_6$NBD-PC{1-acyl-2-[6-(nitro-2,1,3-benzoxadiazol-4-yl)amino] caproylphosphatidylcholine.

The thio-containing substrates include 1,2-bis(hexanoylthio)-1,2-dideoxy-sn-glycero-3-phosphorylcholine (L. J. Reynolds, W. N. Washburn, R. A. Deems, and E. A. Dennis, 1991. Methods in Enzymology 197: 3–23; L. Yu and E. A. Dennis, 1991. Methods in Enzymology 197: 65–75; L. A. Wittenauer, K. Shirai, R. L. Jackson, and J. D. Johnson, 1984. Biochem. Biophys. Res. Commun. 118: 894–901).

In addition to inhibitory and enhancer molecules which operate at the level of enzymatic activity, there are inhibitory and enhancer molecules which operate at the level of expression of the LIPG gene. One method for identifying compounds which are able to enhance or inhibit the expression of LIPG is to use a reporter gene system. These systems utilize reporter gene expression vectors which include a cloning site into which a given promoter may be cloned upstream of a "reporter gene" which can be easily detected and quantified. One of skill in the art could readily identify and subclone the promoter for the LIPG gene as well as other control sequences into a commercially available reporter gene expression vector. The expression vector is transferred into host cells and the cells are exposed to a test compound (a putative inhibitor or enhancer molecule) to determine the effect of the test compound on expression of the reporter gene product. In particular, the cells are assayed for the presence of the reporter gene product by directly measuring the amount of reporter mRNA, the reporter protein itself or the enzymatic activity of the reporter protein. Ideally, the reporter gene is not endogenously expressed in the cell type of interest and lends itself to sensitive, quantitative and rapid assays. A variety of reporter assay constructs are commercially available and several reporter genes and assays have been developed and can be readily prepared by those of skill in the art. The most popular systems for monitoring genetic activity in eukaryotic cells include the chloramphenicol acetyltransferase (CAT), β-galactosidase, firefly luciferase, growth hormone (GH), β-glucurudase (GUS), alkaline phosphatase (AP), green fluorescent protein (GFP) and *Renilla* luciferase. Reporter assay constructs can be purchased from a variety of sources including Promega and Invitrogen.

As mentioned above, reporter gene activity can be detected by assaying for the reporter mRNA or the reporter protein. The reporter mRNA can be detected by northern blot analysis, ribonuclease protection assays or RT-PCR. While these assays are more direct than measuring protein expression, many assays have been developed to measure the presence of the reporter protein rather than the mRNA present in a cell. Reporter proteins can be assayed by spectrophotometry or by detecting enzymatic activity. Reporter protein levels may also be measured with antibody-based assays. In general, the enzymatic assays are very sensitive and are a preferred method of monitoring reporter gene expression.

Compositions

The present invention provides compositions in a biologically compatible (biocompatible) solution, comprising the polypeptides, nucleic acids, vectors, or antibodies of the invention. A biologically compatible solution is a solution in which the polypeptide, nucleic acid, vector, or antibody of the invention is maintained in an active form, e.g., in a form able to effect a biological activity. For example, a polypeptide of the invention would have phospholipase activity; a nucleic acid would be able to replicate, translate a message, or hybridize to a complementary nucleic acid; a vector would be able to transfect a target cell; an antibody would bind a polypeptide of the invention. Generally, such a biologically compatible solution will be an aqueous buffer, e.g., Tris, phosphate, or HEPES buffer, containing salt ions. Usually the concentration of salt ions will be similar to physiological levels. In a specific embodiment, the biocompatible solution is a pharmaceutically acceptable composition. Biologically compatible solutions may include stabilizing agents and preservatives.

Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well known nontoxic physiologically acceptable carriers, adjuvants and vehicles as desired.

The preferred sterile injectable preparations can be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel which is prepared from any biocompatible or non-cytotoxic (homo or hetero) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available. A hydrogel can be deposited directly onto the surface of the tissue to be treated, for example during surgical intervention.

Another preferred embodiment of the present invention relates to a pharmaceutical composition comprising a replication defective recombinant virus and poloxamer. More specifically, the invention relates to a composition comprising a replication defective recombinant virus comprising a nucleic acid encoding an LIPG polypeptide and poloxamer. A preferred poloxamer is Poloxamer 407, which is commercially available (BASF, Parsippany, N.J.) and is a non-toxic, biocompatible polyol, and is most preferred. A poloxamer impregnated with recombinant viruses may be deposited directly on the surface of the tissue to be treated, for example during a surgical intervention. Poloxamer possesses essentially the same advantages as hydrogel while having a lower viscosity.

Methods of Treatment

The present invention provides methods of treatment which comprise the administration to a human or other animal of an effective amount of a composition of the invention.

Effective amounts may vary, depending on the age, type and severity of the condition to be treated, body weight, desired duration of treatment, method of administration, and other parameters. Effective amounts are determined by a physician or other qualified medical professional. In most cases, the dosage levels may be adjusted so that the desired levels of HDL cholesterol and apolipoprotein AI are achieved and maintained. Similarly, the dosage levels may be adjusted to lower the VLDL cholesterol and LDL cholesterol levels to acceptable levels and bring the ratio HDL cholesterol to LDL cholesterol and VLDL cholesterol to within desirable levels.

Polypeptides according to the invention are generally administered in doses of about 0.01 mg/kg to about 100 mg/kg, preferably about 0.1 mg/kg to about 50 mg/kg, and most preferably about 1 mg/kg to about 10 mg/kg of body weight per day.

Neutralizing antibodies according to the invention may be delivered as a bolus only, infused over time or both administered as a bolus and infused over time. Although the dosage amount will vary based on the parameters above, and on the binding ability of the antibody, a dose 0.2 to 0.6 mg/kg may be given as a bolus followed by a 2 to 12 hour infusion period. Alternatively, multiple bolus injections are administered every other day or every third or fourth day as needed. Dosage levels may be adjusted as determined by HDL cholesterol levels and/or VLDL and LDL cholesterol levels.

As discussed hereinabove, recombinant viruses may be used to introduce both DNA encoding LIPG and subfragments of LIPG as well as antisense nucleic acids. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

Ribozymes according to the present invention may be administered in amounts ranging from about 5 to about 50 mg/kg/day in a pharmaceutically acceptable carrier. Dosage levels may be adjusted based on the measured therapeutic efficacy.

Appropriate levels of inhibitor or enhancer molecules may be determined by qualified medical personnel using the parameters discussed above.

The present invention provides compositions and methods for increasing the level of HDL cholesterol and apolipoprotein AI and lowering the levels of VLDL and LDL cholesterol in a patient. The present invention further provides methods of treating a human or other animal having an undesirable lipid profile, wherein said undesirable lipid profile is the result of abnormally high expression of LIPG polypeptide activity.

Methods and Compositions for Lowering Levels of LIPG Polypeptide Activity

The methods for decreasing the expression of LIPG polypeptide in order to increase the levels of HDL cholesterol and apolipoprotein AI and correct those conditions in which LIPG polypeptide activity contributes to a disease or disorder associated with an undesirable lipid profile include but are not limited to administration of a composition comprising an antisense nucleic acid, administration of a composition comprising an intracellular binding protein such as an antibody, administration of an inhibitory molecule which inhibits the enzymatic activity of LIPG, for example, a composition comprising an expression vector encoding a subfragment of LIPG, for example, LLGN polypeptide or a small molecular weight molecule, including administration of a small molecular weight compound which down regulates LIPG expression at the level of transcription, translation or post-translation, and administration of a ribozyme which cleaves mRNA encoding LIPG.

Methods Utilizing Antisense Nucleic Acids

In one embodiment, a composition comprising an antisense nucleic acid is used to down-regulate or block the expression of LIPG. In one preferred embodiment, the nucleic acid encodes antisense RNA molecules. In this embodiment, the nucleic acid is operably linked to signals enabling expression of the nucleic acid sequence and is introduced into a cell utilizing, preferably, recombinant vector constructs, which will express the antisense nucleic acid once the vector is introduced into the cell. Examples of suitable vectors includes plasmids, adenoviruses, adeno-associated viruses, retroviruses, and herpes viruses. Preferably, the vector is an adenovirus. Most preferably, the vector is a replication defective adenovirus comprising a deletion in the E1 and/or E3 regions of the virus.

In another embodiment, the antisense nucleic acid is synthesized and may be chemically modified to resist degradation by intracellular nucleases, as discussed above. Synthetic antisense oligonucleotides can be introduced to a cell using liposomes. Cellular uptake occurs when an antisense oligonucleotide is encapsulated within a liposome. With an effective delivery system, low, non-toxic concentrations of the antisense molecule can be used to inhibit translation of the target mRNA. Moreover, liposomes that are conjugated with cell-specific binding sites direct an antisense oligonucleotide to a particular tissue.

Methods Utilizing Neutralizing Antibodies and Other Binding Proteins

In another embodiment, the expression of LIPG is down-regulated or blocked by the expression of a nucleic acid sequence encoding an intracellular binding protein which is capable of selectively interacting with LIPG. WO 94/29446 and WO 94/02610, the contents of which are incorporated herein by reference, disclose cellular transfection with genes encoding an intracellular binding protein. An intracellular binding protein includes any protein capable of selectively interacting, or binding, with LIPG in the cell in which it is expressed and of neutralizing the function of bound LLG. Preferably, the intracellular binding protein is a neutralizing antibody or a fragment of a neutralizing antibody. More preferably, the intracellular binding protein is a single chain antibody.

WO 94/02610 discloses preparation of antibodies and identification of the nucleic acid encoding a particular antibody. Using LIPG or a fragment thereof, a specific monoclonal antibody is prepared by techniques known to those skilled in the art. A vector comprising the nucleic acid encoding an intracellular binding protein, or a portion thereof, and capable of expression in a host cell is subsequently prepared for use in the method of this invention.

Alternatively, LIPG activity can be blocked by administration of a neutralizing antibody into the circulation. Such a neutralizing antibody can be administered directly as a protein, or it can be expressed from a vector (with a secretory signal).

Methods Utilizing an Inhibitory Molecule which Inhibits the Enzymatic Activity of LIPG In another embodiment, LIPG activity is inhibited by the administration of a composition comprising a subfragment of LIPG polypeptide, for example, LLGN. This composition may be administered in a convenient manner, such as by the oral, topical, intravenous, intraperitoneal, intramuscular, subcutaneous, intranasal, or intradermal routes. The composition may be administered directly or it may be encapsulated (e.g. in a lipid system, in amino acid microspheres, or in globular dendrimers). The polypeptide may, in some cases, be attached to another polymer such as serum albumin or polyvinyl pyrrolidone.

In another embodiment, LIPG activity is inhibited through the use of gene therapy, that is, through the administration of a composition comprising a nucleic acid which encodes and directs the expression of a subfragment of LIPG, for example, LLGN.

In another embodiment, LIPG activity is inhibited through the use of inhibitory molecules. These low molecular weight compounds interfere with LIPG's enzymatic properties or prevent its appropriate recognition by cellular binding sites.

In a specific embodiment, the LIPG polypeptide of the present invention also has an affinity for heparin. LIPG polypeptide binding to extracellular heparin in the lumen of blood vessels would permit LIPG to bind to and accelerate LDL uptake by acting as a bridge between LDL and the extracellular heparin. In the localized area of an atherosclerotic lesion, an increased level of lipase activity is hypothesized to accelerate the atherogenic process (Zilversmit, D. B. (1995) Clin. Chem. 41, 153–158; Zambon, A., Torres, A., Bijvoet, S., Gagne, C., Moojani, S., Lupien, P. J., Hayden M. R., and Brunzell, J. D. (1993) Lancet 341, 1119–1121). This may be due to an increase in the binding and uptake of lipoproteins by vascular tissue mediated by lipases (Eisenberg, S., Sehayek, E., Olivecrona, T. Vlodavsky, I. (1992) J. Clin. Invest. 90, 2013–2021; Tabas, I., Li, I., Brocia R. W., Xu, S. W., Swenson T. L. Williams, K. J. (1993) J. Biol. Chem. 268, 20419–20432; Nordestgaard, B. G., and Nielsen, A. G. (1994) Curr. Opin. Lipid. 5, 252–257; Williams, K. J., and Tabas, I. (1995) Art. Thromb. and Vasc. Biol. 15, 551–561). Additionally, a high local level of lipase activity may result in cytotoxic levels of fatty acids and lysophosphatidylcholine being produced in precursors of atherosclerotic lesions. This particular activity of LLG may contribute to the development or progression of atherosclerosis, particularly in the context of excessive lipid levels in a subject due to dietary or genetic factors. Thus, the present invention permits inhibition of lipoprotein accumulation by inhibiting LIPG polypeptide expression or binding to lipoprotein (e.g., LDL).

Methods Utilizing an Inhibitory Molecule which Prevents LIPG Gene Expression

In another embodiment, inhibitory molecules, including small molecular weight compounds, are able to down regulate LIPG expression at the level of transcription, translation or post-translation. In order to identify such inhibitory molecules, the reporter gene systems described above may be used. These inhibitory molecules may be combined with a pharmaceutically acceptable carrier and administered using conventional methods known in the art.

Methods Utilizing Ribozymes

Ribozymes may be administered to cells by encapsulation in liposomes, by iontophoresis, by incorporation into hydrogels, cyclodextrins, biodegradable nanocapsules, and bioadhesive microspheres or by any of a variety of other methods discussed above. The ribozyme may be delivered to a target tissue by direct injection or by use of a catheter, infusion pump or stent. Alternative routes of delivery include intravenous injection, intramuscular injection, subcutaneous injection, aerosol inhalation, oral (tablet or pill form), topical, systemic, ocular, intraperitoneal and/or intrathecal delivery.

In preferred embodiments, a ribozyme-encoding sequence is cloned into a DNA expression vector. Transcription of the ribozyme sequence is driven from an eukaryotic RNA polymerase II (pol II), or RNA polymerase III (pol III) promoter. The expression vector can be incorporated into a variety of vectors including the viral DNA vectors such as adenovirus or adeno-associated virus vectors discussed above.

In a preferred embodiment of the invention, a transcription unit expressing a ribozyme that cleaves LIPG RNA is inserted into an adenovirus DNA viral vector. The vector is delivered as recombinant viral particles and is locally administered to the site of treatment, through the use of a catheter, stent or infusion pump.

Administration of Apolipoprotein AI

In another embodiment, any of the methods discussed above for lowering the levels of LIPG polypeptide activity are utilized in combination with administration of apolipoprotein AI or an expression system capable of expressing apolipoprotein AI in a patient (see, for example, U.S. Pat. No. 5,866,551, which is incorporated herein by reference).

Methods and Compositions for Increasing Levels of LIPG Polypeptide Activity

The methods for increasing the expression or activity of LIPG polypeptide to lower the levels of VLDL and LDL cholesterol include, but are not limited to, administration of a composition comprising the LIPG polypeptide, administration of a composition comprising an expression vector which encodes the LIPG polypeptide, administration of a composition comprising an enhancer molecule which enhances the enzymatic activity of the LIPG polypeptide and administration of an enhancer molecule which increases expression of the LIPG gene.

Methods Utilizing LIPG Polypeptides

In one embodiment, the level of LIPG activity is increased through the administration of a composition comprising the LIPG polypeptide. This composition may be administered in a convenient manner, such as by the oral, topical, intravenous, intraperitoneal, intramuscular, subcutaneous, intranasal, or intradermal routes. The composition may be administered directly or it may be encapsulated (e.g. in a lipid system, in amino acid microspheres, or in globular dendrimers). The polypeptide may, in some cases, be attached to another polymer such as serum albumin or polyvinyl pyrrolidone.

Methods Utilizing Vectors that Express LIPG

In another embodiment, the level of LIPG is increased through the use of gene therapy, that is, through the administration of composition comprising a nucleic acid which encodes and directs the expression of the LIPG polypeptide. In this embodiment, the LIPG polypeptide is cloned into an appropriate expression vector. Possible vector systems and promoters are extensively discussed above. The expression vector is transferred into the target tissue using one of the vector delivery systems discussed above. This transfer is carried out either ex vivo in a procedure in which the nucleic acid is transferred to cells in the laboratory and the modified cells are then administered to the human or other animal, or in vivo in a procedure in which the nucleic acid is transferred directly to cells within the human or other animal. In preferred embodiments, an adenoviral vector system is used to deliver the expression vector. If desired, a tissue specific promoter is utilized in the expression vector as described above.

Non-viral vectors may be transferred into cells using any of the methods known in the art, including calcium phosphate coprecipitation, lipofection (synthetic anionic and cationic liposomes), receptor-mediated gene delivery, naked DNA injection, electroporation and bioballistic or particle acceleration.

Methods Utilizing an Enhancer Molecule which Enhances the Enzymatic Activity of LIPG In another embodiment, the activity of LIPG is enhanced by enhancer molecules that increase the enzymatic activity of LIPG or increase its appropriate recognition by cellular binding sites. These enhancer molecules may be introduced by the same methods discussed above for the administration of polypeptides.

Methods Utilizing an Enhancer Molecule which Increases LIPG Gene Expression

In another embodiment, the level of LIPG is increased through the use of small molecular weight compounds, which can upregulate LIPG expression at the level of transcription, translation, or post-translation. These compounds may be administered by the same methods discussed above for the administration of polypeptides.

Treatment Methods Relating to Impaired Biliary Excretion

Intrahepatic cholestasis can be characterized by increased serum cholesterol and phospholipid levels. A recently described, phalloidin drug-induced intrahepatic cholestasis model in rats demonstrated significant increases in the serum levels of cholesterol and phospholipid (Ishizaki, K., Kinbara, S., Miyazawa, N., Takeuchi, Y., Hirabayashi, N., Kasai, H., and Araki, T. (1997) Toxicol. Letters 90, 29–34). The products of this invention may be used to treat intrahepatic cholestasis in patients that have increased serum cholesterol and/or phospholipid. In addition, this rat model also exhibited a severe decrease in biliary cholesterol excretion rates. The LIPG polypeptide and nucleic acid products of this invention may be used to treat patients with an impaired biliary excretion system.

Intrahepatic cholestasis is also characterized by impaired bile flow from the liver. Recently, the loci for progressive familial intrahepatic cholestasis (PFIC or Byler disease) and benign recurrent intrahepatic cholestasis (BRIC) were mapped to 18q21–q22 (Carlton, V. E. H., Knisely, A. S., and Freimer, N. B. (1995) Hum. Mol. Genet. 4, 1049–1053 and Houwen, R. H., Baharloo, S., Blankenship, K., Raeymaekers, P., Juyn, J., Sandkuijl, L. A., and Freimer, N. B. (1994) Nature Genet. 8, 380–386, respectively). As LLG gene maps within this chromosomal region at 18q21, the LLG gene or products of this invention may be used to treat patients with intrahepatic cholestasis that is caused by a mutation or defective expression of the PFIC/BRIC disease gene(s).

In another embodiment, the LLG gene or polypeptide products of this invention may be used to treat patients with intrahepatic cholestasis that is not due to a defect in the PFIC/BRIC disease gene(s) at 18q21–q22. A recent study suggested that another locus, located outside of the 18q21–q22 region may also produce the PFIC phenotype (Strautnieks, S. S., Kagalwalla, A. F., Tanner, M. S., Gardiner, R. M., and Thompson, R. J. (1996) J. Med. Genet. 33, 833–836). Nevertheless, administration of LLG polypeptide, either directly or via gene therapy, may alleviate this form of the condition.

Methods and Compositions for Diagnosing a Predisposition to Low HDL Levels

Given the ability of LIPG polypeptide to lower the levels of HDL cholesterol and apolipoprotein AI, the level of LIPG polypeptide in the body may be used to determine whether an individual is predisposed to low levels of HDL cholesterol and apolipoprotein AI. In this method, a tissue sample is taken from the patient. The tissue may be blood or one of the tissues which has been demonstrated to express LIPG as discussed in the Examples section. Measurement of the level of LIPG may be performed by a variety of methods known to those of skill in the art. In preferred embodiments, an antibody directed against LIPG polypeptide may be used to measure the level of LIPG in a tissue sample.

EXAMPLES

The following examples illustrate the invention. These examples are illustrative only, and do not limit the scope of the invention.

Example 1

Identification of a Differentially Expressed cDNA

RNA Preparation

Human monocytic THP-1 cells (Smith, P. K., Krohn, R. I., Hermanson, G. T., Mallia, A. K., Gartner, F. H. Provenzano, M. D., Fujimoto, E. K., Goeke, N. M., Olson, B. J., and Klenk, D. C. (1985) Anal. Biochem. 150, 76–85) were cultured in RPMI-1640 medium (GIBCO) with 25 mM HEPES, 10% fetal bovine serum, 100 units/ml penicillin G sodium and 100 units/ml streptomycin sulfate. Cells were plated onto 15 cm tissue culture dishes at $1.5 \times 10^7$ cells/plate, and treated with 40 ng/ml phorbol 12-myristate 13-acetate (Sigma) for 48 hours to induce differentiation of the cells. Human low density lipoproteins (LDL) were purchased from Calbiochem, and were dialyzed exhaustively versus PBS at 4° C. The LDL was then diluted to 500 µg/ml and dialyzed versus 5 µM $CuSO_4$ in PBS at 37° C. for 16 hours. To stop oxidation, the LDL was dialyzed exhaustively versus 150 mM NaCl, 0.3 mM EDTA, then filter sterilized. Protein concentration was determined by the BCA method (Schuh, J. Fairclough, G. F., and Haschemeyer, R. H. (1978) Proc. Natl. Acad. Sci. USA 75, 3173–3177) (Pierce). The degree of oxidation was determined by TBARS (Chomczynski, P. (1993) Biotechniques 15, 532–537), and was between 25–30 nmol MDA equivalents/mg protein. The differentiated THP-1 cells were exposed for 24 hours to either 50 µg/ml oxidized LDL or NaCl-EDTA buffer in RPMI medium with 10% lipoprotein-deficient fetal bovine serum (Sigma). To harvest the RNA, the plates were rinsed with 10 ml of PBS, then 14 ml of TRIZOL (Liang, P. and Pardee, A. B. (1992) Science 257, 967–971) (GIBCO) were added to each plate. The solution was pipetted several times to mix, then like samples were pooled into centrifuge tubes and 3 ml chloroform per plate were added and mixed. The tubes were centrifuged for 15 minutes at 12000×g. After centrifugation the upper layer was transferred to a new tube and 7.5 ml isopropanol per plate was added and mixed. The tubes were centrifuged at 12000×g for 20 minutes. The pellet was rinsed with ice-cold 70% ethanol and dried at room temperature. The pellets were suspended in 500 µl TE (Tris-EDTA) and treated with 200 units RNase-free DNAse 1 and 200 units RNasin placental RNase inhibitor (Promega) for 30 minutes at 37° C. The RNA was purified by sequential extractions with phenol, phenol/chloroform/isoamyl alcohol (25:24:1), and chloroform/isoamyl alcohol (24:1) followed by ethanol precipitation.

cDNA Synthesis cDNA synthesis and PCR amplification were accomplished using protocols from the Differential Display Kit, version 1.0 (Display Systems Biotechnology, Inc.) This system is based on the technique originally described by Liang and Pardee (Mead, D. A., Pey, N. K., Herrnstadt, C., Marcil, R. A., and Smith, L. M., (1991) Bio/Technology 9, 657–663). The primer pairs which yielded the cDNA fragment containing the first information of the lipase like gene were downstream primer 7 and upstream primer 15. The cDNA for the amplification was synthesized as follows, using RNA derived from PMA treated THP-1 cells exposed to either buffer or oxidized LDL: 3 µl of 25 µM downstream primer 7 and 7.5 µl of diethylpyrocarbonate (DEPC)-treated water were added to 300 ng (3.0 µl) RNA from either sample of THP-1 RNA. This was heated to 70° C. for 10 minutes then chilled on ice. To this tube were added 3 µl of 5×PCR buffer (250 mM Tris-HCl pH 8.3, 375 mM KCl)(GIBCO), 3 µl 25 mM $MgCl_2$, 3 µl 0.1M DTT, 1.2 µl 500 µM dNTPs, 0.7 µl RNasin, and 5.6 µl DEPC-treated water. The tubes were incubated for 2 minutes at room temperature, after which 1.5 µl (300 units) Superscript II RNase H-reverse transcriptase (GIBCO) were added. The tubes were incubated sequentially at room temperature for 2 minutes, 60 minutes at 37° C., and 5 minutes at 95° C., followed by chilling on ice. PCR amplification was performed using a master mix containing 117 µl 10×PCR buffer (500 mM KCl, 100 mM Tris-HCl pH 8.3, 15 mM $MgCl_2$, and 0.01% (w/v) gelatin), 70.2 µl 25 mM $MgCl_2$, 5.9 µl alpha-$^{33}$P dATP (10 m Ci/ml, DuPont NEN), 4.7 µl 500 µM dNTP mix, 11 µl AmpliTaq DNA polymerase (5 units/µl, Perkin-Elmer), and 493.3 µl DEPC-treated water. For each reaction, 12 µl of the master mix was added to 2 µl downstream primer #7, 1 µl of cDNA, and 5 µl of upstream primer #15. The reaction mixes were heated to 94° C. for 1 minute, then thermocycled 40 times with a denaturing step of 94° C. for 15 seconds, annealing step of 40° C. for 1 minute, and an extension step of 72° C. for 30 seconds. Following the 40 cycles, the reactions were incubated at 72° C. for 5 minutes and stored at 10° C. The PCR reactions were performed in a Perkin-Elmer GeneAmp System 9600 thermocycler.

Four microliters of the amplification reaction were mixed with an equal volume of loading buffer (0.2% bromphenol blue, 0.2% Xylene cyanol, 10 mM EDTA pH 8.0, and 20% glycerol). Four microliters of this mix was run on a 6% nondenaturing acrylamide sequencing format gel for 3 hours at 1200 volts (constant voltage). The gel was dried at 80° C. for 1.5 hours and exposed to Kodak XAR film. An amplification product found only in the reaction containing cDNA from THP-1 cells exposed to oxidized LDL was identified and excised from the gel. 100 µl of DEPC-treated water was added to a microcentrifuge tube containing the excised gel fragment and was incubated for 30 minutes at room temperature followed by 15 minutes at 95° C.

To reamplify the PCR product, 26.5 microliters of the eluted DNA were used in a amplification reaction that also included 5 µl 10×PCR buffer, 3 µl 25 mM $MgCl_2$, 5 µl 500 µM dNTPs, 5 µl 2 µM downstream primer 7, 7.5 µl upstream primer 15, and 0.5 µl Amplitaq polymerase. The PCR cycling parameters and instrument were as described above. Following amplification, 20 µl of the reamplification was analyzed on an agarose gel and 4 µl was used to subclone the PCR products into the vector pCRII using the TA cloning system (Frohman, M. A., Dush, M. K., and Martin, G. R. (1988) Proc. Natl. Acad. Sci. USA 85, 8998–9002) (Invitrogen). Following an overnight ligation at 14° C., the ligation products were used to transform E. coli. Resulting transformants were picked and 3 ml overnight cultures were used in plasmid minipreparations. Insert sizes were determined using EcoRI digestions of the plasmids and clones containing inserts of the approximate size of the original PCR product were sequenced using fluorescent dye-terminator reagents (Prism, Applied Biosystems) and an Applied Biosystems 373 DNA sequencer. The sequence of the PCR product is SEQ ID NO. 1. The sequence of the amplification primers is underlined.

5'RACE Reaction

1 µl (1 µg) of RNA was combined with 3 µl (3 pmol) primer 2a and 11 µl DEPC-treated water and heated to 70° C. for 10 minutes followed by 1 minute on ice. 2.5 µl 10× reaction buffer (200 mM Tris-HCl pH 8.4, 500 mM KCl), 3 µl 25 mM $MgCl_2$, 1 µl 10 mM dNTP mix, and 2.5 µl 0.1 M DTT were added. The mix was incubated at 42° C. for 2 minutes, then 1 µl Superscript II reverse transcriptase was added. The reaction was incubated for an additional 30 minutes at 42° C., 15 minutes at 70° C., and on ice for 1 minute. One microliter of RNase H (2 units) was added and the mixture was incubated at 55° C. for 10 minutes. The cDNA was purified using the GlassMax columns (Sambrook, J. Fritsch, E. F., and Maniatis, T. (1989) Molecular Cloning: A Laboratory Manual, second edition, Cold Spring Harbor Laboratory Press, Plainview, N.Y.) included in the kit. The cDNA was eluted from the column in 50 µl $dH_2O$, lyophilized, and resuspended in 21 µl $dH_2O$. Tailing of the cDNA was accomplished in the following reaction: 7.5 µl $dH_2O$, 2.5 µl reaction buffer (200 mM Tris-HCl pH 8.4, 500 mM KCl), 1.5 µl 25 mM $MgCl_2$, 2.5 µl 2 mM dCTP, and 10 µl of the cDNA were incubated at 94° C. for 3 minutes, then 1 minute on ice. 1 µl (10 units) of terminal deoxynucleotidyl transferase was added and the mixture was incubated for 10 minutes at 37° C. The enzyme was heat inactivated by incubation at 70° C. for 10 minutes and the mixture was placed on ice. PCR amplification of the cDNA was performed in the following steps: 5 µl of the tailed cDNA was included in a reaction which also contained 5 µl 10×PCR buffer (500 mM KCl, 100 mM Tris-HCl pH 8.3, 15 mM $MgCl_2$, and 0.01% (w/v) gelatin), 1 µl 10 mM dNTP mix, 2 µl (10 pmol) anchor primer, 1 µl (20 pmol) primer 3a, and 35 µl $dH_2O$. The reaction was heated to 95° C. for 1 minute, then 0.9 µl (4.5 units) Amplitaq polymerase was added. The reaction was cycled 40 times under the following conditions: 94° C. for 5 seconds, 50° C. for 20 seconds, and 72° C. for 30 seconds. One microliter of this reaction was used in a nested reamplification to increase levels of specific product for subsequent isolation. The reamplification included: 1 µl primary amplification, 5 µl 10×PCR buffer, 1 µl 10 mM dNTP mix, 2 µl (20 pmol) universal amplification primer, 2 µl (20 pmol) primer 4a, and 38 µl $dH_2O$. The reaction was heated to 95° C. for 1 minute, then 0.7 µl (3.5 units) Amplitaq polymerase was added. The reaction was cycled 40 times under these conditions; 94° C. for 5 seconds, 50° C. for 20 seconds, and 72° C. for 30 seconds. The amplification products were analyzed via 0.8% agarose gel electrophoresis. A predominant product of approximately 1.2 kilobase pairs was detected. Two microliters of the reaction products were cloned into the pCRII vector from the TA cloning kit (Invitrogen) and incubated at 14° C. overnight. The ligation products were used to transform E. coli. The insert sizes of the resulting transformants were determined following EcoRI digestion. Clones containing inserts of the approximate size of the PCR product were sequenced using fluorescent dye-terminator reagents (Prism, Applied Biosystems) and an Applied Biosystems 373 DNA sequencer. The sequence of the RACE product including the EcoRI sites from the TA vector is SEQ ID NO. 3.

Example 2

Cloning and Chromosomal Localization of the LIPG Gene cDNA Library Screening

A human placental cDNA library (Oligo dT and random primed, Cat #5014b, Lot #52033) was obtained from Clontech (Palo Alto, Calif.). A radiolabeled probe was created by excising the insert of a plasmid containing the 5'RACE reaction PCR product described above. The probe was radiolabeled using the random priming technique: the DNA fragment (50–100 ng) was incubated with 1 µg of random hexamers (Gibco) at 95° C. for 10 minutes followed by 1 minute on ice. At room temperature the following were added: 3 µl 10× Klenow buffer (100 mM Tris-HCl pH 7.5, 50 mM $MgCL_2$, 57 mM dithiothreitol; New England Biolabs), 3 µl 0.5 mM dATP, dGTP, dTTP), 100 µCi α-$^{32}$PdCTP (3000 Ci/mmol, New England Nuclear), and 1 µl Klenow fragment of DNA polymerase I (5 units, Gibco). The reaction was incubated for 2–3 hours at room temperature and the reaction was then stopped by increasing the volume to 100 µl with TE pH 8.0 and adding EDTA to a final concentration of 1 mM. The unincorporated nucleotides were removed by raising the reaction volume to 100 µl and passing over a G-50 spin column (Boehringer Mannheim). The resulting probes had a specific activity greater than $5 \times 10^8$ cpm/µg DNA.

The library was probed using established methods (Walter, P., Gilmore, R., and Blobel, G. (1984) Cell 38, 5–8). Briefly, the filters were hybridized for 24 hours at 65° C. in 4.8×SSPE (20×SSPE=3.6 M NaCl, 0.2 M $NaH_2PO_4$, 0.02 M EDTA, pH 7.7), 20 mM Tris-HCl pH 7.6, 1× Denhardt's solution (100×=2% Ficoll 400, 2% polyvinylpyrrolidone, 2% BSA), 10% dextran sulfate, 0.1% SDS, 100 µg/ml salmon sperm DNA, and $1 \times 10^6$ cpm/ml radiolabelled probe. Filters were then washed three times for 15 minutes at room temperature in 2×SSC (1×SSC=150 mM NaCl, 15 mM sodium citrate pH 7.0), 0.1% sodium dodecyl sulfate (SDS) followed by three washes for 15 minutes each at 65° C. in 0.5×SSC, 0.1% SDS. Phage which hybridized to the probe were isolated and amplified. DNA was purified from the amplified phage using LambdaSorb reagent (Promega) according to the manufacturer's instructions. The inserts were excised from the phage DNA by digestion with EcoRI. The inserts were subcloned into the EcoRI site of a plasmid vector (Bluescript II SK, Stratagene). The sequence of the open reading frame contained within the 2.6 kb EcoRI fragment of the cDNA was determined by automated sequencing as described above. The sequence is SEQ ID NO. 5. The amino acid sequence of the predicted protein encoded by the open reading frame is SEQ ID NO. 6 and has been termed LLGXL. The first methionine is predicted to be encoded by nucleotide pairs 252–254. The predicted protein is 500 amino acids in length. The first 18 amino acids form a sequence characteristic of a secretory signal peptide (Higgins, D. G., and Sharp, P. M. (1988) Gene 73, 237–244). The propeptide is predicted to have a molecular weight of 56,800 Daltons. Assuming cleavage of the signal peptide at position 18, the unmodified mature protein has a molecular weight of 54,724 Daltons.

TABLE 1

Similarity of triacylglycerol lipase gene family

|       | LLGXL | LPL  | HL   | PL   | PLRP1 | PLRP2 |
|-------|-------|------|------|------|-------|-------|
| LLGXL | —     | 42.7 | 36.5 | 24.5 | 22.5  | 22.6  |
| LPL   | 42.7  | —    | 40.0 | 22.8 | 22.7  | 20.9  |
| HL    | 36.5  | 40.0 | —    | 22.8 | 24.0  | 22.0  |
| PL    | 24.5  | 22.8 | 22.8 | —    | 65.2  | 62.2  |
| PLRP1 | 22.5  | 22.7 | 24.0 | 65.2 | —     | 61.7  |
| PRLP2 | 22.6  | 20.9 | 22.0 | 62.2 | 61.7  | —     |

Percent similarity was based on pairwise alignment using the Clustal algorithm (Camps, L., Reina, M., Llobera, M., Vilaro, S., and Olivecrona, T. (1990) Am. J. Physiol. 258, C673–C681) in the Megalign program of the Lasergene Biocomputing Software Suite (Dnastar).

Chromosomal Localization

DNA from a P1 clone (Sternberg, N., Ruether, J. and DeRiel, K. The New Biologist 2:151–62, 1990) containing genomic LLG DNA was labelled with digoxigenin UTP by nick translation. Labelled probe was combined with sheared human DNA and hybridized to PHA stimulated peripheral blood lymphocytes from a male donor in a solution containing 50% formamide, 10% dextran sulfate, and 2×SSC. Specific hybridization signals were detected by incubating the hybridized cells in fluoresceinated antidigoxigenin antibodies followed by counterstaining with DAPI. This initial experiment resulted in specific labeling of a group E chromosome, which was believed to be chromosome 18 on the basis of DAPI staining.

A second experiment was conducted in which a biotin labelled probe specific for the centromere of chromosome 18 was cohybridized with the LLG probe. This experiment resulted in the specific labeling of the chromosome 18 centromere in red and the long arm of chromosome 18 in green. Measurements of 11 specifically labelled hybridized chromosomes 18 demonstrated that LLG has a Flter of 0.67 (Franke measurement of 0.38), which corresponds to band 18q21. Several genetic diseases, including intrahepatic cholestasis, cone rod dystrophy, and familial expansile osteolysis, are believed to involve defects in this chromosomal region.

Example 3

LIPG RNA Analysis

Expression of LIPG RNA in THP-1 Cells

Figure 8:
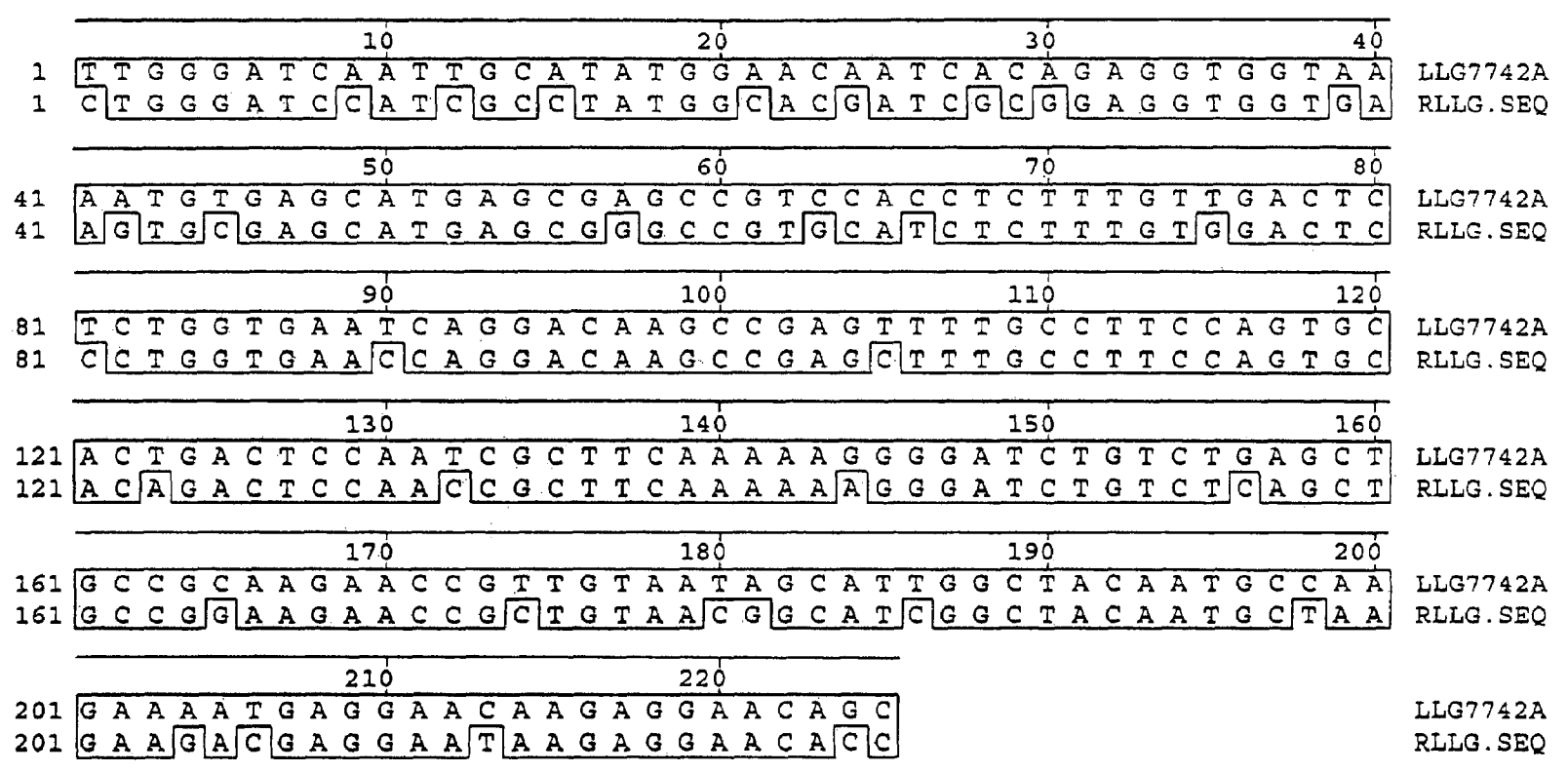

A commercially prepared filter containing 3 μg each of mRNAs from human tissues (heart, brain, placenta, lung, liver, skeletal muscle, kidney, and pancreas) was obtained from Clontech (Catalog #7760-1). This filter was probed and processed as described above. After probing with the radiolabeled LLG fragment and autoradiography, the probe was stripped by washing in boiling 0.1×SSC, 0.1% SDS for 2×15 min. in a 65° C. incubator. The membranes were then probed with a 1.4 kilobase pair DNA fragment encoding human lipoprotein lipase. This fragment was obtained by RT-PCR of the THP-1 RNA (PMA and oxLDL treated) using the 5'LPL and 3'LPL primers depicted in SEQ ID NOS. 20 and 21, respectively, and the RT-PCR conditions described above. After autoradiography, the membranes were stripped again and reprobed with a radiolabeled fragment of the human beta actin cDNA to normalize for RNA content. The results of these analyses are shown in FIG. 8. The highest levels of LIPG message were detected in placental RNA, with lower levels found in RNAs derived from lung, liver, and kidney tissue. In agreement with previous studies by others (Verhoeven, A. J. M., Jansen, H. (1994) Biochem. Biophys. Acta 1211, 121–124), lipoprotein lipase message was found in many tissues, with highest levels found in heart and skeletal muscle tissue. Results of this analysis indicates that the tissue distribution of LIPG expression is very different from that of LPL. The pattern of LIPG expression is also different from that of either hepatic lipase or pancreatic lipase, as reported by others (Wang, C.-S., and Hartsuck, J. A. (1993) Biochem. Biophys. Acta 1166, 1–19; Semenkovich, C. F., Chen, S.-W., Wims, M., Luo C.-C., Li, W.-H., and Chan, L. (1989) J. Lipid Res. 30, 423–431; Adams, M. D., Kerlavage, A. R., Fields, C., and Venter, C. (1993) Nature Genet. 4, 256–265).

A probe was made by excising the insert of a plasmid containing the 5'RACE reaction PCR product described above. The probe was radiolabeled using the random priming technique described in Example 2.

Figure 7:
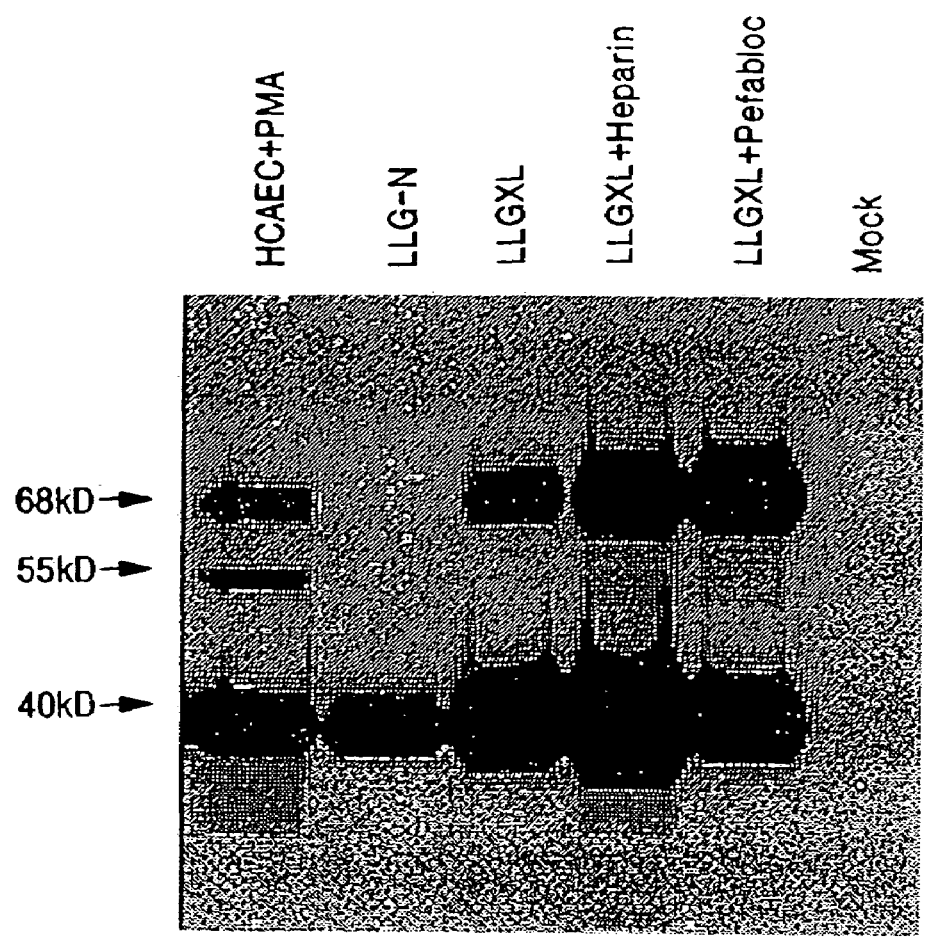

The filters were prehybridized in QuikHyb rapid hybridization solution (Stratagene) for 30 minutes at 65° C. The radiolabeled probe (1–2×10$^6$ cpm/ml) and sonicated salmon sperm DNA (final concentration 100 μg/ml) were denatured by heating to 95° C. for 10 minutes and quick-chilled on ice before adding to the filter in QuikHyb. Hybridization was for 3 hours at 65° C. The unhybridized probe was removed by washing the filters two times for 15 minutes with 2×SSC, 0.1% sodium dodecyl sulfate at room temperature followed by two times for 15 minutes in 0.1×SSC, 0.1% SDS at 62° C. Following the washes, the filters were allowed to dry briefly and then exposed to Kodak XAR-2 film with intensifying screens at −80° C. The results are shown in FIG. 7, which shows a major mRNA species of approximately 4.5 kilobases. Minor species of 4.3 and 1.6 kilobases are also present. The expected size of the LLGN cDNA is 1.6 kb. The LLGXL sequence is likely to be encoded by the major species of mRNA detected.

Expression of LIPG RNA in Various Human Tissues

A commercially prepared filter containing 3 μg each of mRNAs from human tissues (heart, brain, placenta, lung, liver, skeletal muscle, kidney, and pancreas) was obtained from Clontech (Catalog #7760-1). This filter was probed and processed as described above. After probing with the radiolabeled LLG fragment and autoradiography, the probe was stripped by washing in boiling 0.1×SSC, 0.1% SDS for 2×15 min. in a 65° C. incubator. The membranes were then probed with a 1.4 kilobase pair DNA fragment encoding human lipoprotein lipase. This fragment was obtained by RT-PCR of the THP-1 RNA (PMA and oxLDL treated) using the 5'LPL and 3'LPL primers described in FIG. 1. and the RT-PCR conditions described above. After autoradiography, the membranes were stripped again and reprobed with a radiolabeled fragment of the human beta actin cDNA to normalize for RNA content. The results of these analyses are shown in FIG. 8. The highest levels of LIPG message were detected in placental RNA, with lower levels found in RNAs derived from lung, liver, and kidney tissue. In agreement with previous studies by others (Verhoeven, A. J. M., Jansen, H. (1994) Biochem. Biophys. Acta 1211, 121–124), lipoprotein lipase message was found in many tissues, with highest levels found in heart and skeletal muscle tissue. Results of this analysis indicates that the tissue distribution of LIPG expression is very different from that of LPL. The pattern of LIPG expression is also different from that of either hepatic lipase or pancreatic lipase, as reported by others (Wang, C.-S., and Hartsuck, J. A. (1993) Biochem. Biophys. Acta 1166, 1–19; Semenkovich, C. F., Chen, S.-W., Wims, M., Luo C.-C., Li, W.-H., and Chan, L. (1989) J. Lipid Res. 30, 423–431; Adams, M. D., Kerlavage, A. R., Fields, C., and Venter, C. (1993) Nature Genet. 4, 256–265).

To determine the expression pattern in additional human tissues, another commercially prepared membrane was probed with LLGXL cDNA. This dot blot (Human RNA Master Blot, Clontech Cat. # 7770-1) contains 100–500 ng mRNA from 50 different tissues and is normalized for equivalent housekeeping gene expression (Chen, L., and Morin, R. (1971) Biochim. Biophys. Acta 231,194–197). A 1.6 kb DraI-SrfI fragment of the LLGXL cDNA was labeled with $^{32}$PdCTP using a random oligonucleotide priming system (Prime It II, Stratagene) according to the manufacturer's instructions. After 30 minutes prehybridization at 65° C., the probe was added to QuikHyb hybridization solution at $1.3 \times 10^6$ cpm/ml. Hybridization was for 2 hours at 65° C. The unhybridized probe was removed by washing the filters two times for 15 minutes with 2×SSC, 0.1% sodium dodecyl sulfate at room temperature followed by two times for 15 minutes in 0.1×SSC, 0.1% SDS at 62° C. Following the washes, the filters were allowed to dry briefly and then exposed to Kodak XAR-2 film with intensifying screens at −80° C. for varying amounts of time. The resulting images were quantitated by densitometry. The results are shown in Table 2. The relative expression levels of tissues represented in both the multiple tissue northern and the multiple tissue dot blot are similar, with highest levels in placenta, and lower levels in lung, liver and kidney. Fetal liver, kidney, and lung also express roughly the same levels as the adult tissues. Surprisingly, thyroid tissue expression levels were the highest of all tissues represented, with expression of 122% of that in placental tissue. While there is precedence for lipase expression by the placenta (Rothwell, J. E., Elphick, M. C. (1982) J. Dev. Physiol. 4, 153–159; Verhoeven, A. J. M., Carling D., and Jansen H. (1994) J. Lipid Res. 35, 966–975; Burton, B. K., Mueller, H. W. (1980) Biochim. Biophys. Acta 618, 449–460), the thyroid was not previously known to express any lipase. These results suggest that LIPG expression may be involved in maintenance of the placenta, where LIPG may serve to liberate free fatty acids from substrates such as phospholipids as a source of energy. The LIPG expressed in the thyroid may provide precursors for the synthesis of bioactive molecules by that gland.

TABLE 2

Expression of LIPG mRNA in various human tissues

| | |
|---|---|
| whole brain | N.D. |
| amygdala | N.D. |
| caudate nucleus | N.D. |
| cerebellum | 4 |
| cerebral cortex | N.D. |
| frontal lobe | N.D. |
| hippocampus | N.D. |
| medulla oblongata | N.D. |
| occipital lobe | N.D. |
| putamen | N.D. |
| substantial nigra | N.D. |
| temporal lobe | N.D. |
| thalamus | N.D. |
| sub-thalamic nucleus | N.D. |
| spinal cord | N.D. |
| heart | N.D. |
| aorta | N.D. |
| skeletal muscle | N.D. |
| colon | 8 |
| bladder | N.D. |
| uterus | N.D. |
| prostate | 5 |
| stomach | N.D. |
| testes | 9 |
| ovary | N.D. |
| pancreas | N.D. |
| pituitary gland | N.D. |
| adrenal gland | N.D. |
| thyroid gland | 122 |
| salivary gland | N.D. |
| mammary gland | N.D. |
| kidney | 44 |
| liver | 61 |
| small intestine | 6 |
| spleen | N.D. |
| thymus | N.D. |
| peripheral leukocyte | N.D. |
| lymph node | N.D. |
| bone marrow | N.D. |
| appendix | 7 |
| lung | 29 |
| trachea | 12 |
| placenta | 100 |
| fetal brain | 5 |
| fetal heart | N.D. |
| fetal kidney | 56 |
| fetal liver | 14 |
| fetal spleen | N.D. |
| fetal thymus | N.D. |
| fetal lung | 8 |

Values given are percentage of expression with levels in placental tissue arbitrarily set at 100%. Values are average of densitometric measurements from two autoradiographic exposures. N.D.=not detectable.

Expression of LIPG RNA in Cultured Endothelial Cells

Figure 4:
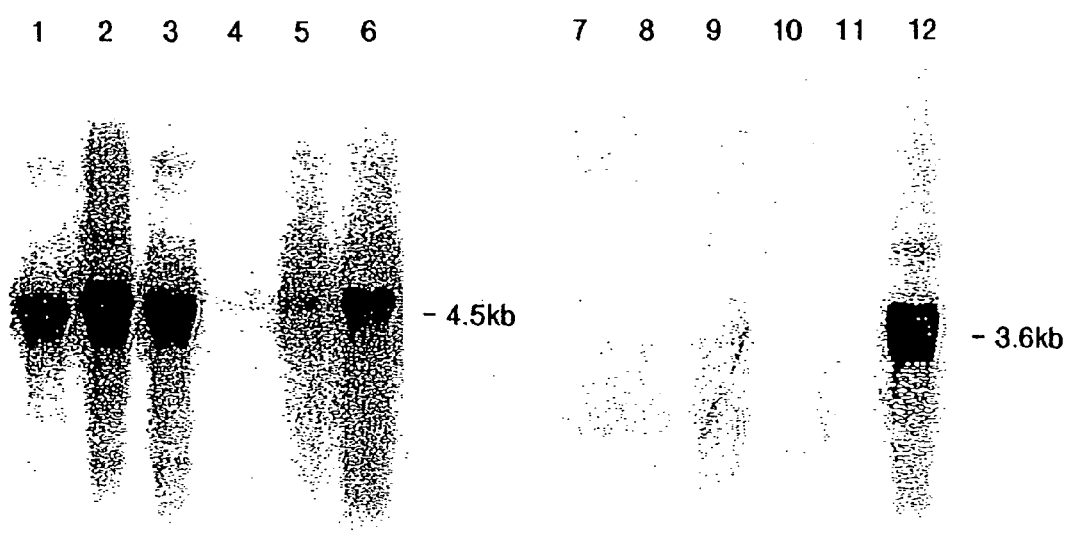

Human umbilical vein endothelial cells (HUVEC) and human coronary arterial endothelial cells (HCAEC) were obtained from Clonetics. HUVECs were propagated in a commercially prepared endothelial cell growth medium (EGM, Clonetics) supplemented with 3 mg/ml bovine brain extract (Maciag, T., Cerundolo, J., Ilsley, S., Kelley, P. R., and Forand, R. (1979) Proc. Natl. Acad. Sci. USA 76, 5674–5678), Clonetics), while HCAECs were propagated in EGM supplemented with 3 mg/ml bovine brain extract and 3% fetal bovine serum (5% final concentration). Cells were grown to confluence, then the medium was changed to EGM without bovine brain extract. Cultures were stimulated by adding 100 ng/ml of phorbol myristate (Sigma). After 24 hours incubation, the RNAs were extracted from the cells via the Trizol method described above. Twenty micrograms of total RNA was electrophoresed and transferred to the membrane for analysis. The membranes were probed with LIPG and LPL probes as described above. The results are shown in FIG. 4. Twenty micrograms of total RNA from THP-1 cells stimulated with PMA was run on the blot for comparison. RNA hybridizing to the LIPG probe was detected in unstimulated and PMA stimulated HUVEC cells. In contrast, detectable levels of LIPG mRNA were only found in HCAEC cultures after stimulation with PMA. In agreement with previous studies of others, no detectable lipoprotein lipase mRNA was detected in any of the endothelial RNAs (Verhoeven, A. J. M., Jansen, H. (1994) Biochem. Biophys. Acta 1211, 121–124).

Example 4

LIPG Protein Analysis

Antibody Preparation

Antisera were generated to peptides with sequences corresponding to a region of the predicted protein encoded by the LIPG cDNA open reading frame. This peptide was chosen because of its high predicted antigenicity index (Jameson B. A., and Wolf, H. (1988) Comput. Applic. in the Biosciences 4, 181–186). The sequence of the immunizing peptide was not found in any protein or translated DNA sequence in the Genbank database. Its corresponding position in the LIPG protein is shown in FIG. 5. The carboxy terminal cysteine of the peptide does not correspond to the residue in the LIPG putative protein, but was introduced to facilitate coupling to the carrier protein. The peptide was synthesized on a Applied Biosystems Model 433A peptide synthesizer. Two milligrams of peptide was coupled to two milligrams of maleimide-activated keyhole limpet hemocyanin following the protocols included in the Imject Activated Immunogen Conjugation Kit (Pierce Chemical). After desalting, one-half of the conjugate was emulsified with an equal volume of Freund's complete adjuvant (Pierce). This emulsification was injected into a New Zealand White rabbit. Four weeks after the initial inoculation, a booster inoculation was made with an emulsification made exactly as described above except Freund's incomplete adjuvant (Pierce) was used. Two weeks after the boost, a test bleed was made and titers of specific antibodies were determined via ELISA using immobilized peptide. A subsequent boost was made one month after the first boost.

Western Analysis of Medium from Endothelial Cell Cultures

Figure 6:
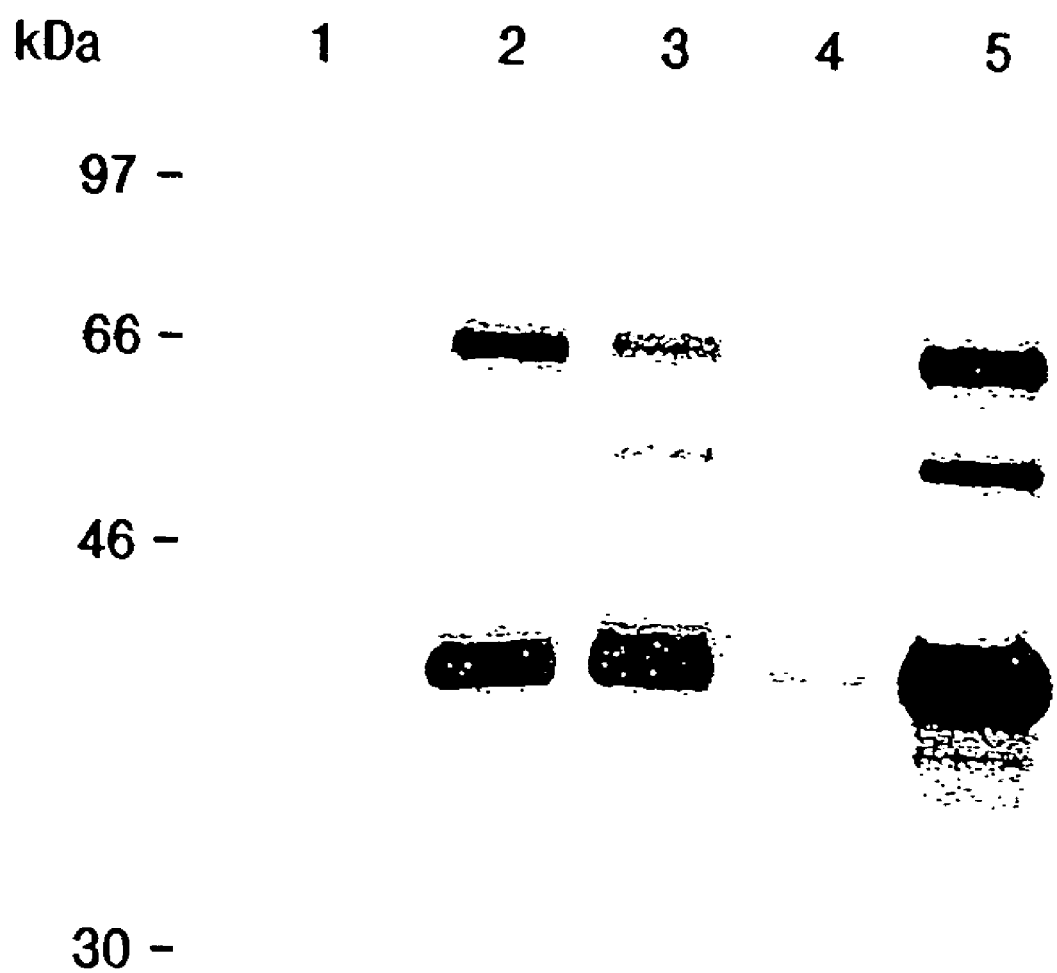

HUVEC and HCEAC cells were cultured and stimulated with PMA as described in Example 3C, except that the cells were stimulated with PMA for 48 hours. Samples of conditioned medium (9 ml) were incubated with 500 μl of a 50% slurry of heparin-Sepharose CL-6B in phosphate buffered saline (PBS, 150 mM sodium chloride, 100 mM sodium phosphate, pH 7.2). Heparin-Sepharose was chosen to partially purify and concentrate the LIPG proteins because of the conservation of residues in the LLGXL sequence which have been identified as critical for the heparin-binding activity of LPL (Ma, Y., Henderson, H. E., Liu, M.-S., Zhang, H., Forsythe, I. J., Clarke-Lewis, I., Hayden, M. R., and Brunzell, J. D. J. Lipid Res. 35, 2049–2059; and FIG. 1.). After rotation at 4° C. for 1 hour, the samples were centrifuged for 5 minutes at 150×g. The medium was aspirated and the Sepharose was washed with 14 ml PBS. After centrifugation and aspiration, the pelleted heparin-Sepharose was suspended in 200 μl 2×SDS loading buffer (4% SDS, 20% glycerol, 2% β-mercaptoethanol, 0.002% bromphenol blue, and 120 mM Tris pH 6.8). The samples were heated to 95° C. for 5 minutes and 40 μl was loaded onto a 10% Tris-Glycine SDS gel. After electrophoresis at 140 V for approximately 90 minutes, the proteins were transferred to nitrocellulose membranes via a Novex electroblotting apparatus (210 V, 1 hour). The membranes were blocked for 30 minutes in blocking buffer (5% nonfat dried milk, 0.1% Tween 20, 150 mM sodium chloride, 25 mM Tris pH 7.2). Antipeptide antisera and normal rabbit serum was diluted 1:5000 in blocking buffer and was incubated with the membranes overnight at 4° C. with gentle agitation. The membranes were then washed 4×15 minutes with TBST (0.1% Tween 20, 150 mM sodium chloride, 25 mM Tris pH 7.2). Goat anti-rabbit peroxidase conjugated antisera (Boehringer Mannheim) was diluted 1:5000 in blocking buffer and incubated with the membrane for 1 hour with agitation. The membranes were washed as above, reacted with Renaissance chemiluminescent reagent (DuPont NEN), and exposed to Kodak XAR-2 film. The results are shown in FIG. 6. Two species of immunoreactive proteins are present in the samples from unstimulated HUVEC and HCAEC cells. Levels of immunoreactive protein in the unstimulated HCAEC samples are much lower than the corresponding HUVEC sample. Upon stimulation with PMA, three immunoreactive proteins are secreted by the endothelial cell cultures. PMA exposure greatly increased the level of LIPG proteins produced by the HCAEC cultures. PMA induction of LLG proteins was not as dramatic in the HUVEC cultures.

Example 5

Recombinant LIPG Protein Production

LIPG Expression Constructs

The cDNAs encoding the LLGN and LLGXL proteins were cloned into the mammalian expression vector pCDNA3 (Invitrogen). This vector allows expression of foreign genes in many mammalian cells through the use of the cytomegalovirus major late promoter. The LLGN 5'RACE product was cloned into the EcoRI site of pcDNA3. The LLGXL cDNA was digested with DraI and SrfI to yield a 1.55 kb cDNA (SEQ ID NO. 5). The vector was digested with the restriction enzyme EcoRV and the vector and insert were ligated using T4 DNA ligase and reagents from the Rapid Ligation Kit (Boehringer Mannheim) according to the manufacturers instructions. The ligation products were used to transform competent E. coli. Resultant colonies were screened by restriction analysis and sequencing for the presence and orientation of the insert in the expression vector.

Transient Transfection of LIPG in COS-7 Cells

The LIPG expression vectors were introduced into COS-7 cells through the use of Lipofectamine cationic lipid reagent (GIBCO). Twenty-four hours before the transfection, COS-7 cells were plated onto 60 mm tissue culture dishes at a density of $2 \times 10^5$ cells/plate. The cells were propagated in Dulbecco's modified Eagle's medium (DMEM; GIBCO) supplemented with 10% fetal calf serum, 100 U/ml penicillin, 100 μg/ml streptomycin. One microgram of plasmid DNA was added to 300 μl of Optimem I serum-free medium (Gibco). Ten microliters of Lipofectamine reagent were diluted into 300 μl of Optimem I medium and this was combined with the DNA solution and allowed to sit at room temperature for 30 minutes. The medium was removed from the plates and the cells were rinsed with 2 ml of Optimem medium. The DNA-Lipofectamine solution was added to the plates along with 2.7 ml Optimem medium and the plates were incubated for 5 hours at 37° C. After the incubation, the serum free medium was removed and replaced with DMEM supplemented with 2% FBS and antibiotics. Twelve hours post-transfection, some of the cultures were treated with either 0.25 mM Pefabloc SC (Boehringer Mannheim), a protease inhibitor, or 10 U/ml heparin. Thirty minutes before harvest, the heparin treated samples were treated with an additional 40 U/ml heparin. The medium was removed from the cells 60 hours after transfection. Heparin-Sepharose CL-4B (200 μl of a 50% slurry in PBS pH 7.2) was added to 1 ml of medium and was mixed at 4° C. for 1 hour. The Sepharose was pelleted by low speed centrifugation and was washed three times with 1 ml cold PBS. The Sepharose was pelleted and suspended in 100 μl 2× loading buffer. The samples were heated to 95° C. for 5 minutes. 40 μl of each sample was loaded onto a 10% SDS-PAGE gel. Electrophoresis and western analysis was performed using the anti-LIPG antiserum as described above. The results are shown in FIG. 7. Proteins from HCAEC conditioned medium were included for size references. LLGN migrates at approximately 40 kD, corresponding to the lowest band in HCAEC. The medium from COS cells transfected with LLGXL cDNA contains both 68 kD and 40 kD species. When these cells were treated with heparin, the amount of both 68 kD and 40 kD proteins recovered from the medium increased dramatically, indicating either the release of proteoglycan-bound protein from the cell surface or stabilization of the proteins by heparin. When the cells were treated with the protease inhibitor Pefabloc, the amount of 68 kD protein increased relative to that of the 40 kD species. This suggests that the lower molecular weight protein produced by these cells is a proteolysis product of the larger 68 kD form. The role of the mRNA identified through differential display which encodes a shorter, 40 kD species is not known. There has, however, been a report of an alternately-spliced form of hepatic lipase which apparently is expressed in a tissue-specific manner and would create a truncated protein.

Example 6

LIPG in Animal Species

Cloning the Rabbit Homolog of LIPG

Figure 9:
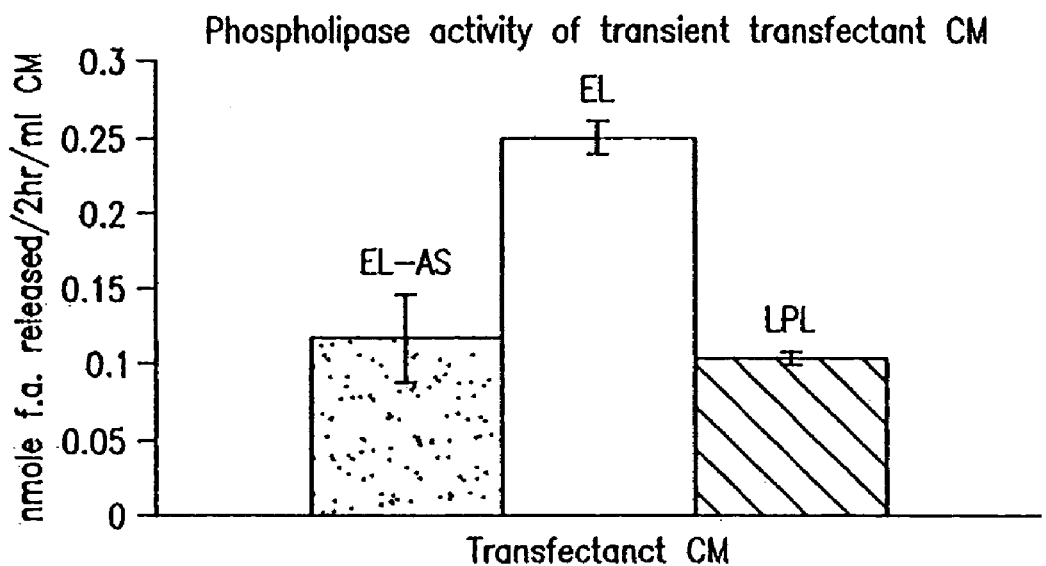

A commercially available lambda cDNA library derived from rabbit lung tissue (Clontech, Cat. #TL 1010b) was used to isolate a fragment of the rabbit homolog of the LIPG gene. Five microliters of the stock library were added to 45 μl water and heated to 95° C. for 10 minutes. The following were added in a final volume of 100 μl: 200 μM dNTPs, 20 mM Tris-HCl pH 8.4, 50 mM KCl, 1.5 mM MgCl$_2$, 100 μM each primer DLIP774 and LLGgen2a, and 2.5 U Taq polymerase (GIBCO). The reaction was thermocycled 35 times with the parameters of: 15 seconds at 94° C., 20 seconds at 50° C. and 30 seconds at 72° C. Ten microliters of the reaction was analyzed via agarose gel electrophoresis. A product of approximately 300 basepairs was detected. A portion (4 μl) of the reaction mix was used to clone the product via the TA cloning system. The insert of a resulting clone was sequenced (SEQ ID NO: 7). An alignment between the deduced rabbit amino acid sequence (SEQ ID NO: 8) and the corresponding sequence of the human cDNA is also shown in FIG. 9. Of the nucleotides not part of either amplification primer, there is an 85.8% identity between the rabbit and human LLG sequences. The predicted protein encoded by this rabbit cDNA shares 94.6% identity with that of the human protein, with most of the nucleotide substitutions in the third or "wobble" positions of the codons. Notably, this region spans the "lid" sequence of the predicted LLG proteins and is a variable domain in the lipase gene family. This is evidence that there is a high degree of conservation of this gene between species.

LIPG in Other Species

To demonstrate the presence of LLG genes in other species, genomic DNAs from various species were restriction digested with EcoRI, separated by electrophoresis in agarose gels, and blotted onto nitrocellulose membranes.

The membranes were hybridized overnight at 65° C. with $2.5 \times 10^6$ cpm/ml of random primed $^{32}$P-LLG or $^{32}$P-LPL (lipoprotein lipase) probe in a hybridization solution of 6×SSC, 10% dextran sulfate, 5× Dendardt's solution, 1% SDS, and 5 g/ml salmon sperm DNA. The membranes were washed with 0.1×SSC, 0.5% SDS for ten minutes at room temperature, then sequentially for ten minutes at 40° C., 50° C., and 55° C. Autoradiograms of the blots are shown in FIG. 11.

Figure 11:
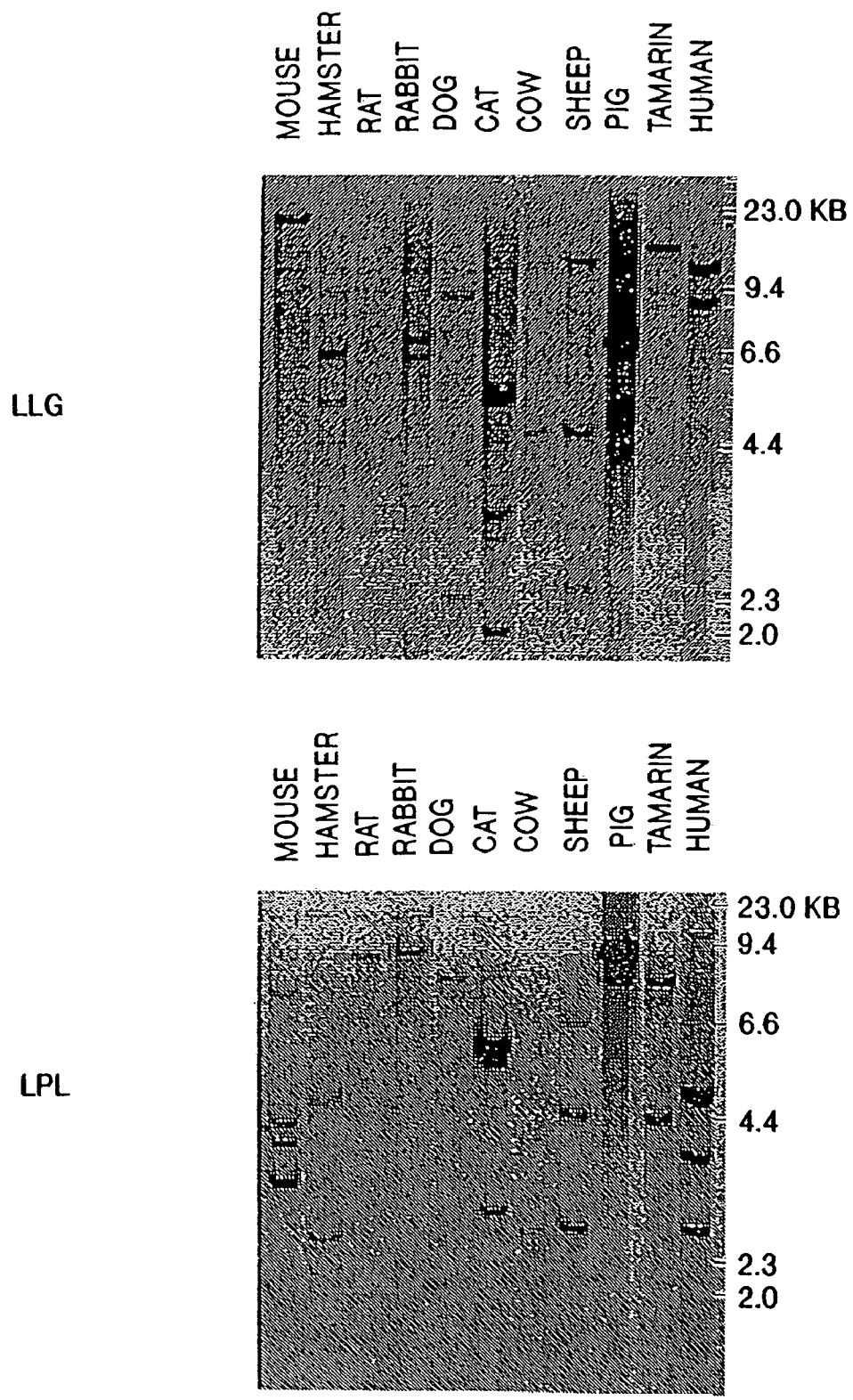
FIG. 11 shows the hybridization of LIPG and LPL probes to genomic DNAs from different species.

FIG. 11 shows the presence of LLG and LPL genes in all species examined, with the exception that no hybridization was observed with the LLG probe against rat DNA. The exceptional data from rat may represent an artifact caused by generation of abnormally sized restriction fragments containing LLG sequences. Such fragments may be outside of the fractionation range of the agarose gel or may blot inefficiently. The different bands detected by the two probes indicate that LPL and LIPG are separate, evolutionarily conserved genes.

Example 7

Enzymatic Activity of LLGXL

Phospholipase Activity

Conditioned media from COS-7 cells transiently expressing human lipoprotein lipase (LPL), LLGN, or LLGXL were assayed for phospholipase activity. MEM containing 10% FBS (MEM) was used as the blank, and conditioned media from COS-7 cells transfected with an antisense LLGXL plasmid (AS) was used as a negative control.

A phosphatidylcholine (PC) emulsion was made up using 10 μl phosphatidylcholine (10 mM), 40 μl $^{14}$C-phosphatidylcholine, dipalmitoyl (2 μCi), labeled at the sn 1 and 2 positions, and 100 μl Tris-TCNB [100 mM Tris, 1% Triton, 5 mM CaCl$_2$, 200 mM NaCl, 0.1% BSA). The emulsion was evaporated for 10 minutes, then brought to a final volume of 1 ml in Tris-TCNB.

Reactions were performed in duplicate and contained 50 μl PC emulsion and 950 μl medium. Samples were incubated in a shaking water bath for 2–4 hours at 37° C. The reactions were terminated by adding 1 ml 1N HCl, then extracted with 4 ml of 2-propanol:hexane (1:1). The upper 1.8 ml hexane layer was passed through a silica gel column, and the liberated $^{14}$C-free fatty acids contained in the flow-thru fraction were quantitated in a scintillation counter. The results of these assays are shown in FIG. 9.

Triacylglycerol Lipase Activity

Conditioned media from COS-7 cells transiently expressing human lipoprotein lipase (LPL), LLGN, or LLGXL were assayed for triglycerol lipase activity. MEM containing 10% FBS was used as the blank, and conditioned media from COS-7 cells transfected with an antisense LLGXL plasmid (AS) was used as a negative control.

A concentrated substrate was prepared as an anhydrous emulsion of labeled triolein, [9,10-$^3$H(N)] and unlabeled triolein (final total triolein=150 mg with 6.25×10⁸ cpm), which was stabilized by adding 9 mg of lecithin in 100% glycerol. 0.56 ml of $^3$H-triolein, (0.28 mCi) was mixed with 0.17 ml of unlabeled triolein and 90 µl of lecithin (9 mg). The mixture was evaporated under a stream of nitrogen. The dried lipid mixture was emulsified in 2.5 ml 100% glycerol by sonication (30 second pulse level 2 followed by 2 second chill cycles over 5 minutes].

The assay substrate was prepared by dilution of 1 volume of concentrated substrate with 4 volumes of 0.2M Tris-HCl buffer (pH 8.0) containing 3% w/v fatty acid free bovine serum albumin. The diluted substrate was vortexed vigorously for 5 seconds.

Figure 10:
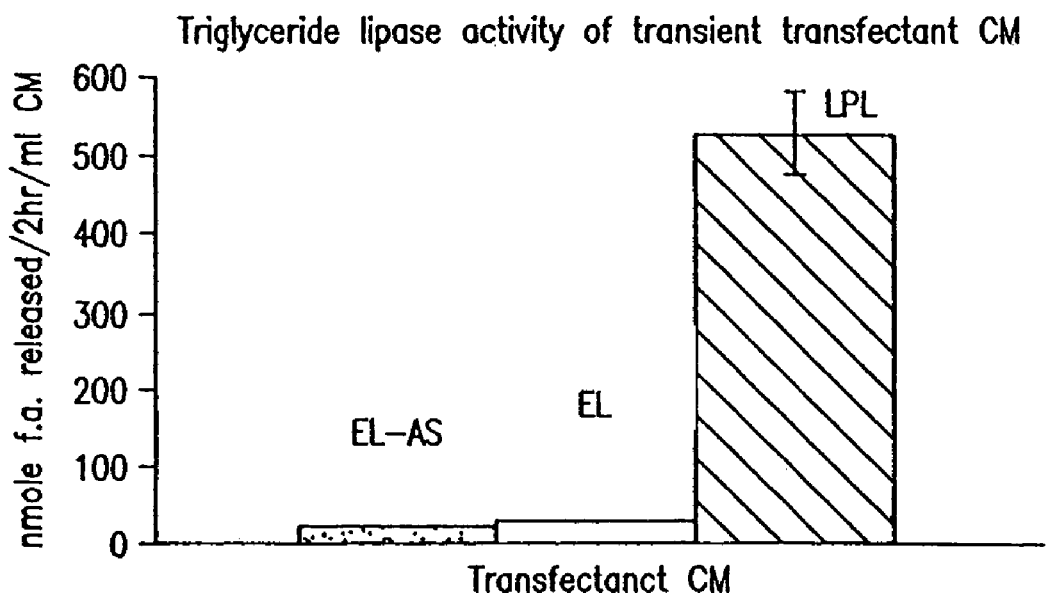

Reactions were performed in duplicate in a total volume of 0.2 ml containing 0.1 ml of assay substrate and 0.1 ml of the indicated conditioned media. The reactions were incubated for 90 minutes at 37° C. The reactions were terminated by adding 3.25 ml of methanol-chloroform-heptane 1.41: 1.25:1 (v/v/v) followed by 1.05 ml of 0.1M potassium carbonate-borate buffer (pH 10.5). After vigorous mixing for 15 seconds, the samples were centrifuged for 5 minutes at 1000 rpm. A 1.0 ml aliquot of the upper aqueous phase was counted in a scintillation counter. The results of these assays are shown in FIG. 10.

Example 8

Use of LIPG Polypeptide to Screen for Enhancers or Inhibitors

Recombinant LIPG is produced in baculovirus-infected insect cells or stably transfected CHO cells or other acceptable mammalian host cells. Recombinant LIPG is purified from the serum-containing or serum-free conditioned medium by chromatography on heparin-Sepharose, followed by chromatography on a cation exchange resin. A third chromatographic or further chromatographic steps, such as molecular sieving, is used in the purification of LIPG if needed. During purification, anti-peptide antibodies are used to monitor LIPG protein and the phospholipase assay is used to follow LIPG activity.

In the fluorescent assay, the final assay conditions are approximately 10 mM Tris-HCl (pH 7.4), 100 mM KCl, 2 mM CaCl$_2$, 5 µM C$_6$NBD-PC{1-acyl-2-[6-(nitro-2,1,3-benzoxadiazol-4-yl)amino] caproylphosphatidylcholine, and LIPG protein (approx. 1–100 ng). The reaction is subjected to fluorescence excitation at 470 nm, and enzyme activity, as measured by the fluorescence emission at 540 nm is continuously monitored. Compounds and/or substances to be tested for stimulation and/or inhibition of LIPG activity are added as 10–200 mM solutions in dimethylsulfoxide. Compounds which stimulate or inhibit LIPG activity are identified as causing an increased or decreased fluorescence emission at 540 nm.

In the thio assay, the final assay conditions are approximately 25 mM Tris-HCl (pH 8.5), 100 mM KCl, 10 mM CaCl$_2$, 4.24 mM Triton X-100, 0.5 mM 1,2-bis(hexanoylthio)-1,2-dideoxy-sn-glycero-3-phosphorylcholine, 5 mM 4,4'-dithiobispyridine (from a 50 mM stock solution in ethanol), and 1–100 ng recombinant LIPG. Phospholipase activity is determined by measuring the increase in absorption at 342 nm. Compounds and/or substances to be tested for stimulation and/or inhibition of LIPG activity are added as 10–200 mM solutions in dimethylsulfoxide. Compounds which stimulate or inhibit LIPG activity are identified as causing an increased or decreased absorption at 342 nm.

Example 9

Transgenic Mice Expressing Human LIPG

To further study the physiological role of LIPG, transgenic mice expressing human LIPG are generated.

The 1.53 kb DraI/SrfI restriction fragment encoding LLGXL was cloned into a plasmid vector (pHMG) downstream of the promoter for the ubiquitously expressed 3-hydroxy-3-methylglutaryl coenzyme A (HMG CoA) reductase gene. Transgenic mice expressing different levels of human LLGXL are generated using standard methods (see, e.g., G. L. Tromp et al. Gene 1565:199–205, 1995). The transgenic mice are used to determine the impact of LLGXL overexpression on lipid profile, vascular pathology, rate of development and severity of atherosclerosis, and other physiological parameters.

Example 10

Expression of LIPG in Atherosclerotic Tissues

LLGXL expression in atherosclerosis was examined by performing a reverse transcription-polymerase chain reaction (RT-PCR) using mRNA isolated from vascular biopsies from four patients with atherosclerosis. The tissue samples were from the aortic wall (one sample), the iliac artery (two samples), and the carotid artery (one sample).

Atherosclerosis biopsies were received from Gloucestershire Royal Hospital, England, and polyA+ mRNA was prepared and resuspended in diethylpyrocarbonate (DEPC) treated water at a concentration of 0.5 µg/µl mRNA. Reverse transcriptase reactions were performed according to the GibcoBRL protocol for Superscript Preamplification System for First Strand cDNA Synthesis. Briefly, the cDNA was synthesized as follows: 2 µl of each mRNA was added to 1 µl oligo (dT)$_{12-18}$ primer and 9 µl of DEPC water. The tubes were incubated at 70° C. for 10 minutes and put on ice for 1 minute. To each tube, the following components were added: 2 µl 10×PCR buffer, 2 µl 25 mM MgCl$_2$, 1 µl 10 mM dNTP mix and 2 µl 0.1M DTT. After 5 minutes at 42° C., 1 µl (200 units) of Super Script II reverse transcriptase was added. The reactions were mixed gently, then incubated at 42° C. for 50 minutes. The reactions were terminated by incubation at 70° C. for 15 minutes then put on ice. The remaining mRNA was destroyed by the addition of 1 µl of RNase H to each tube and incubated for 20 minutes at 37° C.

PCR amplifications were performed using 2 µl of the cDNA reactions. To each tube the following were added: 5 µl lox PCR buffer, 5 µl 2 mM dNTPs, 1 µl hllg-gsp1 primer (20 pmol/ml, see FIG. 1), 1 µl hllg-gsp2a primer (20 pmol/ml, see FIG. 1), 1.5 µl 50 mM MgCl$_2$, 0.5 µl Taq polymerase (5 U/ml) and 34 µl water. After holding the reactions at 95° C. for 2 minutes, thirty cycles of PCR were performed as follows: 15 seconds at 94° C., 20 seconds at 52° C., and 30 seconds at 72° C. The finished reactions were held for 10 minutes at 72° C. before analysis by agarose gel electrophoresis. The hllg-gsp primers are specific for LIPG and yield an expected product of 300 bp. In a parallel PCR to show that the cDNA synthesis reactions had been successful, primers specific for the housekeeping gene, G3PDH (human glyceraldehyde 3-phosphate dehydrogenase) were used (1 µl each at 20 pmol/ml).

The G3PDH primers (SEQ ID NOS. 26 and 27) yielded the expected product of 983 bp in all four vascular biopsy samples. LIPG expression was detected in three of the four samples, with no expression being detected in the carotid artery sample.

Example 11

Differential Display, RT-PCR and cDNA Library Screening

To perform the experiments discussed in Examples 12 to 16, the following procedure (based on the procedure outlined in Example 1) was used to obtain the cDNA for LIPG. THP-1 cells were plated in the presence of phorbol 12-myristate 13-acetate (PMA, 40 ng/ml; Sigma) for 48 hours. The differentiated THP-1 cells were exposed for 24 hours to either oxLDL (50 µg/ml) or control medium. Total RNAs were collected and purified using standard procedures. Poly(A)$^+$ RNA was purified from total RNA using a poly-dT magnetic bead system (Promega). cDNA synthesis and PCR amplification were accomplished using protocols from the Differential Display kit, version 1.0 (Display Systems Biotechnology). The primer pairs that yielded the initial cDNA fragment of EL were downstream primer 7 (5'-TTTTTTTTTTGA-3') (SEQ ID NO: 13) and upstream primer 15 (5'-GATCCAATCGC-3') (SEQ ID NO: 14). The amplification reaction was fractionated on a 6% nondenaturing acrylamide sequencing format gel and an amplification product found only in the reaction containing cDNA from THP-1 cells exposed to oxLDL was identified and excised from the gel. A reamplification using the same primers was performed and the product was excised and subcloned into the pCRII vector using the TA cloning system (Invitrogen). Insert sizes were determined using EcoRI digestions of the plasmids, and clones containing inserts of the approximate size of the original PCR product were sequenced using fluorescent dye-terminator reagents (Prism, Applied Biosystems) and an Applied Biosystems 373 DNA sequencer. We extended the cDNA sequence of the original, gel-excised cDNA using the 5'-RACE system (GIBCO). RNA (1 µg) from the THP-1 cells used initially in the differential display reactions was used in the 5'-RACE procedure using a gene-specific primer (5'-TAGGACATG-CACAGTGTAATCTG-3') (SEQ ID NO: 19) for first strand cDNA synthesis. We performed PCR amplification of the cDNA using an anchor primer and gene-specific primer 2 (5'-GATTGTGCTGGCCACTTCTC-3') (SEQ ID NO: 16). This reaction (1 µl) was used in a nested re-amplification using the universal amplification primer (5'-CUACUAC-UACUAGGCCACGCGTCGACTAGTAC-3') (SEQ ID NO: 18) and the gene-specific primer 3 (5'-GACACTC-CAGGGACTGAAG-3') (SEQ ID NO: 17) to increase levels of specific product for subsequent isolation. The reaction products were cloned into the pCRII vector from the TA cloning kit and the sequence determined. A human placental cDNA library (oligo dT and random primed) was obtained from Clontech and probed with the 5'-RACE reaction PCR product. The DNA from hybridizing clones was purified using LambdaSorb reagent (Promega). Inserts were excised from the phage DNA by digestion with EcoRI, subcloned into the EcoRI site of the Bluescript II SK plasmid vector (Stratagene), and sequenced.

Example 12

Antibody Preparation

A 17-residue peptide (GPEGRLEDKLHKPKATC) (SEQ ID NO: 12) was synthesized corresponding to residues 8–23 of the secreted LIPG gene product on a Model 433A peptide synthesizer (Applied Biosystems). Peptide (2 mg) was coupled to maleimide-activated keyhole limpet haemocyanin (2 mg) following the protocols included in the Imject Activated Immunogen Conjugation kit (Pierce Chemical). After desalting, one-half of the conjugate was emulsified with an equal volume of Freund's complete adjuvant (Pierce) and injected into a New Zealand White rabbit. Four weeks after the initial inoculation, a booster inoculation was administered with an emulsification made exactly as described above except for the use of Freund's incomplete adjuvant (Pierce). Two weeks after the boost, the titres of specific antibodies were determined in a test bleed via ELISA using immobilized peptide.

Example 13

Gene Expression Studies

HUVECs were propagated in a commercially prepared endothelial cell growth medium (EGM, Clonetics) supplemented with bovine brain extract (3 mg/ml; Clonetics), whereas HCAECs were propagated in EGM with bovine grain extract (3 mg/ml) and 5% fetal bovine serum. Cultures were stimulated by addition of PMA (100 ng/ml). After 24 hours incubation, RNA was extracted from the cells via the Trizol method, electrophoresed on a 1% agarose-formaldehyde gel, transferred to Nytran membrane on a Turboblotter apparatus (Schleicher and Schuell) and crosslinked to the membrane using a Stratalinker ultraviolet crosslinker (Stratagene). The 5'-RACE reaction PCR product was radiolabelled using the random priming technique. The radiolabelled probe (1–2×10$^6$ cpm/ml) was denatured by heating to 95° C. for 10 minutes and quick-chilled on ice before adding to the filter in QuikHyb. Hybridization was allowed to proceed for 3 hours at 65° C. Filters were exposed to Kodak XAR-2 film with intensifying screens at −80° C. We incubated HUVEC- and HCEAC-conditioned medium with heparin-Sepharose CL-6B at 4° C. for 1 hour. After centrifugation, the pelleted heparin-Sepharose was suspended in SDS loading buffer, heated to 95° C. for 5 minutes and loaded onto a 10% Tris-Glycine SDS gel (NOVEX). After electrophoresis at 140 V for 90 minutes, the proteins were transferred to nitrocellulose membranes and detected with rabbit anti-LIPG peptide antisera (1:5,000), with goat anti-rabbit peroxidase conjugated antisera (1:5,000; Boehringer) as the secondary antibody. The membranes were reacted with Renaissance chemiluminescent reagent (DuPont NEN) and exposed to Kodak XAR-2 film. A commercially prepared filter containing poly(A)$^+$ RNAs (3 µg each) from human heart, brain, placenta, lung, liver, skeletal muscle, kidney and pancreas (Clontech) was hybridized with a radiolabelled fragment and processed as described above. Following autoradiography, the blot was stripped by washing in boiling 0.1×SSC, 0.1% SDS for 2×15 minutes at 65° C. and then probed as described above with a 1.4-kb cDNA fragment encoding human LPL. This fragment was obtained by RT-PCR of the THP-1 RNA (PMA and oxLDL treated) using the 5' LPL and 3' LPL primers 5'-ACCACCATGGAGAG-CAAAGCCCTG-3' (SEQ ID NO: 20) and 5'-CCAGTTTCAGCCTGACTTCTTATTC-3' (SEQ ID NO: 21), respectively. After exposure to film, the membranes were stripped again and reprobed with a radiolabelled fragment of human β actin cDNA to normalize to RNA content.

Human umbilical vein endothelial cells (HUVEC) were negative for LPL mRNA expression as expected, but were found to constitutively express a high level of mRNA for the LIPG gene (FIG. 4).

Human coronary artery endothelial cells (HCAEC) were also found to express the mRNA which was further upregulated on treatment of these cells with phorbol ester (FIG. 4).

Conditional medium from stimulated HUVEC and HCAEC contained immunoreactive proteins of approximately 68 kD and 40 kD, as well as a less prominent band of 55 kD (FIG. 6).

Figure 3:
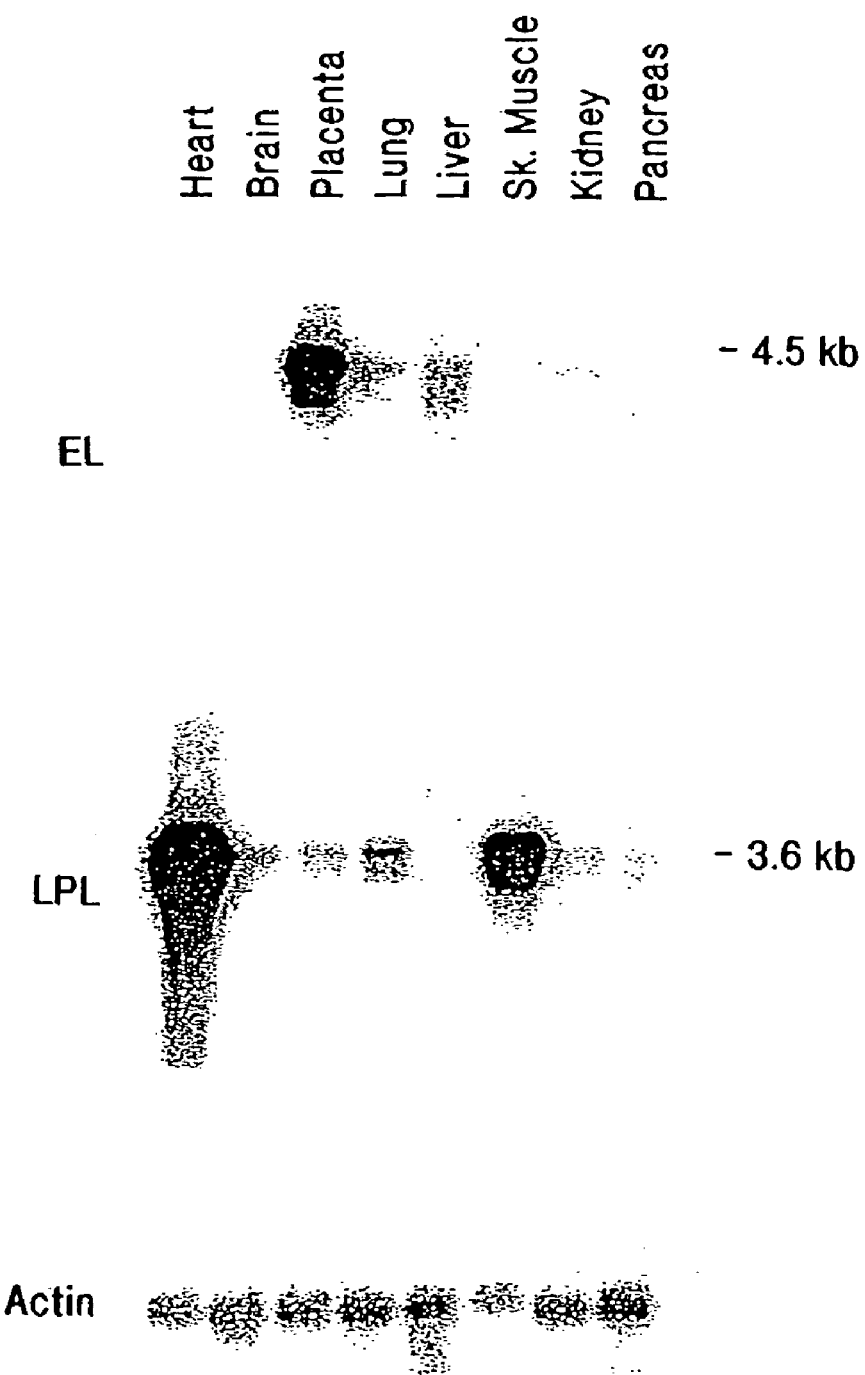

To determine the tissue sites of LIPG production in vivo, a multiple human tissue northern blot analysis with probes for both LIPG and LPL was performed. Abundant levels of LIPG mRNA were found in lung, liver and kidney (FIG. 3) tissues, which showed low levels of LPL expression. LIPG was also expressed at high levels in the placenta (FIG. 3), suggesting the potential for a role in development.

In tissues such as heart and skeletal muscle, which expressed the highest amount of LPL (confirming previous reports, Goldberg, J. I., *J. Lipid Res.*, 37, 693–707 (1996)), we did not detect LIPG expression. This analysis indicated that the tissue distribution of LIPG expression is very different from that of LPL, as well as that reported for HL and PL. We found no LIPG mRNA in adrenals or ovaries, but did find a very low level of LIPG mRNA in the testes (data not shown). We also found that HepG2 cells express LIPG mRNA and protein in vitro (data not shown), but at levels less than 10% of that expressed by HUVECs.

Example 14

Lipase Assays

The cDNA and the 1.4-kb LPL cDNA were cloned into the EcoRV site of the mammalian expression vector pCDNA3 (Invitrogen). An antisense pCDNA3 vector was used as negative control. The recombinant expression vectors (3 µg) were mixed with lipofectamine (Life Technologies) and transfected in quadruplicate into semiconfluent COS7 cells in 60-mm dishes. Established methods were used to assay samples of conditioned media from transfected COS7 cells for TG lipase and phospholipase activities (Goldberg, J. I., *J. Lipid Res.*, 37, 693–707 (1996)). for the TG lipase assay, 9,10-$^3$H(N)-triolein (250 µCi; NEN) was mixed with unlabeled triolein (150 mg) and type IV-S-α lecithin (9 mg; Sigma) in glycerol. The mixture was evaporated under nitrogen and emulsified in glycerol (2.5 ml) by sonication with a Branson Sonifier 450. The assay substrate was prepared by combining one volume of the emulsified substrate, four volumes of Tris-HCl (0.2 M, pH 8.0) containing 3% (w/v) fatty acid-free bovine serum albumin (BSA) and one volume of heat-inactivated bovine serum. Reactions were performed in triplicate in a total volume (0.2 ml) containing assay substrate (0.1 ml) and conditioned media (0.1 ml). The reactions were incubated for 2 hours at 37° C. and terminated by adding methanol-chloroform-heptane (1.41:1.25:1; 3.25 ml) followed by potassium carbonate-borate buffer (1.05 ml; 0.1 M, pH 10.5). After vigorous mixing for 15 seconds, the samples were centrifuged for 5 minutes at 1,000 rpm and the upper aqueous phase (1.0 ml) was counted in a scintillation counter. For the phospholipase assay, a phosphatidylcholine (PC) emulsion was made by combining $^{14}$C-dipalmitoyl PC (2 µCi; NEN) and lecithin (10 µl) with Tris-TCNB (100 µl; 100 mM Tris-HCl pH 7.4, 1% Triton X-100, 5 mM CaCl$_2$, 200 mM NaCl, 0.1% BSA). The mixture was vortexed for 2 minutes and then evaporated under nitrogen. The dried lipid was reconstituted with TCNB (1 ml) and vortexed for 10 seconds. Reactions were performed in triplicate and contained PC emulsion (50 µl), conditioned media (600 µl) and MEM (350 µl). Samples were incubated at 37° C. for 2 hours, terminated by addition of HCl (1 ml) and extracted with 2-propanol:hexane (1:1; 4 ml). A sample (1.8 ml) of the upper hexane layer was passed through a silica gel column, and the liberated $^{14}$C-free fatty acids contained in the flow-through fraction were quantitated in a scintillation counter. For both assays, MEM containing 10% FBS was used as a blank and conditioned media from COS7 cells transfected with an antisense plasmid (AS) was used as a negative control.

Example 15

Recombinant Adenovirus Construction and Animal Studies

A recombinant adenovirus encoding human LIPG was constructed as described (Tsukamoto et al., *J. Clin. Invest.*, 100, 107–114 (1997); Tsukamoto et al., *J. Lipid Res.*, 38, 1869–1876 (1997)). In brief, the full-length human cDNA was subcloned into the shuttle plasmid vector pAdCMV-Link1. After screening for the appropriate orientation by restriction analysis, the plasmid was linearized with NheI and cotransfected into 293 cells along with adenoviral DNA digested with ClaI. Cells were overlaid with agar and incubated at 37° C. for 15 days. Six plaques were picked and screened by PCR; two plaques positive for cDNA were subjected to a second round of plaque purification. After confirmation of the presence of cDNA, the recombinant adenovirus was expanded in 293 cells at 37° C. Cell lysates were used to infect HeLa cells for confirmation of the expression of human LIPG by western blot of conditioned media. The recombinant adenovirus (AdhEL) was further expanded in 293 cells and purified by cesium chloride ultracentrifugation. Control adenovirus containing no cDNA insert (Adnull) was also subjected to plaque purification and purified as described above. The purified viruses were stored in 10% glycerol/PBX at –80° C. Wild-type C57BL/6, human apoA-I transgenic and LDL receptor mutant mice were obtained from Jackson Laboratory. All mice were fed chow diets. Wild-type and human apoA-I transgenic mice were injected intravenously via the tail vein with AdhEL or Adnull 1×10$^{11}$ particles (approximately 2×10$^9$ pfu) and LDLR-deficient mice were injected with 1×10$^{10}$ particles. In all experiments, blood was obtained from the retro-orbital plexus 1 day before injection and at multiple time points following injection.

Figure 12:
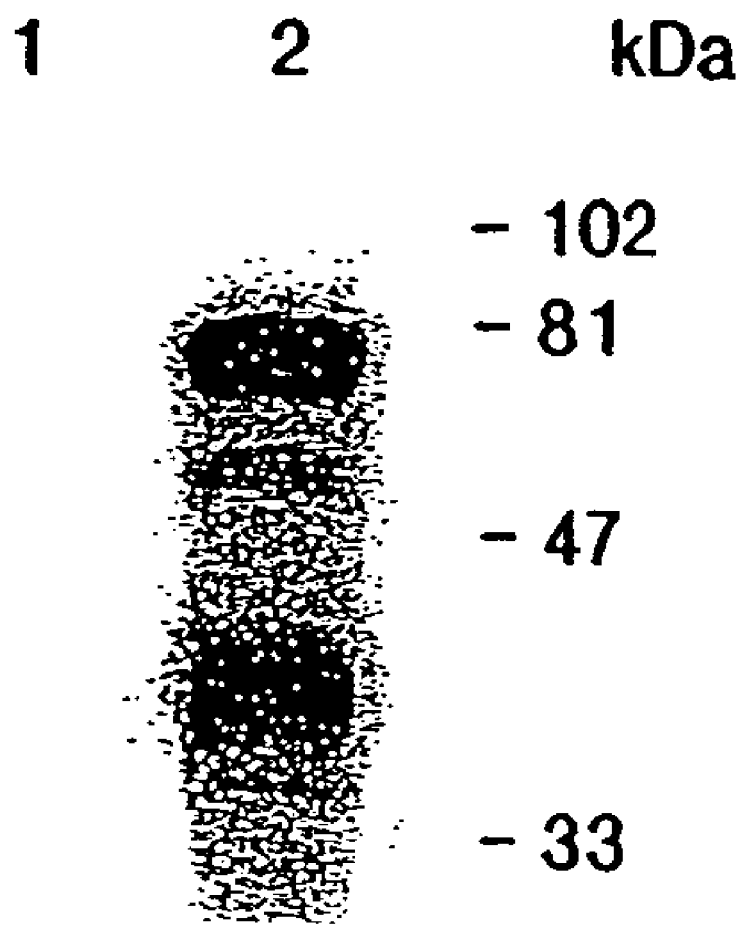
FIG. 12 shows expression of LIPG in the liver of a wild-type mouse 5 days after AdhEL injection. Lane 1, liver from mouse injected with Adnull; lane 2, liver from mouse injected with AdhEL.
Figure 13:
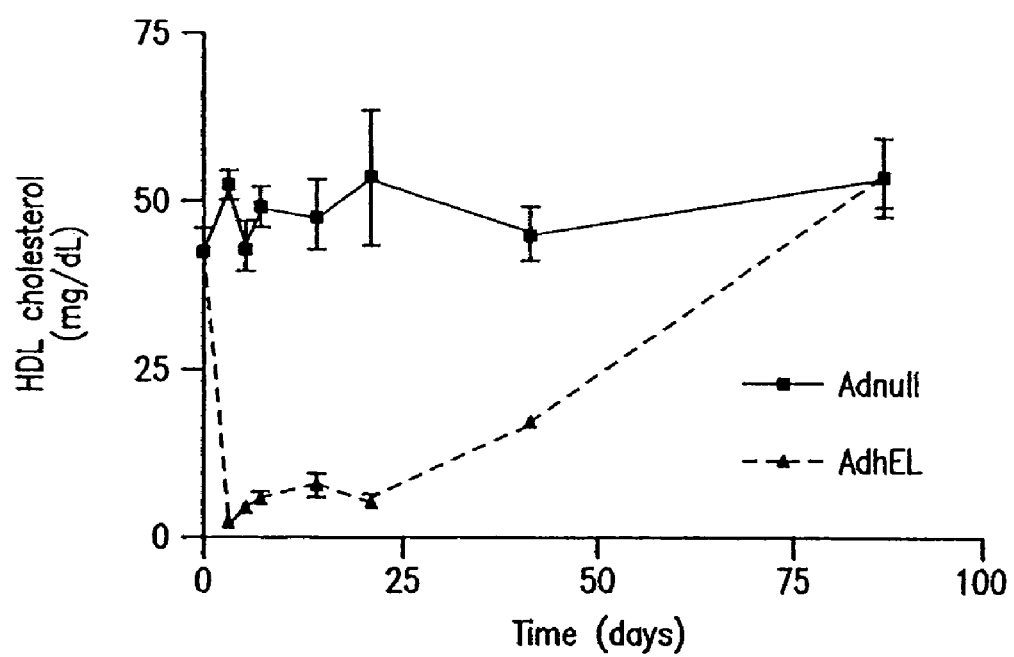
FIG. 13 shows plasma levels of HDL cholesterol in AdhEL- and Adnull-injected wild-type mice.
Figure 14:
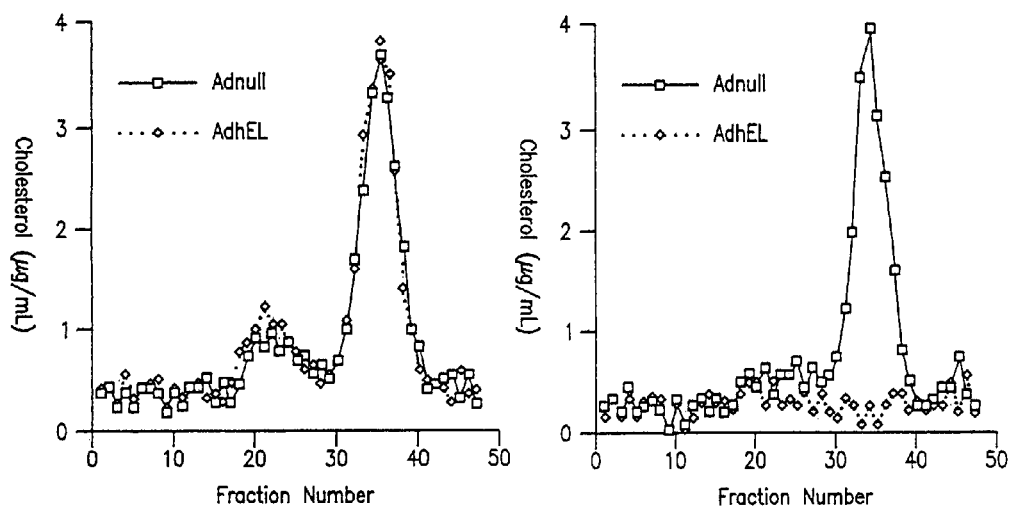
FIG. 14 shows lipoprotein profiles in wild-type mice injected with AdhEL and Adnull at baseline before injection (left) and 14 days after injection (right).
Figure 15:
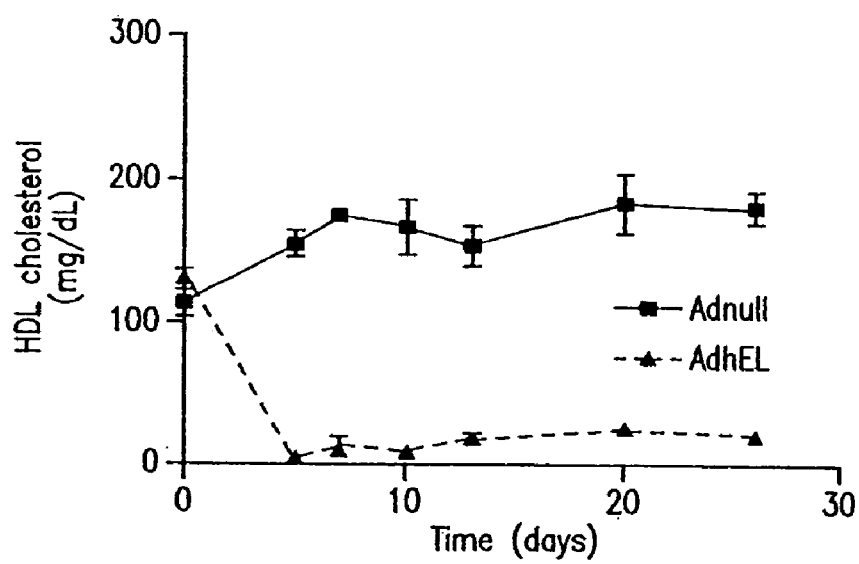
FIG. 15 shows HDL cholesterol levels in human apoA-I transgenic mice after injection with Adnull or AdhEL.
Figure 16:
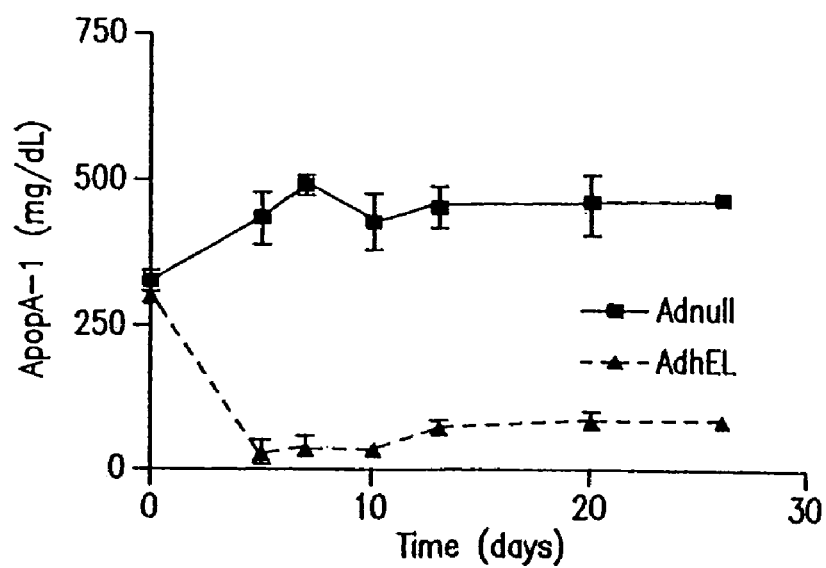
FIG. 16 shows ApoA-I levels in human apoA-1 transgenic mice after injection with Adnull or AdhEL.
Figure 17:
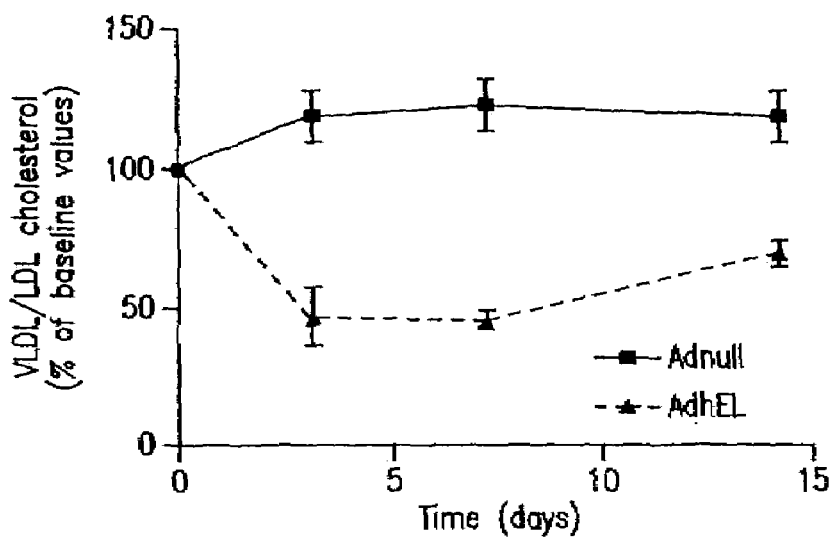
FIG. 17 shows the effect of injection of AdhEL in LDL receptor-deficient mice on VLDL/LDL cholesterol levels.
Figure 18:
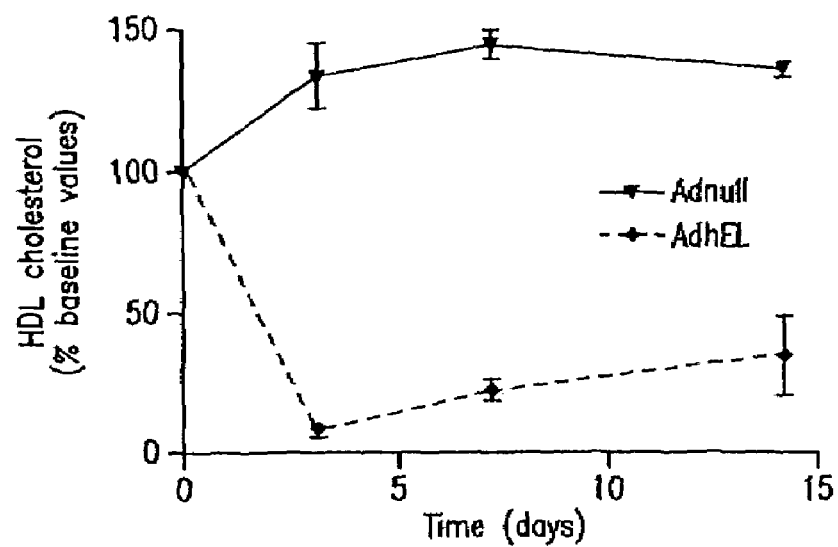
FIG. 18 shows the effect of AdhEL on HDL receptor-deficient mice on HDL cholesterol levels.

Intravenous injection of AdhEL into wild-type C57BL/6 mice resulted in expression in the liver (FIG. 12) and reduction of plasma levels of HDL cholesterol that remained significantly lower than control virus-injected mice through at least 41 days post-injection (FIG. 13). Lipoproteins were separated by FPLC gel filtration, demonstrating that HDL was undetectable 14 days after adenovirus injection (FIG. 14). Injection of recombinant LIPG adenovirus into human apoA-I transgenic mice (which have much higher levels of HDL cholesterol and apoA-I) reduced both HDL cholesterol (FIG. 15) and apoA-I (FIG. 16) levels. To determine the relative effects of LIPG expression on HDL compared with the apoB-containing lipoproteins VLDL and LDL, we injected a lower dose of the LIPG adenovirus into chow-fed LDL receptor-deficient mice, which have approximately 70% of cholesterol in VLDL/LDL and approximately 30% in HDL. As before, expression of LIPG reduced HDL cholesterol levels (FIG. 18). Although LIPG expression reduced VLDL/LDL cholesterol levels in the same mice (FIG. 19), the effect was proportionately less. Overexpression of LIPG reduced VLDL/LDL cholesterol, therefore a role of LIPG in the modulation of apoB-containing lipoproteins cannot be excluded.

Example 16

Lipid/Lipoprotein Analyses

The plasma total cholesterol and HDL cholesterol levels were measured enzymatically on a Cobas Fara (Roche Diagnostic Systems) using Sigma reagents. ApoA-I was quantitated using a turbidometric assay (Sigma) on a Cobas Fara. Pooled plasma samples were subjected to fast protein liquid chromatography (FPLC) gel filtration (Pharmacia LKB Biotechnology) using two Superose 6 columns in series as described (Tsukamoto et al., *J. Clin. Invest.*, supra). Fractions (0.5 ml) were collected, and cholesterol concentrations were determined using an enzymatic assay (Wako Pure Chemical Industries).

Example 17

Identification of Inhibitors of LIPG

Modulators of EL activity may be found using the following method:

Recombinant LIPG would be purified from the conditioned medium of stably transfected Chinese hamster ovary cells, from baculovirus infected insect cells, yeast (*Pichia pastoris, Kluveromyces Lactis*) or other sources. Non-recombinant sources of LIPG (such as human plasma, endothelial cell conditioned media, etc.) could also be employed. An example of a primary screen to look for modulators of LIPG activity would utilize the soluble fluorescent substrate 4-methylumberiferyl hepatanoate. This assay is continuous and homogeneous. Hydrolysis of this substrate by LIPG results in the production of highly fluorescent 4-methylumbelliferone that can be measured in a microplate fluorimeter. Other primary screening assay formats that could be used are a scintillation proximity assay (Amersham) that measures phospholipase activity, the lower-throughput radiometric phospholipase assay described in Example 7 (and proposed below as a secondary assay), or the alternative phospholipase assays described in Example 8.

The catalytic center of LIPG, like other TG lipases, consists of the same catalytic triad (ser, his, asp) found in serine proteases. Indeed, other TG lipases, such as lipoprotein lipase, are inhibited by serine protease inhibitors such as PMSF and DFP. Either one of these compounds may serve as a positive control for inhibitors of LIPG activity.

Secondary assay: Compounds active in the esterase assay or alternative screening assays described above will be assayed in a standard, radiometric phospholipase A assay. This assay measures the release of radiolabelled palmitic acid from mixed micelles containing [14C]-dipalmitoyl-phosphatidylcholine. Other assay formats could be envisioned which utilize fluorescent substrates and which would be amenable to a greater throughput.

Selectivity assays: Compounds would be assayed for inhibition of the related enzymes lipoprotein lipase (LPL) and pancreatic lipase (PL). Human PL and bovine LPL are commercially available and assays could be readily implemented. The phospholipase activity of PL is measured in exactly the same way as described above for the secondary assay of LIPG. Since LPL is primarily a TG lipase, the secondary assay would measure radiolabelled fatty acid (oleic acid) release from a radiolabelled TG (triolein) substrate (described in Example 7). This assay has a similar capacity and may be adapted to other assay formats which utilize fluorescent substrates and which would be amenable to a greater throughput.

Phospholipase activity of LIPG would be tested on its in vivo substrate, HDL, in an in vitro assay. Radiolabelled HDL could be generated by exchange with a radiolabelled phospholipid, and then used to measure LIPG phosphospholipase activity and the activity of compounds emerging from the screens.

An additional assay could measure the impact of preincubation of LIPG, HDL, +/-compounds on radiolabelled cholesterol efflux from cultured cells such as the rat Fu5AH hepatoma line.

In vivo assays for assessment of compounds can be run in wild-type, LIPG-overexpressing, and as control, LIPG null mice. If, as in the case of adenoEL expression, the transgenic mice exhibit decreased HDL relative to control mice, then treatment of transgenic mice with LIPG inhibitory compounds would be expected to raise HDL to the levels of control mice. It is also possible that compounds could be tested for their LIPG inhibitory activity (elevation of HDL) in other animals such as the LDLR-/- mouse, apoA1 transgenic mice hamsters, or rabbits. Compounds which elevated LIPG or LIPG activity would be expected to raise HDL in these or other animal models.

Example 18

Inhibitory Small Molecule Treatment Method

A small molecule (hereafter an "inhibitory small molecule") identified in the screening outlined in Example 17 as able to inhibit the LIPG polypeptide in vitro is tested for its ability to inhibit the LIPG polypeptide in vivo. Wild-type and LIPG transgenic mice will be studied by administering the small molecule orally (if orally bioavailable) or by intravenous injection. Activity of the LIPG polypeptide will be measured in plasma before and after heparin injection (to release the enzyme from bound sites). In addition, cholesterol, VLDL, LDL and HDL cholesterol and apoA-I levels will be monitored in animals receiving the inhibitory small molecule. Finally, LDL receptor deficient mice will be fed an atherogenic diet and administered the inhibitory small molecule or placebo for a period of 8 weeks. Atherosclerosis will be quantitated in the aortas of the mice in order to determine whether administration of the inhibitory small molecule recudes the progression or induces regression of atherosclerosis. Based on these preclinical data, additional animal models such as hamsters, rabbits, or pigs will be studied for the ability of the inhibitory small molecule to raise HDL cholesterol levels, reduce VLDL and LDL cholesterol levels, and/or inhibit the progression of atherosclerosis.

Those inhibitory small molecules found to have the desired properties will be administered to patients in combination with pharmaceutically acceptable carriers. The inhibitory small molecules may be administered in a variety of ways, including oral administration and intravenous injection. The patients' HDL, VLDL and LDL cholesterol levels will be monitored to determine efficacy of the inhibitory small molecule and to optimize dosage and administration protocols.

Example 19

Inhibitory Peptide Treatment Method

Therapeutic peptides are identified by testing fragments of the LIPG polypeptide to determine which of these fragments inhibit LIPG polypeptide activity in vitro. Once identified, an "inhibitory peptide" is then tested for its ability to inhibit the LIPG polypeptide in vivo. Inhibitory peptides will be produced recombinantly in E. coli and purified by methods known in the art. The effect of the inhibitory peptides will be studied in wild-type and LIPG transgenic mice by administering the inhibitory peptide by intravenous injection. Activity of the LIPG polypeptide will be measured in plasma before and after heparin injection (to release the enzyme from bound sites). In addition, cholesterol, VLDL, LDL and HDL cholesterol and apoA-I levels will be monitored in animals receiving the inhibitory peptide. Finally, LDL receptor deficient mice will be fed an atherogenic diet and administered the inhibitory peptide or placebo for a period of 8 weeks. Atherosclerosis will be quantitated in the aortas of the mice in order to determine whether administration of the inhibitory peptide reduces the progression or induces regression of atherosclerosis. Based on these preclinical data, additional animal models such as hamsters, rabbits or pigs will be studied for the ability of the inhibitory small molecule to raise HDL cholesterol levels, reduce VLDL and LDL cholesterol levels, and/or inhibit the progression of atherosclerosis.

Those inhibitory peptides found to have the desired properties will be administered to patients in combination with pharmaceutically acceptable carriers. The inhibitory peptides may be administered in a variety of ways, including oral administration and intravenous injection. The patients' HDL, VLDL and LDL cholesterol levels will be monitored to determine efficacy of the inhibitory peptides and to optimize dosage and administration protocols.

Example 20

Antisense Treatment Method

A series of antisense oligonucleotides, each complementary to about 20 bases of the LIPG cDNA sequence are chemically synthesized by standard techniques. To determine the most efficient oligonucleotide to use therapeutically, each oligonucleotide is individually transfected into cells expressing the LIPG gene, using standard transfection protocols.

At about 24–48 hours following transfection of the oligonucleotides, the LIPG mRNA level in cells is determined by quantitative PCR, northern blot, RNAse protection, or other appropriate methods. Alternatively, LIPG expression may be monitored with specific antibodies, which can be used to screen for effective antisense oligonucleotides. Oligonucleotides which effectively reduce LIPG mRNA levels are then formulated for in vivo delivery as therapeutics.

Antisense LIPG sequences may be delivered in a gene therapy vector, such as adenovirus, adeno-associated virus, retrovirus, naked DNA, or other systems discussed in the detailed description. Such fragments can be used therapeutically when delivered in gene therapy vectors. Hepatic expression of such recombinant vectors is a preferred approach. Alternatively, synthetic antisense oligonucleotides may be formulated for in vivo delivery as therapeutics as described above.

Antisense oligonucleotides may be administered by the following routes: intravenous, subcutaneous, introdermal, pulmonary, oral, intraventricular, intrathecal, and topical. The route of administration may include direct administration to vessel walls (i.e., endothelium and/or vascular smooth muscle). As an example, patients with low HDL-C could receive a dose of 0.5–2 mg/kg of an effective antisense oligonucleotide, infused intravenously, every other day for up to 2–3 weeks. As LIPG is expressed in the liver, it may be desireable to deliver antisense reagents to the portal circulation. This may be accomplished by conjugating or complexing the oligonucleotide with a liver-targeting moiety, such as asialoglycoprotein. Dose and timing of therapy would depend on efficiency of antisense delivery, as well as parameters such as half life, specificity and toxicology of the antisense oligonucleotide.

Increase in HDL-C can be monitored using standard clinical laboratory procedures. The original dosing schedule (such as that described above) is repeated as often as required to maintain HDL-C above 35 mg/dL.

Example 21

Ribozyme Treatment Method

Based on the LIPG cDNA sequence, hammerhead ribozymes which effectively reduce LIPG mRNA levels are prepared. These consist of two "arms" of 6–7 bases each of nucleotide sequence complementary to LIPG mRNA, separated by the catalytic moiety of the ribozyme. Examples of such hammerhead motifs are described by Rossi et al., 1992, *Aids Research and Human Retroviruses*, 8, 183. The ribozymes are expressed in eukaryotic cells from an appropriate DNA vector.

The ribozymes may be administered encapsulated in liposomes, as discussed above.

The ribozyme/liposome composition is delivered to the liver by direct injection or by use of a catheter, infusion pump or stent. The route of administration may include direct administration to vessel walls (i.e., endothelium and/or vascular smooth muscle). Patients are treated for up to 2 weeks with 5–50 mg/kg/day ribozyme in a pharmaceutically effective carrier. Increase in HDL-C and dosing regimen are monitored and determined as for antisense oligonucleotides.

Example 22

Neutralizing Antibody Treatment Method

Anti-LIPG antibodies, antibody fragments, or chimeric antibodies consisting of at least one LIPG-binding moiety, prepared as described in Example 12, are used to inhibit LIPG activity in vivo. The antibodies may be delivered as a bolus only, infused over time, or both. Typically a dose of 0.2–0.6 mg/kg is given as bolus, followed by a 2 to 12-hour infusion. Alternatively, multiple bolus injections are administered every other day, or every third of fourth day, as required to reduce LIPG and raise HDL-C. Repeat dosing is performed as determined by measurement of HDL-C levels. Antibodies to LIPG may also be delivered in a gene therapy vehicle to facilitate expression in vivo. The level of expression of the antibody is determined indirectly by measuring HDL-C levels and additional vectors may be introduced as needed.

Example 23

Use of Inhibitory Molecules or Enhancer Molecules

Fragments of LIPG protein, which can inhibit LIPG activity by competing for binding to intact LIPG, required coactivator molecules, cell surface receptors or binding proteins, may be delivered as therapeutic recombinant proteins or from gene therapy vectors.

As an example, the LLGN polypeptide based on LIPG is cloned into a recombinant adenovirus as described (Tsukamoto et al., *J. Clin. Invest.*, 100, 107–114 (1997); Tsukamoto et al., *J. Lipid Res.*, 38, 1869–1876 (1997)). The LLGN cDNA is cloned into the shuttle plasmid vector pAdCMV-Link1. After screening for the appropriate orientation by restriction analysis, the plasmid is linearized with NheI and cotransfected into 293 cells along with adenoviral DNA digested with ClaI. Cells are then overlaid with agar and incubated at 37° C. for 15 days. Plaques are picked and screened by PCR; plaques positive for cDNA are subjected to a second round of plaque purification. After confirmation of the presence of cDNA, the recombinant adenovirus is expanded in 293 cells at 37° C. Cell lysates are used to infect HeLa cells for confirmation of the expression of human EL by western blot of conditioned media. The recombinant adenovirus is further expanded in 293 cells and purified by cesium chloride ultracentrifugation. The purified viruses are stored in 10% glycerol/PBX at −80° C. The patient is injected intravenously with the recombinant adenovirus $1\times10^{11}$ particles (approximately $2\times10^9$ pfu).

Example 24

Methods of Increasing the Level of LIPG in a Patient by Expression of LIPG from an Expression Vector The full length LIPG cDNA is cloned into a recombinant adenovirus (Tsukamoto et al., *J. Clin. Invest.*, 100, 107–114 (1997); Tsukamoto et al., *J. Lipid Res.*, 38, 1869–1876 (1997)) encoding human LIPG. The full-length human LIPG cDNA is cloned into the shuttle plasmid vector pAdCMV-Link1. After screening for the appropriate orientation by restriction analysis, the plasmid is linearized with NheI and cotransfected into 293 cells along with adenoviral DNA digested with ClaI. Cells are overlaid with agar and incubated at 37° C. for 15 days. Plaques are picked and screened by PCR; plaques positive for cDNA are subjected to a second round of plaque purification. After confirmation of the presence of cDNA, the recombinant adenovirus is expanded in 293 cells at 37° C. Cell lysates are used to infect HeLa cells for confirmation of the expression of human LIPG polypeptide by western blot of conditioned media. The recombinant adenovirus (AdhEL) is further expanded in 293 cells and purified by cesium chloride ultracentrifugation. The purified viruses are stored in 10% glycerol/PBX at −80° C. Patients are injected intravenously with AdhEL or Adnull $1\times10^{11}$ particles (approximately $2\times10^9$ pfu).

Example 25

Methods of Increasing the Level of LIPG Activity by Administration of a Full-Length Wild-Type or Engineered Recombinant LIPG Protein The wild-type LIPG protein reduces VLDL and LDL cholesterol levels and LIPG could be engineered to act specifically on VLDL and LDL cholesterol without having effects on HDL cholesterol. Administration of wild-type or engineered recombinant LIPG could in certain circumstances be used as a therapy for reducing VLDL and/or LDL cholesterol levels. Wild-type and/or engineered LIPG protein ("recombinant LIPG protein") will be produced recombinantly in *E. coli* and purified using methods known in the art. Wild-type mice will be studied by administering the recombinant LIPG protein by intravenous injection. Activity of LIPG will be measured in plasma. In addition, cholesterol, VLDL, LDL and HDL cholesterol and apoA-I levels will be monitored in animals receiving the recombinant LIPG protein. Finally, LDL receptor deficient mice will be fed an atherogenic diet and administered the recombinant LIPG protein or placebo for a period of 8 weeks. Atherosclerosis will be quantitated in the aortas of the mice in order to determine whether adminsitration of the recombinant LIPG protein reduces the progression or induces regression of atherosclerosis. Based on these preclinical data, additional animal models such as hamsters, rabbits, or pigs will be studied for the ability of the recombinant LIPG protein to reduce VLDL and LDL cholesterol levels and/or inhibit the progression of atherosclerosis. Those recombinant LIPG proteins found to have the desired ability to reduce VLDL and LDL cholesterol levels and/or inhibit the progression of atherosclerosis will be combined with a pharmaceutically acceptable carrier and administered to patients. The recombinant LIPG polypeptides may be administered in a variety of ways, including oral administration and intravenous injection.

All the references discussed herein are incorporated by reference.

One skilled in the art will readily appreciate the present invention is well adapted to carry out the objects and obtain the ends and advantages mentioned, as well as those inherent therein. The peptides, polynucleotides, methods, procedures and techniques described herein are presented as representative of the preferred embodiments, and intended to be exemplary and not intended as limitations on the scope of the present invention. Changes therein and other uses will occur to those of skill in the art which are encompassed within the spirit of the invention or defined by the scope of the appended claims.

We claim:

1. A method for measuring the level of human endothelial lipase (LIPG) having an amino acid sequence of SEQ ID NO. 6 in a tissue sample obtained from a human patient by conducting an immunoassay for said LIPG.

2. The method of claim 1 wherein said tissue is blood.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 367 base pairs
      (B) TYPE: nucleic acid
      (C) STRANDEDNESS: double
      (D) TOPOLOGY: linear (ii) MOLECULE TYPE: cDNA (ix) FEATURE:
             (A) NAME/KEY: CDS
             (B) LOCATION: 22..180

(xi) SEQUENCE DESCRIPTION: SEQ ID NO: 1:

```
GAATTCGGCT TGATCAATCG C TTC AAA AAG GGG ATC TGT CTG AGC TGC CGC        51
                        Phe Lys Lys Gly Ile Cys Leu Ser Cys Arg
                         1               5                  10

AAG AAC CGT TGT AAT AGC ATT GGC TAC AAT GCC AAG AAA ATG AGG AAC        99
Lys Asn Arg Cys Asn Ser Ile Gly Tyr Asn Ala Lys Lys Met Arg Asn
            15                  20                  25

AAG AGG AAC AGC AAA ATG TAC CTA AAA ACC CGG GCA GGC ATG CCT TTC       147
Lys Arg Asn Ser Lys Met Tyr Leu Lys Thr Arg Ala Gly Met Pro Phe
        30                  35                  40

AGA GGT AAC CTT CAG TCC CTG GAG TGT CCC TGA GGAAGGCCCT TAATACCTCC     200
Arg Gly Asn Leu Gln Ser Leu Glu Cys Pro
        45                  50

TTCTTAATAC CATGCTGCAG AGCAGGGCAC ATCCTAGCCC AGGAGAAGTG GCCAGCACAA     260

TCCAATCAAA TCGTTGCAAA TCAGATTACA CTGTGCATGT CCTAGGAAAG GGAATCTTTA     320

CAAAATAAAC AGTGTGGACC CCTCAAAAAA AAAAAAAGC CGAATTC                    367
```

(2) INFORMATION FOR SEQ ID NO: 2:

(i) SEQUENCE CHARACTERISTICS:
             (A) LENGTH: 52 amino acids
             (B) TYPE: amino acid
             (D) TOPOLOGY: linear (ii) MOLECULE TYPE: protein (xi) SEQUENCE DESCRIPTION: SEQ ID NO: 2:

```
Phe Lys Lys Gly Ile Cys Leu Ser Cys Arg Lys Asn Arg Cys Asn Ser
 1               5                  10                  15

Ile Gly Tyr Asn Ala Lys Lys Met Arg Asn Lys Arg Asn Ser Lys Met
            20                  25                  30

Tyr Leu Lys Thr Arg Ala Gly Met Pro Phe Arg Gly Asn Leu Gln Ser
        35                  40                  45

Leu Glu Cys Pro
    50
```

(2) INFORMATION FOR SEQ ID NO: 3:

(i) SEQUENCE CHARACTERISTICS:
             (A) LENGTH: 1382 base pairs
             (B) TYPE: nucleic acid
             (C) STRANDEDNESS: double
             (D) TOPOLOGY: linear (ii) MOLECULE TYPE: cDNA (ix) FEATURE:
             (A) NAME/KEY: CDS
             (B) LOCATION: 312..1370

(xi) SEQUENCE DESCRIPTION: SEQ ID NO: 3:

```
GAATTCGGCT TCTACTACTA CTAGGCCACG CGTCGCCTAG TACGGGGGGG GGGGGGGGGG       60

TCAGCGAGTC CTTGCCTCCC GGCGGCTCAG GACGAGGGCA GATCTCGTTC TGGGGCAAGC     120

CGTTGACACT CGCTCCCTGC CACCGCCCGG GCTCCGTGCC GCCAAGTTTT CATTTTCCAC     180
```

```
CTTCTCTGCC TCCAGTCCCC CAGCCCCTGG CCGAGAGAAG GGTCTTACCG GCCGGGATTG      240

CTGGAAACAC CAAGAGGTGG TTTTTGTTTT TTAAAACTTC TGTTTCTTGG GAGGGGGTGT      300

GGCGGGGCAG G ATG AGC AAC TCC GTT CCT CTG CTC TGT TTC TGG AGC CTC      350
             Met Ser Asn Ser Val Pro Leu Leu Cys Phe Trp Ser Leu
              1               5                  10

TGC TAT TGC TTT GCT GCG GGG AGC CCC GTA CCT TTT GGT CCA GAG GGA       398
Cys Tyr Cys Phe Ala Ala Gly Ser Pro Val Pro Phe Gly Pro Glu Gly
     15              20              25

CGG CTG GAA GAT AAG CTC CAC AAA CCC AAA GCT ACA CAG ACT GAG GTC       446
Arg Leu Glu Asp Lys Leu His Lys Pro Lys Ala Thr Gln Thr Glu Val
 30              35              40                  45

AAA CCA TCT GTG AGG TTT AAC CTC CGC ACC TCC AAG GAC CCA GAG CAT       494
Lys Pro Ser Val Arg Phe Asn Leu Arg Thr Ser Lys Asp Pro Glu His
                 50              55                  60

GAA GGA TGC TAC CTC TCC GTC GGC CAC AGC CAG CCC TTA GAA GAC TGC       542
Glu Gly Cys Tyr Leu Ser Val Gly His Ser Gln Pro Leu Glu Asp Cys
             65              70              75

AGT TTC AAC ATG ACA GCT AAA ACC TTT TTC ATC ATT CAC GGA TGG ACG       590
Ser Phe Asn Met Thr Ala Lys Thr Phe Phe Ile Ile His Gly Trp Thr
         80              85                  90

ATG AGC GGT ATC TTT GAA AAC TGG CTG CAC AAA CTC GTG TCA GCC CTG       638
Met Ser Gly Ile Phe Glu Asn Trp Leu His Lys Leu Val Ser Ala Leu
 95              100             105

CAC ACA AGA GAG AAA GAC GCC AAT GTA GTT GTG GTT GAC TGG CTC CCC       686
His Thr Arg Glu Lys Asp Ala Asn Val Val Val Val Asp Trp Leu Pro
110             115             120                 125

CTG GCC CAC CAG CTT TAC ACG GAT GCG GTC AAT AAT ACC AGG GTG GTG       734
Leu Ala His Gln Leu Tyr Thr Asp Ala Val Asn Asn Thr Arg Val Val
                130             135             140

GGA CAC AGC ATT GCC AGG ATG CTC GAC TGG CTG CAG GAG AAG GAC GAT       782
Gly His Ser Ile Ala Arg Met Leu Asp Trp Leu Gln Glu Lys Asp Asp
            145             150             155

TTT TCT CTC GGG AAT GTC CAC TTG ATC GGC TAC AGC CTC GGA GCG CAC       830
Phe Ser Leu Gly Asn Val His Leu Ile Gly Tyr Ser Leu Gly Ala His
        160             165             170

GTG GCC GGG TAT GCA GGC AAC TTC GTG AAA GGA ACG GTG GGC CGA ATC       878
Val Ala Gly Tyr Ala Gly Asn Phe Val Lys Gly Thr Val Gly Arg Ile
175             180             185

ACA GGT TTG GAT CCT GCC GGG CCC ATG TTT GAA GGG GCC GAC ATC CAC       926
Thr Gly Leu Asp Pro Ala Gly Pro Met Phe Glu Gly Ala Asp Ile His
190             195             200             205

AAG AGG CTC TCT CCG GAC GAT GCA GAT TTT GTG GAT GTC CTC CAC ACC       974
Lys Arg Leu Ser Pro Asp Asp Ala Asp Phe Val Asp Val Leu His Thr
            210             215             220

TAC ACG CGT TCC TTC GGC TTG AGC ATT GGT ATT CAG ATG CCT GTG GGC      1022
Tyr Thr Arg Ser Phe Gly Leu Ser Ile Gly Ile Gln Met Pro Val Gly
        225             230             235

CAC ATT GAC ATC TAC CCC AAT GGG GGT GAC TTC CAG CCA GGC TGT GGA      1070
His Ile Asp Ile Tyr Pro Asn Gly Gly Asp Phe Gln Pro Gly Cys Gly
            240             245             250

CTC AAC GAT GTC TTG GGA TCA ATT GCA TAT GGA ACA ATC ACA GAG GTG      1118
Leu Asn Asp Val Leu Gly Ser Ile Ala Tyr Gly Thr Ile Thr Glu Val
        255             260             265

GTA AAA TGT GAG CAT GAG CGA GCC GTC CAC CTC TTT GTT GAC TCT CTG      1166
Val Lys Cys Glu His Glu Arg Ala Val His Leu Phe Val Asp Ser Leu
270             275             280             285

GTG AAT CAG GAC AAG CCG AGT TTT GCC TTC CAG TGC ACT GAC TCC AAT      1214
Val Asn Gln Asp Lys Pro Ser Phe Ala Phe Gln Cys Thr Asp Ser Asn
            290             295             300
```

```
CGC TTC AAA AAG GGG ATC TGT CTG AGC TGC CGC AAG AAC CGT TGT AAT        1262
Arg Phe Lys Lys Gly Ile Cys Leu Ser Cys Arg Lys Asn Arg Cys Asn
        305                 310                 315

AGC ATT GGC TAC AAT GCC AAG AAA ATG AGG AAC AAG AGG AAC AGC AAA        1310
Ser Ile Gly Tyr Asn Ala Lys Lys Met Arg Asn Lys Arg Asn Ser Lys
        320                 325                 330

ATG TAC CTA AAA ACC CGG GCA GGC ATG CCT TTC AGA GGT AAC CTT CAG        1358
Met Tyr Leu Lys Thr Arg Ala Gly Met Pro Phe Arg Gly Asn Leu Gln
        335                 340                 345

TCC CTG GAG TGT CAAGCCGAAT TC                                          1382
Ser Leu Glu Cys
350
```

(2) INFORMATION FOR SEQ ID NO: 4:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ser Asn Ser Val Pro Leu Leu Cys Phe Trp Ser Leu Cys Tyr Cys
 1               5                  10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
    50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
        130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Ala Asp Ile His Lys Arg Leu
            195                 200                 205

Ser Pro Asp Asp Ala Asp Phe Val Asp Val Leu His Thr Tyr Thr Arg
        210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
                260                 265                 270
```

```
Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
        290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Gly Asn Leu Gln Ser Leu Glu
                340                 345                 350

Cys
```

(2) INFORMATION FOR SEQ ID NO: 5:

(i) SEQUENCE CHARACTERISTICS:
      (A) LENGTH: 2565 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 252..1754

(xi) SEQUENCE DESCRIPTION: SEQ ID NO: 5:

```
GAATTCGCGG CCGCGTCGAC GGCGGCTCAG GACGAGGGCA GATCTCGTTC TGGGGCAAGC         60

CGTTGACACT CGCTCCCTGC CACCGCCCGG GCTCCGTGCC GCCAAGTTTT CATTTTCCAC        120

CTTCTCTGCC TCCAGTCCCC CAGCCCCTGG CCGAGAGAAG GGTCTTACCG GCCGGGATTG        180

CTGGAAACAC CAAGAGGTGG TTTTTGTTTT TTAAAACTTC TGTTTCTTGG GAGGGGGTGT        240

GGCGGGGCAG G ATG AGC AAC TCC GTT CCT CTG CTC TGT TTC TGG AGC CTC         290
             Met Ser Asn Ser Val Pro Leu Leu Cys Phe Trp Ser Leu
             1               5                   10

TGC TAT TGC TTT GCT GCG GGG AGC CCC GTA CCT TTT GGT CCA GAG GGA          338
Cys Tyr Cys Phe Ala Ala Gly Ser Pro Val Pro Phe Gly Pro Glu Gly
        15                  20                  25

CGG CTG GAA GAT AAG CTC CAC AAA CCC AAA GCT ACA CAG ACT GAG GTC          386
Arg Leu Glu Asp Lys Leu His Lys Pro Lys Ala Thr Gln Thr Glu Val
30                  35                  40                  45

AAA CCA TCT GTG AGG TTT AAC CTC CGC ACC TCC AAG GAC CCA GAG CAT          434
Lys Pro Ser Val Arg Phe Asn Leu Arg Thr Ser Lys Asp Pro Glu His
            50                  55                  60

GAA GGA TGC TAC CTC TCC GTC GGC CAC AGC CAG CCC TTA GAA GAC TGC          482
Glu Gly Cys Tyr Leu Ser Val Gly His Ser Gln Pro Leu Glu Asp Cys
            65                  70                  75

AGT TTC AAC ATG ACA GCT AAA ACC TTT TTC ATC ATT CAC GGA TGG ACG          530
Ser Phe Asn Met Thr Ala Lys Thr Phe Phe Ile Ile His Gly Trp Thr
        80                  85                  90

ATG AGC GGT ATC TTT GAA AAC TGG CTG CAC AAA CTC GTG TCA GCC CTG          578
Met Ser Gly Ile Phe Glu Asn Trp Leu His Lys Leu Val Ser Ala Leu
        95                 100                 105

CAC ACA AGA GAG AAA GAC GCC AAT GTA GTT GTG GTT GAC TGG CTC CCC          626
His Thr Arg Glu Lys Asp Ala Asn Val Val Val Val Asp Trp Leu Pro
110                 115                 120                 125

CTG GCC CAC CAG CTT TAC ACG GAT GCG GTC AAT AAT ACC AGG GTG GTG          674
Leu Ala His Gln Leu Tyr Thr Asp Ala Val Asn Asn Thr Arg Val Val
            130                 135                 140
```

```
GGA CAC AGC ATT GCC AGG ATG CTC GAC TGG CTG CAG GAG AAG GAC GAT        722
Gly His Ser Ile Ala Arg Met Leu Asp Trp Leu Gln Glu Lys Asp Asp
            145                 150                 155

TTT TCT CTC GGG AAT GTC CAC TTG ATC GGC TAC AGC CTC GGA GCG CAC        770
Phe Ser Leu Gly Asn Val His Leu Ile Gly Tyr Ser Leu Gly Ala His
        160                 165                 170

GTG GCC GGG TAT GCA GGC AAC TTC GTG AAA GGA ACG GTG GGC CGA ATC        818
Val Ala Gly Tyr Ala Gly Asn Phe Val Lys Gly Thr Val Gly Arg Ile
    175                 180                 185

ACA GGT TTG GAT CCT GCC GGG CCC ATG TTT GAA GGG GCC GAC ATC CAC        866
Thr Gly Leu Asp Pro Ala Gly Pro Met Phe Glu Gly Ala Asp Ile His
190                 195                 200                 205

AAG AGG CTC TCT CCG GAC GAT GCA GAT TTT GTG GAT GTC CTC CAC ACC        914
Lys Arg Leu Ser Pro Asp Asp Ala Asp Phe Val Asp Val Leu His Thr
                210                 215                 220

TAC ACG CGT TCC TTC GGC TTG AGC ATT GGT ATT CAG ATG CCT GTG GGC        962
Tyr Thr Arg Ser Phe Gly Leu Ser Ile Gly Ile Gln Met Pro Val Gly
            225                 230                 235

CAC ATT GAC ATC TAC CCC AAT GGG GGT GAC TTC CAG CCA GGC TGT GGA       1010
His Ile Asp Ile Tyr Pro Asn Gly Gly Asp Phe Gln Pro Gly Cys Gly
        240                 245                 250

CTC AAC GAT GTC TTG GGA TCA ATT GCA TAT GGA ACA ATC ACA GAG GTG       1058
Leu Asn Asp Val Leu Gly Ser Ile Ala Tyr Gly Thr Ile Thr Glu Val
    255                 260                 265

GTA AAA TGT GAG CAT GAG CGA GCC GTC CAC CTC TTT GTT GAC TCT CTG       1106
Val Lys Cys Glu His Glu Arg Ala Val His Leu Phe Val Asp Ser Leu
270                 275                 280                 285

GTG AAT CAG GAC AAG CCG AGT TTT GCC TTC CAG TGC ACT GAC TCC AAT       1154
Val Asn Gln Asp Lys Pro Ser Phe Ala Phe Gln Cys Thr Asp Ser Asn
                290                 295                 300

CGC TTC AAA AAG GGG ATC TGT CTG AGC TGC CGC AAG AAC CGT TGT AAT       1202
Arg Phe Lys Lys Gly Ile Cys Leu Ser Cys Arg Lys Asn Arg Cys Asn
            305                 310                 315

AGC ATT GGC TAC AAT GCC AAG AAA ATG AGG AAC AAG AGG AAC AGC AAA       1250
Ser Ile Gly Tyr Asn Ala Lys Lys Met Arg Asn Lys Arg Asn Ser Lys
        320                 325                 330

ATG TAC CTA AAA ACC CGG GCA GGC ATG CCT TTC AGA GTT TAC CAT TAT       1298
Met Tyr Leu Lys Thr Arg Ala Gly Met Pro Phe Arg Val Tyr His Tyr
    335                 340                 345

CAG ATG AAA ATC CAT GTC TTC AGT TAC AAG AAC ATG GGA GAA ATT GAG       1346
Gln Met Lys Ile His Val Phe Ser Tyr Lys Asn Met Gly Glu Ile Glu
350                 355                 360                 365

CCC ACC TTT TAC GTC ACC CTT TAT GGC ACT AAT GCA GAT TCC CAG ACT       1394
Pro Thr Phe Tyr Val Thr Leu Tyr Gly Thr Asn Ala Asp Ser Gln Thr
                370                 375                 380

CTG CCA CTG GAA ATA GTG GAG CGG ATC GAG CAG AAT GCC ACC AAC ACC       1442
Leu Pro Leu Glu Ile Val Glu Arg Ile Glu Gln Asn Ala Thr Asn Thr
            385                 390                 395

TTC CTG GTC TAC ACC GAG GAG GAC TTG GGA GAC CTC TTG AAG ATC CAG       1490
Phe Leu Val Tyr Thr Glu Glu Asp Leu Gly Asp Leu Leu Lys Ile Gln
        400                 405                 410

CTC ACC TGG GAG GGG GCC TCT CAG TCT TGG TAC AAC CTG TGG AAG GAG       1538
Leu Thr Trp Glu Gly Ala Ser Gln Ser Trp Tyr Asn Leu Trp Lys Glu
    415                 420                 425

TTT CGC AGC TAC CTG TCT CAA CCC CGC AAC CCC GGA CGG GAG CTG AAT       1586
Phe Arg Ser Tyr Leu Ser Gln Pro Arg Asn Pro Gly Arg Glu Leu Asn
430                 435                 440                 445

ATC AGG CGC ATC CGG GTG AAG TCT GGG GAA ACC CAG CGG AAA CTG ACA       1634
Ile Arg Arg Ile Arg Val Lys Ser Gly Glu Thr Gln Arg Lys Leu Thr
                450                 455                 460
```

-continued

```
TTT TGT ACA GAA GAC CCT GAG AAC ACC AGC ATA TCC CCA GGC CGG GAG      1682
Phe Cys Thr Glu Asp Pro Glu Asn Thr Ser Ile Ser Pro Gly Arg Glu
            465                 470                 475

CTC TGG TTT CGC AAG TGT CGG GAT GGC TGG AGG ATG AAA AAC GAA ACC      1730
Leu Trp Phe Arg Lys Cys Arg Asp Gly Trp Arg Met Lys Asn Glu Thr
            480                 485                 490

AGT CCC ACT GTG GAG CTT CCC TGA GGGTGCCCGG GCAAGTCTTG CCAGCAAGGC     1784
Ser Pro Thr Val Glu Leu Pro
            495             500

AGCAAGACTT CCTGCTATCC AAGCCCATGG AGGAAAGTTA CTGCTGAGGA CCCACCCAAT    1844

GGAAGGATTC TTCTCAGCCT TGACCCTGGA GCACTGGGAA CAACTGGTCT CCTGTGATGG    1904

CTGGGACTCC TCGCGGGAGG GGACTGCGCT GCTATAGCTC TTGCTGCCTC TCTTGAATAG    1964

CTCTAACTCC AAACCTCTGT CCACACCTCC AGAGCACCAA GTCCAGATTT GTGTGTAAGC    2024

AGCTGGGTGC CTGGGGCCTC TCGTGCACAC TGGATTGGTT TCTCAGTTGC TGGGCGAGCC    2084

TGTACTCTGC CTGACGAGGA ACGCTGGCTC CGAAGAGGCC CTGTGTAGAA GGCTGTCAGC    2144

TGCTCAGCCT GCTTTGAGCC TCAGTGAGAA GTCCTTCCGA CAGGAGCTGA CTCATGTCAG    2204

GATGGCAGGC CTGGTATCTT GCTCGGGCCC TGGCTGTTGG GGTTCTCATG GGTTGCACTG    2264

ACCATACTGC TTACGTCTTA GCCATTCCGT CCTGCTCCCC AGCTCACTCT CTGAAGCACA    2324

CATCATTGGC TTTCCTATTT TTCTGTTCAT TTTTTAATTG AGCAAATGTC TATTGAACAC    2384

TTAAAATTAA TTAGAATGTG GTAATGGACA TATTACTGAG CCTCTCCATT TGGAACCCAG    2444

TGGAGTTGGG ATTTCTAGAC CCTCTTTCTG TTTGGATGGT GTATGTGTAT ATGCATGGGG    2504

AAAGGCACCT GGGGCCTGGG GGAGGCTATA GGATATAAGC AGTCGACGCG GCCGCGAATT    2564

C                                                                    2565

(2) INFORMATION FOR SEQ ID NO: 6:

(i) SEQUENCE CHARACTERISTICS:
        (A) LENGTH: 500 amino acids
        (B) TYPE: amino acid
        (D) TOPOLOGY: linear (ii) MOLECULE TYPE: protein (xi) SEQUENCE DESCRIPTION: SEQ ID NO: 6:

Met Ser Asn Ser Val Pro Leu Leu Cys Phe Trp Ser Leu Cys Tyr Cys
 1               5                  10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
        50                  55                  60

Tyr Leu Ser Val Gly His Ser Gln Pro Leu Glu Asp Cys Ser Phe Asn
 65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
        130                 135                 140
```

```
Ile Ala Arg Met Leu Asp Trp Leu Gln Glu Lys Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Ala Asp Ile His Lys Arg Leu
            195                 200                 205

Ser Pro Asp Asp Ala Asp Phe Val Asp Val Leu His Thr Tyr Thr Arg
    210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
                260                 265                 270

Glu His Glu Arg Ala Val His Leu Phe Val Asp Ser Leu Val Asn Gln
            275                 280                 285

Asp Lys Pro Ser Phe Ala Phe Gln Cys Thr Asp Ser Asn Arg Phe Lys
290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Val Tyr His Tyr Gln Met Lys
                340                 345                 350

Ile His Val Phe Ser Tyr Lys Asn Met Gly Glu Ile Glu Pro Thr Phe
            355                 360                 365

Tyr Val Thr Leu Tyr Gly Thr Asn Ala Asp Ser Gln Thr Leu Pro Leu
370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Phe Arg Ser
                420                 425                 430

Tyr Leu Ser Gln Pro Arg Asn Pro Gly Arg Glu Leu Asn Ile Arg Arg
            435                 440                 445

Ile Arg Val Lys Ser Gly Glu Thr Gln Arg Lys Leu Thr Phe Cys Thr
450                 455                 460

Glu Asp Pro Glu Asn Thr Ser Ile Ser Pro Gly Arg Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro
            500
```

(2) INFORMATION FOR SEQ ID NO: 7:

(i) SEQUENCE CHARACTERISTICS:
        (A) LENGTH: 225 base pairs
        (B) TYPE: nucleic acid
        (C) STRANDEDNESS: double
        (D) TOPOLOGY: linear (ii) MOLECULE TYPE: cDNA (ix) FEATURE:
    (A) NAME/KEY: CDS
    (B) LOCATION: 1..225

(xi) SEQUENCE DESCRIPTION: SEQ ID NO: 7:

```
CTG GGA TCC ATC GCC TAT GGC ACG ATC GCG GAG GTG GTG AAG TGC GAG      48
Leu Gly Ser Ile Ala Tyr Gly Thr Ile Ala Glu Val Val Lys Cys Glu
1               5                   10                  15

CAT GAG CGG GCC GTG CAT CTC TTT GTG GAC TCC CTG GTG AAC CAG GAC      96
His Glu Arg Ala Val His Leu Phe Val Asp Ser Leu Val Asn Gln Asp
            20                  25                  30

AAG CCG AGC TTT GCC TTC CAG TGC ACA GAC TCC AAC CGC TTC AAA AAA     144
Lys Pro Ser Phe Ala Phe Gln Cys Thr Asp Ser Asn Arg Phe Lys Lys
        35                  40                  45

GGG ATC TGT CTC AGC TGC CGG AAG AAC CGC TGT AAC GGC ATC GGC TAC     192
Gly Ile Cys Leu Ser Cys Arg Lys Asn Arg Cys Asn Gly Ile Gly Tyr
    50                  55                  60

AAT GCT AAG AAG ACG AGG AAT AAG AGG AAC ACC                         225
Asn Ala Lys Lys Thr Arg Asn Lys Arg Asn Thr
65                  70                  75
```

(2) INFORMATION FOR SEQ ID NO: 8:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO: 8:

```
Leu Gly Ser Ile Ala Tyr Gly Thr Ile Ala Glu Val Val Lys Cys Glu
1               5                   10                  15

His Glu Arg Ala Val His Leu Phe Val Asp Ser Leu Val Asn Gln Asp
            20                  25                  30

Lys Pro Ser Phe Ala Phe Gln Cys Thr Asp Ser Asn Arg Phe Lys Lys
        35                  40                  45

Gly Ile Cys Leu Ser Cys Arg Lys Asn Arg Cys Asn Gly Ile Gly Tyr
    50                  55                  60

Asn Ala Lys Lys Thr Arg Asn Lys Arg Asn Thr
65                  70                  75
```

(2) INFORMATION FOR SEQ ID NO: 9:

(i) SEQUENCE CHARACTERISTICS:
        (A) LENGTH: 475 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 9:

```
Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp
        35                  40                  45

Thr Ala Glu Asp Thr Cys His Leu Ile Pro Gly Val Ala Glu Ser Val
    50                  55                  60
```

```
Ala Thr Cys His Phe Asn His Ser Ser Lys Thr Phe Met Val Ile His
 65                  70                  75                  80

Gly Trp Thr Val Thr Gly Met Tyr Glu Ser Trp Val Pro Lys Leu Val
                 85                  90                  95

Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
            115                 120                 125

Lys Leu Val Gly Gln Asp Val Ala Arg Phe Ile Asn Trp Met Glu Glu
        130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
            195                 200                 205

Leu His Thr Phe Thr Arg Gly Ser Pro Gly Arg Ser Ile Gly Ile Gln
    210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
            245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Ser Ser Lys Glu Ala Phe Glu Lys Gly Leu Cys Leu Ser
    290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
            325                 330                 335

Pro Tyr Lys Val Phe His Tyr Gln Val Lys Ile His Phe Ser Gly Thr
            340                 345                 350

Glu Ser Glu Thr His Thr Asn Gln Ala Phe Glu Ile Ser Leu Tyr Gly
        355                 360                 365

Thr Val Ala Glu Ser Glu Asn Ile Pro Phe Thr Leu Pro Glu Val Ser
    370                 375                 380

Thr Asn Lys Thr Tyr Ser Phe Leu Ile Tyr Thr Glu Val Asp Ile Gly
385                 390                 395                 400

Glu Leu Leu Met Leu Lys Leu Lys Trp Lys Ser Asp Ser Tyr Phe Ser
            405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Val Ile Phe Cys Ser Arg Glu
        435                 440                 445

Lys Val Ser His Leu Gln Lys Gly Lys Ala Pro Ala Val Phe Val Lys
    450                 455                 460

Cys His Asp Lys Ser Leu Asn Lys Lys Ser Gly
465                 470                 475
```

```
(2) INFORMATION FOR SEQ ID NO: 10:

(i) SEQUENCE CHARACTERISTICS:
        (A) LENGTH: 499 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 10:

Met Asp Thr Ser Pro Leu Cys Phe Ser Ile Leu Leu Val Leu Cys Ile
1               5                   10                  15

Phe Ile Gln Ser Ser Ala Leu Gly Gln Ser Leu Lys Pro Glu Pro Phe
                20                  25                  30

Gly Arg Arg Ala Gln Ala Val Glu Thr Asn Lys Thr Leu His Glu Met
            35                  40                  45

Lys Thr Arg Phe Leu Leu Phe Gly Glu Thr Asn Gln Gly Cys Gln Ile
        50                  55                  60

Arg Ile Asn His Pro Asp Thr Leu Gln Glu Cys Gly Phe Asn Ser Ser
65                  70                  75                  80

Leu Pro Leu Val Met Ile Ile His Gly Trp Ser Val Asp Gly Val Leu
                85                  90                  95

Glu Asn Trp Ile Trp Gln Met Val Ala Ala Leu Lys Ser Gln Pro Ala
                100                 105                 110

Gln Pro Val Asn Val Gly Leu Val Asp Trp Ile Thr Leu Ala His Asp
                115                 120                 125

His Tyr Thr Ile Ala Val Arg Asn Thr Arg Leu Val Gly Lys Glu Val
        130                 135                 140

Ala Ala Leu Leu Arg Trp Leu Glu Glu Ser Val Gln Leu Ser Arg Ser
145                 150                 155                 160

His Val His Leu Ile Gly Tyr Ser Leu Gly Ala His Val Ser Gly Phe
                165                 170                 175

Ala Gly Ser Ser Ile Gly Gly Thr His Lys Ile Gly Arg Ile Thr Gly
                180                 185                 190

Leu Asp Ala Ala Gly Pro Leu Phe Glu Gly Ser Ala Pro Ser Asn Arg
                195                 200                 205

Leu Ser Pro Asp Asp Ala Asn Phe Val Asp Ala Ile His Thr Phe Thr
        210                 215                 220

Arg Glu His Met Gly Leu Ser Val Gly Ile Lys Gln Pro Ile Gly His
225                 230                 235                 240

Tyr Asp Phe Tyr Pro Asn Gly Gly Ser Phe Gln Pro Gly Cys His Phe
                245                 250                 255

Leu Glu Leu Tyr Arg His Ile Ala Gln His Gly Phe Asn Ala Ile Thr
                260                 265                 270

Gln Thr Ile Lys Cys Ser His Glu Arg Ser Val His Leu Phe Ile Asp
        275                 280                 285

Ser Leu Leu His Ala Gly Thr Gln Ser Met Ala Tyr Pro Cys Gly Asp
290                 295                 300

Met Asn Ser Phe Ser Gln Gly Leu Cys Leu Ser Cys Lys Lys Gly Arg
305                 310                 315                 320

Cys Asn Thr Leu Gly Tyr His Val Arg Gln Glu Pro Arg Ser Lys Ser
                325                 330                 335

Lys Arg Leu Phe Leu Val Thr Arg Ala Gln Ser Pro Phe Lys Val Tyr
                340                 345                 350
```

```
His Tyr Gln Leu Lys Ile Gln Phe Ile Asn Gln Thr Glu Thr Pro Ile
            355                 360                 365

Gln Thr Thr Phe Thr Met Ser Leu Leu Gly Thr Lys Glu Lys Met Gln
    370                 375                 380

Lys Ile Pro Ile Thr Leu Gly Lys Gly Ile Ala Ser Asn Lys Thr Tyr
385                 390                 395                 400

Ser Phe Leu Ile Thr Leu Asp Val Asp Ile Gly Glu Leu Ile Met Ile
                405                 410                 415

Lys Phe Lys Trp Glu Asn Ser Ala Val Trp Ala Asn Val Trp Asp Thr
            420                 425                 430

Val Gln Thr Ile Ile Pro Trp Ser Thr Gly Pro Arg His Ser Gly Leu
        435                 440                 445

Val Leu Lys Thr Ile Arg Val Lys Ala Gly Glu Thr Gln Gln Arg Met
    450                 455                 460

Thr Phe Cys Ser Glu Asn Thr Asp Asp Leu Leu Leu Arg Pro Thr Gln
465                 470                 475                 480

Glu Lys Ile Phe Val Lys Cys Glu Ile Lys Ser Lys Thr Ser Lys Arg
                485                 490                 495

Lys Ile Arg (2) INFORMATION FOR SEQ ID NO: 11:

(i) SEQUENCE CHARACTERISTICS:
        (A) LENGTH: 465 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 11:

Met Leu Pro Leu Trp Thr Leu Ser Leu Leu Gly Ala Val Ala Gly
1               5                   10                  15

Lys Glu Val Cys Tyr Glu Arg Leu Gly Cys Phe Ser Asp Asp Ser Pro
                20                  25                  30

Trp Ser Gly Ile Thr Glu Arg Pro Leu His Ile Leu Pro Trp Ser Pro
            35                  40                  45

Lys Asp Val Asn Thr Arg Phe Leu Leu Tyr Thr Asn Glu Asn Pro Asn
50                  55                  60

Asn Phe Gln Glu Val Ala Ala Asp Ser Ser Ile Ser Gly Ser Asn
65                  70                  75                  80

Phe Lys Thr Asn Arg Lys Thr Arg Phe Ile Ile His Gly Phe Ile Asp
            85                  90                  95

Lys Gly Glu Glu Asn Trp Leu Ala Asn Val Cys Lys Asn Leu Phe Lys
                100                 105                 110

Val Glu Ser Val Asn Cys Ile Cys Val Asp Trp Lys Gly Gly Ser Arg
            115                 120                 125

Thr Gly Tyr Thr Gln Ala Ser Gln Asn Ile Arg Ile Val Gly Ala Glu
    130                 135                 140

Val Ala Tyr Phe Val Glu Phe Leu Gln Ser Ala Phe Gly Tyr Ser Pro
145                 150                 155                 160

Ser Asn Val His Val Ile Gly His Ser Leu Gly Ala His Ala Ala Gly
                165                 170                 175

Glu Ala Gly Arg Arg Thr Asn Gly Thr Ile Gly Arg Ile Thr Gly Leu
            180                 185                 190
```

```
Asp Pro Ala Glu Pro Cys Phe Gln Gly Thr Pro Glu Leu Val Arg Leu
        195                 200                 205

Asp Pro Ser Asp Ala Lys Phe Val Asp Val Ile His Thr Asp Gly Ala
        210                 215                 220

Pro Ile Val Pro Asn Leu Gly Phe Gly Met Ser Gln Val Val Gly His
225                 230                 235                 240

Leu Asp Phe Phe Pro Asn Gly Val Glu Met Pro Gly Cys Lys Lys
                245                 250                 255

Asn Ile Leu Ser Gln Ile Val Asp Ile Asp Gly Ile Trp Glu Gly Thr
            260                 265                 270

Arg Asp Phe Ala Ala Cys Asn His Leu Arg Ser Tyr Lys Tyr Tyr Thr
        275                 280                 285

Asp Ser Ile Val Asn Pro Asp Gly Phe Ala Gly Phe Pro Cys Ala Ser
290                 295                 300

Tyr Asn Val Phe Thr Ala Asn Lys Cys Phe Pro Cys Pro Ser Gly Gly
305                 310                 315                 320

Cys Pro Gln Met Gly His Tyr Ala Asp Arg Tyr Pro Gly Lys Thr Asn
                325                 330                 335

Asp Val Gly Gln Lys Phe Tyr Leu Asp Thr Gly Asp Ala Ser Asn Phe
            340                 345                 350

Ala Arg Trp Arg Tyr Lys Val Ser Val Thr Leu Ser Gly Lys Lys Val
        355                 360                 365

Thr Gly His Ile Leu Val Ser Leu Phe Gly Asn Lys Gly Asn Ser Lys
370                 375                 380

Gln Tyr Glu Ile Phe Lys Gly Thr Leu Lys Pro Asp Ser Thr His Ser
385                 390                 395                 400

Asn Glu Phe Asp Ser Asp Val Asp Val Gly Asp Leu Gln Met Val Lys
                405                 410                 415

Phe Ile Trp Tyr Asn Asn Val Ile Asn Pro Thr Leu Pro Arg Val Gly
            420                 425                 430

Ala Ser Lys Ile Ile Val Glu Thr Asn Val Gly Lys Gln Phe Asn Phe
        435                 440                 445

Cys Ser Pro Glu Thr Val Arg Glu Glu Val Leu Leu Thr Leu Thr Pro
450                 455                 460

Cys
465

(2) INFORMATION FOR SEQ ID NO: 12:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (xi) SEQUENCE DESCRIPTION: SEQ ID NO: 12:

Gly Pro Glu Gly Arg Leu Glu Asp Lys Leu His Lys Pro Lys Ala Thr
1               5                   10                  15

Cys
```

(2) INFORMATION FOR SEQ ID NO: 13:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 13:

TTTTTTTTTT TGA                                                13

(2) INFORMATION FOR SEQ ID NO: 14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 14:

GATCAATCGC                                                    10

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 15:

TAGGACATGC ACAGTGTAAT CTG                                23

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 16:

GATTGTGCTG GCCACTTCTC                                    20

(2) INFORMATION FOR SEQ ID NO: 17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 17:

GACACTCCAG GGACTGAAG                                     19

```
(2) INFORMATION FOR SEQ ID NO: 18:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(ix) FEATURE:
        (A) NAME/KEY: modified_base
        (B) LOCATION: 36
        (D) OTHER INFORMATION: /mod_base= i (ix) FEATURE:
        (A) NAME/KEY: modified_base
        (B) LOCATION: 37
        (D) OTHER INFORMATION: /mod_base= i (ix) FEATURE:
        (A) NAME/KEY: modified_base
        (B) LOCATION: 41
        (D) OTHER INFORMATION: /mod_base= i (ix) FEATURE:
        (A) NAME/KEY: modified_base
        (B) LOCATION: 42
        (D) OTHER INFORMATION: /mod_base= i (ix) FEATURE:
        (A) NAME/KEY: modified_base
        (B) LOCATION: 46
        (D) OTHER INFORMATION: /mod_base= i (ix) FEATURE:
        (A) NAME/KEY: modified_base
        (B) LOCATION: 47
        (D) OTHER INFORMATION: /mod_base= i (xi) SEQUENCE DESCRIPTION: SEQ ID NO: 18:

CUACUACUAC UAGGCCACGC GTCGACTAGT ACGGGNNGGG NNGGGNNG                    48

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 19:

CACACACAGG CCACGCGTCG ACTAGTAC                                          28

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 20:

ACCACCATGG AGAGCAAAGC CCTG                                              24
```

(2) INFORMATION FOR SEQ ID NO: 21:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Oligonucleotide"

(xi) SEQUENCE DESCRIPTION: SEQ ID NO: 21:

CCAGTTTCAG CCTGACTTCT TATTC                                    25

(2) INFORMATION FOR SEQ ID NO: 22:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Oligonucleotide"

(xi) SEQUENCE DESCRIPTION: SEQ ID NO: 22:

GGCTGTGGAC TCAACGATGT C                                        21

(2) INFORMATION FOR SEQ ID NO: 23:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Oligonucleotide"

(xi) SEQUENCE DESCRIPTION: SEQ ID NO: 23:

CCGGGTGGGT AGGTACATTT TG                                       22

(2) INFORMATION FOR SEQ ID NO: 24:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Oligonucleotide"

(xi) SEQUENCE DESCRIPTION: SEQ ID NO: 24:

GGGGGTGACT TCCAGCCAGG CTGTG                                    25

(2) INFORMATION FOR SEQ ID NO: 25:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Oligonucleotide"

(xi) SEQUENCE DESCRIPTION: SEQ ID NO: 25:

AACTCTGAAA GGCATGCCTG CCCGG                                    25

-continued (2) INFORMATION FOR SEQ ID NO: 26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 26:

TGAAGGTCGG AGTCAACGGA TTTGGT      26

(2) INFORMATION FOR SEQ ID NO: 27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 27:

CATGTGGGCC ATGAGGTCCA CCAC      24